(12) United States Patent
Kalyuzhnaya et al.

(10) Patent No.: US 11,629,173 B2
(45) Date of Patent: Apr. 18, 2023

(54) COMPOSITIONS AND METHODS USING METHANOTROPHIC S-LAYER PROTEINS FOR EXPRESSION OF HETEROLOGOUS PROTEINS

(71) Applicant: San Diego State University (SDSU) Foundation, San Diego, CA (US)

(72) Inventors: Marina Kalyuzhnaya, San Diego, CA (US); Oleksandr Demidenko, San Diego, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 56 days.

(21) Appl. No.: 16/643,390

(22) PCT Filed: Aug. 29, 2018

(86) PCT No.: PCT/US2018/048576
§ 371 (c)(1),
(2) Date: Feb. 28, 2020

(87) PCT Pub. No.: WO2019/046446
PCT Pub. Date: Mar. 7, 2019

(65) Prior Publication Data
US 2021/0070810 A1    Mar. 11, 2021

Related U.S. Application Data

(60) Provisional application No. 62/551,502, filed on Aug. 29, 2017, provisional application No. 62/551,490, filed on Aug. 29, 2017.

(51) Int. Cl.
C07K 14/195 (2006.01)
C12N 9/20 (2006.01)
C12N 15/62 (2006.01)
C12N 15/74 (2006.01)

(52) U.S. Cl.
CPC .............. *C07K 14/195* (2013.01); *C12N 9/20* (2013.01); *C12N 15/62* (2013.01); *C12N 15/74* (2013.01); *C07K 2317/24* (2013.01); *C07K 2319/50* (2013.01); *C07K 2319/735* (2013.01)

(58) Field of Classification Search
None
See application file for complete search history.

(56) References Cited

U.S. PATENT DOCUMENTS

| 2004/0175705 A1 | 9/2004 | Birkeland et al. |
| 2011/0189743 A1 | 8/2011 | Yoshikuni et al. |
| 2015/0366992 A1 | 12/2015 | Kim et al. |
| 2016/0237442 A1 | 8/2016 | Puri et al. |

FOREIGN PATENT DOCUMENTS

| EP | 3106521 A1 | 12/2016 |
| WO | 9519371 | 7/1995 |
| WO | 2017132627 A2 | 8/2017 |

OTHER PUBLICATIONS

Fagan, R.P. & Fairweather, N.F., "Biogenesis and functions of bacterial S-layers", Nature Reviews, Microbiology, 2014, vol. 12, pp. 211-222.*
Collins, D.A.I., "Dissecting the cellular biology of the model methanotroph Methylotuvimicrobium alcaliphilum 20ZR through multi-omics, mutagenesis, and microscopy", PhD thesis, San Diego State University, 2021.*
Kunte et al., "Industrial production of the cell protectant ectoine: protection mechanisms, processes and products" Curent Biotechnology, 2014, v 3, p. 10-25.
Pastor et al., "Ectoines in cell stress protection: uses and biotechnological production" Biotechnology Advances, 2010, v 28, p. 782-801.
Copenheaver, International Search Report and Written Opinion for PCT/US2018/048576, dated Feb. 21, 2019.
Shchukin et al., "Primary characterization of dominant cell surface proteins of halotolerant methanotroph methylomicrobium alcaliphilum 20Z" Microbilogy, 2011, v 80, n 5, p. 608-618.
Strong et al., "A methanotroph-based biorefinery: Potential scenarios for generating multiple products from a single fermentation" Bioresource Technology, 2016, v 215, p. 314-323.
Timmers et al., "Reverse methanogenesis and respiration in methanotrophic archaea" Archaea, v 2017, 22 pages.

(Continued)

*Primary Examiner* — Suzanne M Noakes
(74) *Attorney, Agent, or Firm* — Greer, Burns & Crain, Ltd.; Gregory P. Einhorn

(57) ABSTRACT

In alternative embodiments, provided are compositions and methods for making a chimeric polypeptide comprising an S-layer polypeptide and a heterologous polypeptide or peptide. In alternative embodiments, the compositions and methods comprise recombinantly engineering a methylotrophic or methanotrophic bacteria to recombinantly express a chimeric polypeptide comprising an S-layer polypeptide and a heterologous polypeptide or peptide. Also provided are compositions and methods for displaying or immobilizing proteins on a methanotrophic S-layer. In alternative embodiments, provided are compositions and methods comprising recombinant methylotrophic or methanotrophic bacteria comprising assembled or self-assembled recombinant or isolated chimeric S-layer polypeptides. In alternative embodiments, provided are compositions and methods using recombinant methylotrophic or methanotrophic bacteria, optionally a *Methylomicrobium alcaliphilum*, optionally a *M. alcaliphilum* sp. 20Z, for ectoine ((4S)-2-methyl-1,4,5,6-tetrahydropyrimidine-4-carboxylic acid), for the production or synthesis of a protein, e.g., an ectoine, or an enzyme, e.g., a lipase.

20 Claims, 19 Drawing Sheets

Specification includes a Sequence Listing.

(56) References Cited

OTHER PUBLICATIONS

Vollenkle et al., "Construction of a functional s-layer fusion protein comprising an immunoglobulin g-binding domain for development of specific adsorbents for extracorporeal blood purification" Applied and Environmental Microbiology, 2004, v 70, n 3, p. 1514-1521.
Schuster et al., "S-layer proteins as key components of a versatile molecular construction kit for biomedical nanotechnology" Mini-Reviews in Medicinal Chemistry, 2006, v 6, p. 909-920.
Sleytr et al., "S-layers as a basic building block in amolecular construction kit" FEBS Journal, 2007, v 274, p. 323-334.
Reshetnikov et al., "Diversity and phylogeny of the ectoine biosynthesis genes in aerobic, moderately halophilic methylotrophic bateria" Extremophiles, 2011, v 15, p. 653-663.
Orata et al., "Phylogenomic Analysis of the Gammaproteobacterial Methanotrophs (Order Methylococcales) Calls for the Reclassification of Members at the Genus and Species Levels" Frontiers in Microbiology, Dec. 2018, v 19, Article 3162, p. 1-17.

* cited by examiner

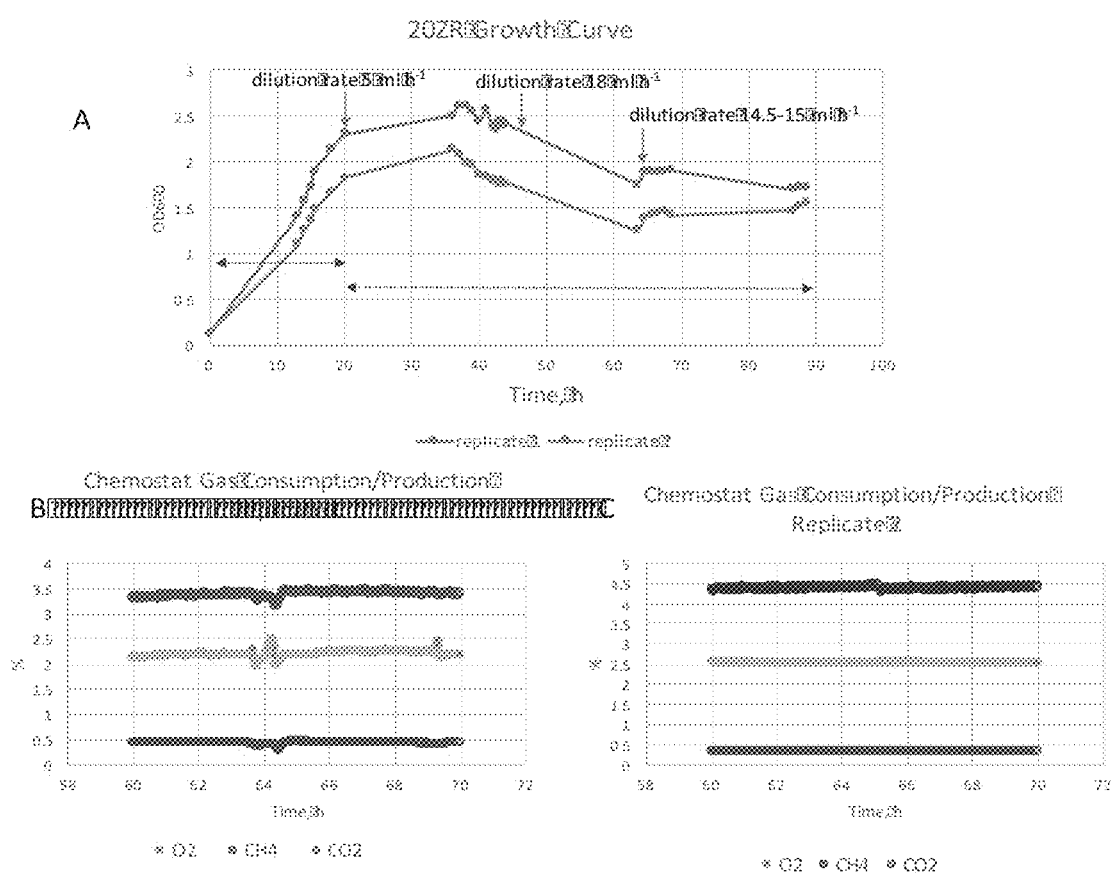
FIG. 4A-C

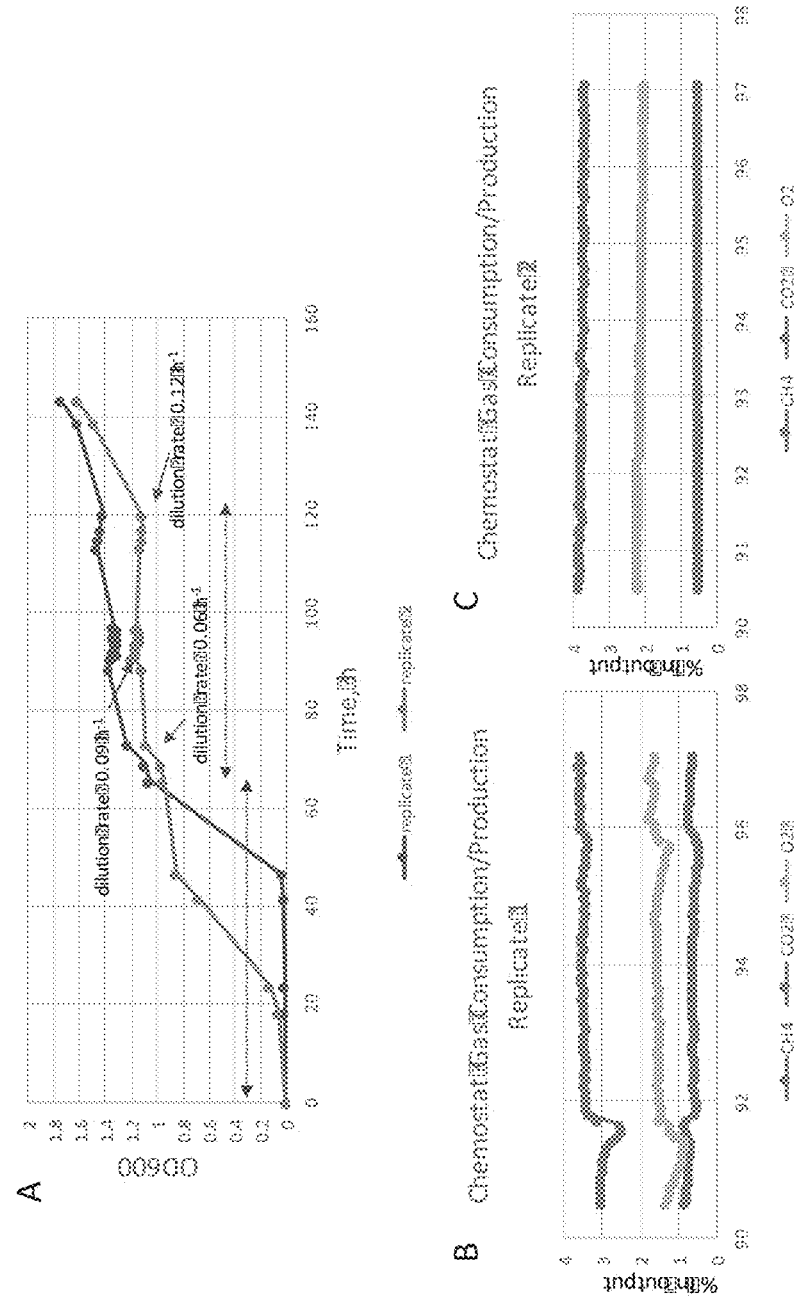
FIG. 10A-C

FIG. 11

Isolation 1:
0.00  0.25  0.50  R₂  0.75  1.00

Isolation 2:
0.00  0.25  0.50  R₃  0.75  1.00

Isolation 3:
0.00  0.25  0.50  R₄  0.75  1.00

COMPOSITIONS AND METHODS USING METHANOTROPHIC S-LAYER PROTEINS FOR EXPRESSION OF HETEROLOGOUS PROTEINS

RELATED APPLICATIONS

This application is a national phase application claiming benefit of priority under 35 U.S.C. § 371 to Patent Convention Treaty (PCT) International Application serial number PCT/US2018/048576, filed Aug. 29, 2018, now pending, which claims the benefit of priority to U.S. Provisional Patent Application Ser. No. 62/551,502, filed Aug. 29, 2017, and U.S. Ser. No. 62/551,490, filed Aug. 29, 2017. The aforementioned applications are expressly incorporated herein by reference in their entirety and for all purposes.

TECHNICAL FIELD

This invention generally relates to microbiology and bioengineering. In alternative embodiments, provided are compositions and methods for making a chimeric polypeptide comprising an S-layer polypeptide and a heterologous polypeptide or peptide. In alternative embodiments, the compositions and methods comprise recombinantly engineering a methylotrophic or methanotrophic bacteria to recombinantly express a chimeric polypeptide comprising an S-layer polypeptide and a heterologous polypeptide or peptide. Also provided are compositions and methods for displaying or immobilizing proteins on a methanotrophic S-layer. In alternative embodiments, provided are compositions and methods using recombinant methylotrophic or methanotrophic bacteria, optionally a *Methylomicrobium alcaliphilum* (*M. alcaliphilum*), optionally a *M. alcaliphilum* sp. 20Z, for ectoine ((4S)-2-methyl-1,4,5,6-tetrahydropyrimidine-4-carboxylic acid), for the production or synthesis of a protein, e.g., an ectoine, or an enzyme, e.g., a lipase.

BACKGROUND

Bacterial cell surface layers are regular para-crystalline structures that cover the entire surface of a cell and consist of a single layer of identical proteins or glycoproteins. These glycoproteins are potentially of industrial interest because they intrinsically self-assemble and re-crystallise to form porous semi-permeable membranes. These characteristics, and subsequent functionalisation of surfaces, has led to new types of ultrafiltration membranes, affinity structures, enzyme membranes, micro-carriers, biosensors, diagnostic devices, biocompatible surfaces and vaccines, as well as targeting, delivery, and encapsulation.

Methylotrophic and methanotrophic bacteria have been used as systems for the heterologous expression of proteins, see e.g., US 2010 0221813 A1 (2010). However, most attempts to improve protein expression have been focused on intracellular protein expression.

An S-layer, or surface layer, a part of a cell envelope found in almost all archaea and in many types of bacteria, consists of a monomolecular layer composed of identical proteins or glycoproteins. For many bacteria, the S-layer represents the outermost interaction zone with their respective environments, and it can have many different functions depending on the species, for example an S-layer can have a mechanical and osmotic stabilization function, can protect against bacteriophages or phagocytosis, can provide resistance against low pH, can act as a barrier against high-molecular-weight substances, can act as a molecular sieve and barrier, can have anti-fouling properties, be involved in biomineralization, and the like.

S-Layers are present at the surfaces of methylotrophic and methanotrophic cells such as *Methylococcus, Methylothermus*, and *Methylomicrobium* bacterial cells. For example, different *Methylomicrobium* species can synthesize S-layers with planar (p2, p4) symmetry or form cup-shaped or conical structures with hexagonal (p6) symmetry. S-layers are a well-recognized microbial product with very broad biotechnological applications. Numerous research activities are focused on the construction of fusion proteins (S-layer proteins with attached enzymes) for production of immobilized biocatalysts. Formation of S-layers has been observed in all tested *Methylomicrobium* species. *M. album* BG8, *M. alcaliphilum* 20Z and *M. buyatense* form S-layers consisting of cup-shaped subunits arranged in p6 symmetry. Methanotrophic S-layers have been mentioned as a potential value-added product, but were not explored much due to the lack of knowledge on its genetic elements.

The use of an aerobic methane-oxidation process for methane reduction in coal mines has been actively discussed for decades and even tested in the 1980s. The approach was very simple: different methanotrophic cultures were sprayed on coal mine surfaces and methane consumption was monitored. The study indicated a potential for the methanotroph-based technology, however, no active "industrial strain" was identified and no profitable process was developed.

SUMMARY

In alternative embodiments, provided are methods for making a chimeric polypeptide comprising an S-layer polypeptide, or self-assembling or self-aggregating fragments thereof, and a heterologous polypeptide or peptide, the method comprising recombinantly engineering a methylotrophic or methanotrophic bacteria to recombinantly express a chimeric polypeptide comprising an S-layer polypeptide or a self-assembling fragment thereof and a heterologous polypeptide or peptide, wherein optionally the recombinant or isolated chimeric polypeptide or self-assembling or self-aggregating fragment thereof has assembled or is self-assembled to form a monomolecular layer, and optionally the S-layer polypeptide or self-assembling fragment thereof is on the carboxy terminal end of the heterologous polypeptide or peptide, and optionally the S-layer polypeptide or self-assembling fragment thereof comprises an S-layer polypeptide endogenous to the methylotrophic or methanotrophic bacteria, or comprises an S-layer polypeptide from another methylotrophic or methanotrophic bacteria or from another bacteria, In alternative embodiments, provided are methods for displaying or immobilizing proteins on a methanotrophic S-layer comprising recombinantly engineering a methylotrophic or methanotrophic bacteria to recombinantly express a chimeric polypeptide comprising an S-layer polypeptide or a self-assembling fragment thereof and a heterologous polypeptide or peptide, wherein optionally the recombinant or isolated chimeric S-layer polypeptide (or self-assembling or self-aggregating fragment thereof) has assembled or is self-assembled to form a monomolecular layer, and optionally the S-layer polypeptide or self-assembling fragment thereof is on the carboxy terminal end of the heterologous polypeptide or peptide, and optionally the S-layer polypeptide or self-assembling fragment thereof comprises an S-layer polypeptide endogenous to the methylotrophic or methanotrophic bacteria, or comprises an S-layer polypeptide or self-assembling or self-aggregating fragment thereof from another methylotrophic or methanotrophic bacteria or from another bacteria.

In alternative embodiments, provided are recombinant or isolated chimeric S-layer polypeptides, wherein the recombinant or isolated chimeric S-layer polypeptide comprises an S-layer polypeptide or self-assembling or self-aggregating fragment thereof and a heterologous polypeptide or peptide, wherein optionally the recombinant or isolated chimeric S-layer polypeptide has assembled or is self-assembled to form a monomolecular layer, and optionally the S-layer polypeptide or self-assembling or self-aggregating fragment thereof is on the carboxy terminal end of the heterologous polypeptide or peptide, and optionally the S-layer polypeptide or self-assembling or self-aggregating fragment thereof comprises an S-layer polypeptide endogenous to the methylotrophic or methanotrophic bacteria, or comprises an S-layer polypeptide or self-assembling or self-aggregating fragment thereof from another methylotrophic or methanotrophic bacteria or from another bacteria.

In alternative embodiments, provided are recombinant or isolated monomolecular layers comprising a plurality of chimeric S-layer polypeptides, wherein the plurality of recombinant or isolated chimeric S-layer polypeptides comprise an S-layer polypeptide or self-assembling fragment thereof and a heterologous polypeptide or peptide, wherein optionally the plurality of recombinant or isolated chimeric S-layer polypeptide has assembled or is self-assembled to form a monomolecular layer, and optionally the S-layer polypeptide or self-assembling or self-aggregating fragment thereof is on the carboxy terminal end of the heterologous polypeptide or peptide, and optionally the S-layer polypeptide comprises an S-layer polypeptide or self-assembling or self-aggregating fragment thereof endogenous to the methylotrophic or methanotrophic bacteria, or comprises an S-layer polypeptide or self-assembling or self-aggregating fragment thereof from another methylotrophic or methanotrophic bacteria or from another bacteria.

In alternative embodiments, provided are engineered or recombinant methylotrophic or methanotrophic bacteria comprising the recombinant or isolated chimeric S-layer polypeptide as provided herein, or comprising a recombinant or chimeric polypeptide made by the method as provided herein, wherein optionally the S-layer polypeptide or self-assembling or self-aggregating fragment thereof comprises an S-layer polypeptide endogenous to the methylotrophic or methanotrophic bacteria, or comprises an S-layer polypeptide or self-assembling or self-aggregating fragment thereof from another methylotrophic or methanotrophic bacteria or from another bacteria.

In alternative embodiments, provided are recombinant or chimeric polypeptides assembled or self-assembled to form a monomolecular layer on the extracellular surface of the recombinant methylotrophic or methanotrophic bacteria, and optionally the heterologous polypeptide or peptide is at least partially exposed, or is fully exposed, to an extracellular environment or milieu, and optionally the S-layer polypeptide or self-assembling or self-aggregating fragment thereof is on the carboxy terminal end of the heterologous polypeptide or peptide.

In alternative embodiments of the methods or the recombinant or isolated chimeric S-layer polypeptides as provided herein, the S-layer polypeptide or self-assembling or self-aggregating fragment thereof (or the finally post-translationally processed S-layer polypeptide) comprises or is a lipoprotein, and optionally the S-layer polypeptide comprises an S-layer polypeptide endogenous to the methylotrophic or methanotrophic bacteria, or comprises an S-layer polypeptide from another methylotrophic or methanotrophic bacteria or from another bacteria.

In alternative embodiments of the methods or the recombinant or isolated chimeric S-layer polypeptides as provided herein, the methylotrophic or methanotrophic bacteria is selected the group consisting of a *Methylococcus*, a *Methylomonas*, a *Methylomicrobium*, a *Methylobacter*, a *Methylomarinum*, a *Methylovulum*, a *Methylocaldum*, a *Methylothermus*, a *Methylomarinovum*, a *Methylosphaera*, a *Methylocystis*, and a *Methylosinus* bacteria, for example, in alternative embodiments the S-layer polypeptide is derived from a *Methylococcus*, a *Methylomonas*, a *Methylomicrobium*, a *Methylobacter*, a *Methylomarinum*, a *Methylovulum*, a *Methylocaldum*, a *Methylothermus*, a *Methylomarinovum*, a *Methylosphaera*, a *Methylocystis*, and a *Methylosinus* bacteria.

In alternative embodiments of the methods or the recombinant or isolated chimeric S-layer polypeptides as provided herein, wherein the methylotrophic or methanotrophic bacteria is a *Methylomicrobium alcaliphilum* (*M. alcaliphilum*), or a *M. alcaliphilum* sp. 20Z, for example, in alternative embodiments the S-layer polypeptide is derived from a *Methylomicrobium alcaliphilum* (*M. alcaliphilum*), or a *M. alcaliphilum* sp. 20Z.

In alternative embodiments of the methods or the recombinant or isolated chimeric S-layer polypeptides as provided herein, the chimeric polypeptide, or the recombinant or isolated chimeric S-layer polypeptide, is expressed on the surface of a methylotrophic or methanotrophic bacteria, and the heterologous polypeptide, or the recombinant or isolated chimeric S-layer polypeptide, or S-layer polypeptide or self-assembling or self-aggregating fragment thereof, is at least in part exposed to an extracellular environment or milieu.

In alternative embodiments of the methods or the recombinant or isolated chimeric S-layer polypeptides as provided herein, the methanotrophic S-layer polypeptide or self-assembling or self-aggregating fragment thereof is isolated or is derived from the methylotrophic or methanotrophic bacteria.

In alternative embodiments of the methods or the recombinant or isolated chimeric S-layer polypeptides as provided herein, the heterologous polypeptide or peptide, or recombinant or isolated chimeric S-layer polypeptide, comprises or further comprises: an enzyme, a structural protein, a fluorescent or a chemiluminescent protein, a ligand, a receptor, an antibody or antigen binding protein, or an antigen, a tolerogen or an immunogen.

In alternative embodiments of the methods or the recombinant or isolated chimeric S-layer polypeptides as provided herein, the enzyme is an industrial enzyme, or the enzyme is a lipase, a protease, a nitrogenase, a hydrogenase, a monooxygenase, an amylase, an isomerase, a cellulase or hemicellulase, a laccase, an epimerase, a decarboxylase, a glucanase or a fl-glucanase, a glucosidase, a phosphorylase, a phosphatase, a halogenase or a dehalogenase, a GlcNAc transferase, an N-acetylglucosamine, a GlcNAc transferase, a neuraminidase or sialidase, a nuclease, a peroxidase or an oxidase, or a metalloproteinase.

In alternative embodiments of the methods or the recombinant or isolated chimeric S-layer polypeptides as provided herein, the chimeric protein, the recombinant or isolated chimeric S-layer polypeptide or self-assembling or self-aggregating fragment thereof, the recombinant or isolated monomolecular layer, or the recombinant methylotrophic or methanotrophic bacteria, act as or are used as or used for: an ultrafiltration membrane; an affinity structure; nitrogen fixation; converting carbon dioxide into methane; methane uptake or methane oxidation; converting nitrogen gas to ammonia; a membrane of an enzyme membrane; a micro-carrier; a biosensor; a diagnostic device; a biocompatible surface; a vaccine; a device or composition for targeting, delivery and/or encapsulation; an anchor for extracellular production of a small molecule or a protein (optionally an enzyme or a structural protein), an enzymatic system for a bioremediation or a bio-mitigation, or a pharmaceutical or a protein-based biopharmaceutical.

In alternative embodiments, provided herein are membranes or an enzyme membrane; an ultrafiltration membrane; an affinity structure; a composition or device for nitrogen fixation; a composition or device for converting carbon dioxide into methane; a composition or device for methane uptake or methane oxidation; a composition or device for converting nitrogen gas to ammonia; a membrane of an enzyme membrane; a micro-carrier; a biosensor; a diagnostic device; a biocompatible surface; a vaccine; a device or composition for targeting, delivery and/or encapsulation; an implant; an anchor for extracellular production of a small molecule or a protein (optionally an enzyme or a structural protein), an enzymatic system for a bioremediation or a bio-mitigation, or a pharmaceutical or a protein-based biopharmaceutical, comprising:
  a chimeric polypeptide as provided herein,
  a recombinant or isolated chimeric S-layer polypeptide or self-assembling or self-aggregating fragment thereof as provided herein,
  a recombinant or isolated monomolecular layer as provided herein, or
  a recombinant methylotrophic or methanotrophic bacteria as provided herein.

In alternative embodiments, provided are recombinant or engineered methylotrophic or methanotrophic bacteria, optionally a *Methylomicrobium alcaliphilum* (*M. alcaliphilum*), optionally a *M. alcaliphilum* sp. 20Z, for ectoine ((4S)-2-methyl-1,4,5,6-tetrahydropyrimidine-4-carboxylic acid) production or synthesis, wherein:
  (a) the recombinant or engineered methylotrophic or methanotrophic bacteria comprises an ectoine biosynthetic gene cluster organized as one operon (ectABC-ask), wherein the operon comprises genes encoding: a diaminobutyric acid (DABA) aminotransferase (EctB); a DABA acetyltransferase (EctA), and an ectoine synthase (EctC); and
  (b) the recombinant or engineered methylotrophic or methanotrophic bacteria: (i) is engineered to lack or not express a functional EctR1 repressor; (ii) comprises an isocitrate lyase/malate synthase fusion under (transcriptionally controlled by) a hps promoter ($P_{hps}$); and/or, (iii) comprises one or more of the genetic modifications set forth in Table 1 (see Example 2, below).

In alternative embodiments of the recombinant or engineered methylotrophic or methanotrophic bacteria, a doeA-gene encoding ectoine hydrolase is deleted or mutated such that a functional ectoine hydrolase is not expressed.

In alternative embodiments, the recombinant or engineered methylotrophic or methanotrophic bacteria further comprises an exogenous nucleic acid capable of expressing a methanotrophic lipase, or a functional lipase fragment thereof (optionally a LipL1 expression plasmid), in the recombinant or engineered methylotrophic or methanotrophic bacteria.

In alternative embodiments, the recombinant or engineered bacteria is engineered such that the ectoine and/or the lipase, or the functional lipase fragment thereof, is expressed as an S layer protein chimeric polypeptide, optionally as a lipase-S protein fusion protein (an S layer-lipase or an S layer-ectoine fusion protein).

In alternative embodiments, the methylotrophic or methanotrophic bacteria is selected the group consisting of a *Methylococcus*, a *Methylomonas*, a *Methylomicrobium*, a *Methylobacter*, a *Methylomarinum*, a *Methylovulum*, a *Methylocaldum*, a *Methylothermus*, a *Methylomarinovum*, a *Methylosphaera*, a *Methylocystis*, and a *Methylosinus* bacteria, and optionally the S layer protein is derived from a *Methylococcus*, a *Methylomonas*, a *Methylomicrobium*, a *Methylobacter*, a *Methylomarinum*, a *Methylovulum*, a *Methylocaldum*, a *Methylothermus*, a *Methylomarinovum*, a *Methylosphaera*, a *Methylocystis*, or a *Methylosinus* bacteria, or optionally the S-layer polypeptide is derived from a *Methylomicrobium alcaliphilum* (*M. alcaliphilum*), or a *M. alcaliphilum* sp. 20Z. In alternative embodiments, the S-layer protein is endogenous to the methylotrophic or methanotrophic recombinant or engineered bacteria.

In alternative embodiments, the methylotrophic or methanotrophic bacteria further comprise the ability to express a heterologous or exogenous protein or enzyme, optionally an industrial enzyme; or the S layer protein chimeric polypeptide comprises a protein or an enzyme, optionally an industrial enzyme. In alternative embodiments, the enzyme is a lipase, a protease, a nitrogenase, a hydrogenase, a monooxygenase, an amylase, an isomerase, a cellulase or hemicellulase, a laccase, an epimerase, a decarboxylase, a glucanase or a fl-glucanase, a glucosidase, a phosphorylase, a phosphatase, a halogenase or a dehalogenase, a GlcNAc transferase, an N-acetylglucosamine, a GlcNAc transferase, a neuraminidase or sialidase, a nuclease, a peroxidase or an oxidase, or a metalloproteinase.

In alternative embodiments, the recombinant or engineered methylotrophic or methanotrophic bacteria, or the S layer protein chimeric polypeptide produced by the recombinant or engineered methylotrophic or methanotrophic bacteria, act as or are used as or used for: an ultrafiltration membrane; an affinity structure; nitrogen fixation; converting carbon dioxide into methane; methane uptake or methane oxidation; converting nitrogen gas to ammonia; a membrane of an enzyme membrane; a micro-carrier; a biosensor; a diagnostic device; a biocompatible surface; a vaccine; a device or composition for targeting, delivery and/or encapsulation; an anchor for extracellular production of a small molecule or a protein (optionally an enzyme or a structural protein), an enzymatic system for a bioremediation or a bio-mitigation, or a pharmaceutical or a protein-based biopharmaceutical.

In alternative embodiments, provided are: a membrane or an enzyme membrane; an ultrafiltration membrane; an affinity structure; a composition or device for nitrogen fixation; a composition or device for converting carbon dioxide into methane; a composition or device for methane uptake or methane oxidation; a composition or device for converting nitrogen gas to ammonia; a membrane of an enzyme membrane; a micro-carrier; a biosensor; a diagnostic device; a biocompatible surface; a vaccine; a device or composition for targeting, delivery and/or encapsulation; an implant; an anchor for extracellular production of a small molecule or a protein (optionally an enzyme or a structural protein), an enzymatic system for a bioremediation or a bio-mitigation, or a pharmaceutical or a protein-based biopharmaceutical, comprising:
  a chimeric polypeptide made by a method (or by a recombinant or engineered methylotrophic or methanotrophic bacteria) as provided herein, a recombinant or isolated chimeric S-layer polypeptide made by a method (or by a recombinant or engineered methylotrophic or methanotrophic bacteria) as provided herein, a recombinant or isolated monomolecular layer made by a method (or by a recombinant or engineered methylotrophic or methanotrophic bacteria) as provided herein, or a recombinant or engineered methylotrophic or methanotrophic bacteria made by a method as provided herein.

The details of one or more embodiments as provided herein are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments as provided herein and are not meant to limit the scope of the invention as encompassed by the claims.

FIG. 1A illustrates an image of in vivo activity, or intracellular production, of a lipase gene cloned into an expression vector and introduced into *Methylomicrobium* sp. AP18, as detected on rhodamine B-containing plates;

FIG. 1B illustrates an image of a Coumassie-stained polyacrylamide gel (PAAG) showing that a lipase gene expression vector showed low levels of lipase expression, e.g., the protein was not visible in lane 5; and an optimized vector with a ribosome binding site (RBS) resulted in clones with significantly higher expression, with the recombinant lipase comprising of about 1% to 2% of total cell protein, see lanes 6 to 12, as described in detail in Example 1, below.

FIG. 2A, schematically illustrates in upper and lower images a lipase enzyme-encoding nucleic acid construct, and a plasmid containing this genetic construct, respectively;

FIG. 2B schematically illustrates how this genetic construct is transferred from *E. coli* S17-1 by conjugation and plasmid transfer into an *M. alcaliphilum* 20Z strain, followed by recombination and incorporation of the fused gene (the genetic construct) into the chromosome, resulting in expression and export of the fusion protein, as described in detail in Example 1, below.

FIG. 4A-C: FIG. 4A graphically illustrates data showing the growth of *M. alcaliphilum* 20ZR in a DASBOX™ mini bioreactor, as batch and chemostat mode; FIG. 4B-C graphically illustrate $O_2$ and $CH_4$ consumptions and $CO_2$ production in steady-state for bioreactor replicate 1 (FIG. 4B) and bioreactor replicate 2 (FIG. 4C), as described in detail in Example 2, below.

FIG. 5A illustrates a chromatogram of 1 mM ectoine solution, and FIG. 5B illustrates a chromatogram of 20ZR cell extract, as described in detail in Example 2, below.

FIG. 9A illustrates HPLC analysis of HPLC analysis of $20Z::P_{SL}$-L1$\Delta$ectR (in batch culture); and, FIG. 9B illustrates $20Z^R P_{SL}$-L1$\Delta$ectR $\Delta$doeA strain (in batch culture), as described in detail in Example 2, below.

FIG. 10A-C illustrate data from the cultivation of TWC #G2-3 as performed in a DASBOX™ mini bioreactor, and collected data is shown as: FIG. 10A graphically illustrates growth of *M. alcaliphilum* $20Z^R P_{SL}$-L1$\Delta$ectR$\Delta$doeA as batch and chemostat mode; FIG. 10B-C graphically illustrate $O_2$ and $CH_4$ consumptions and $CO_2$ production in steady-state for bioreactor replicate 1 (FIG. 10B) and bioreactor replicate 2 (FIG. 10C), as described in detail in Example 2, below.

FIG. 11 illustrates LipL1 preparations, as described in detail in Example 2, below.

FIG. 15 left: LipL locus, indicating that LipL-MxeGyrA- was incorporated into the genome; FIG. 15 right: LipL-S-layer locus from showing that LipL gene was incorporated in correct orientation, as LipL-MxeGyrA-S-layer, as described in detail in Example 3, below.

FIG. 16A-B illustrate *M. alcaliphilum* 20ZR wild type (FIG. 16A, phase; FIG. 16B, GFP ex450-490 nm; em 500-550 nm); FIG. 16C, 20ZR::GFP-300Cter$_{SLP}$; FIG. 16D, GFP-100Cter$_{SLP}$; FIG. 16E, GFP-12Cter$_{SLP}$, as described in detail in Example 3, below.

Like reference symbols in the various drawings indicate like elements.

Figure 1B:
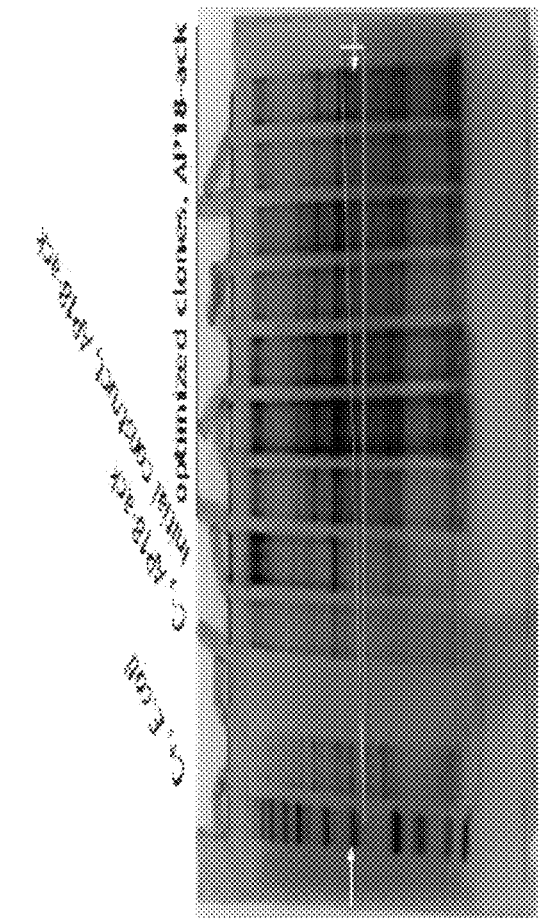
FIG. 1A-B illustrate Lipase production in methanotrophic cultures.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

Chimeric Polypeptides Comprising an S-Layer Polypeptide, or Self-Assembling or Self-Aggregating Fragments Thereof, and a Heterologous Polypeptide or Peptide In alternative embodiments, provided are compositions and methods for making a chimeric polypeptide comprising an S-layer polypeptide, or self-assembling or self-aggregating fragments thereof, and a heterologous polypeptide or peptide. In alternative embodiments, the compositions and methods comprise recombinantly engineering a methylotrophic or methanotrophic bacteria to recombinantly express a chimeric polypeptide comprising an S-layer polypeptide, or self-assembling or self-aggregating fragments thereof, and a heterologous polypeptide or peptide. In alternative embodiments, the S-layer polypeptide, or self-assembling or self-aggregating fragments thereof, is engineered to be amino terminal to, internal to, or carboxy terminal to, the heterologous polypeptide or peptide.

Also provided are compositions and methods for displaying or immobilizing proteins on a methanotrophic S-layer. In alternative embodiments, provided are compositions and methods comprising a recombinant or isolated chimeric S-layer polypeptide, wherein the recombinant or isolated chimeric S-layer polypeptide comprises an S-layer polypeptide, or self-assembling or self-aggregating fragments thereof, and a heterologous polypeptide or peptide. In alternative embodiments, the S-layer polypeptide, or self-assembling fragments or self-aggregating thereof, is engineered to be amino terminal to, internal to, or carboxy terminal to, the heterologous polypeptide or peptide.

Also provided are recombinant or isolated monomolecular layers comprising a chimeric S-layer polypeptide, where the S-layer polypeptide can be a self-assembling or self-aggregating fragment thereof. In alternative embodiments, provided are compositions and methods comprising recombinant methylotrophic or methanotrophic bacteria comprising assembled or self-assembled recombinant or isolated chimeric S-layer polypeptides. In alternative embodiments, the S-layer polypeptides, or self-assembling or self-aggregating fragments thereof, are lipoproteins, for example, the S-layer polypeptides can be lipoproteins as post-translationally modified.

Provided herein for the first time are applications of bacterial extracellular methanotrophic S-layer proteins, or self-assembling or self-aggregating fragments thereof, for the expression of heterologous proteins, including extracellular expression of a heterologous protein on the surface of a methanotrophic S-layer protein-expressing bacteria. In alternative embodiments, methanotrophic S-layers, either isolated (e.g., as described in Khmelenina V N, et al (1999) Arch. Microbiol. 172: 321-329) or as surface-expressed methanotrophic S-layers, are used as an anchor or expression vehicle for the extracellular production, expression and use of proteins, e.g., enzymes such as industrial enzymes, e.g. proteinases, lipases, amylases, celluloses, fl-glucanase, as well as for their use as enzymatic systems for bioremediation and bio-mitigations, e.g. dehalogenases and peroxidases, and protein-based biopharmaceuticals.

We identified the gene encoding the major S-layer protein in *M. alcaliphilum* sp. 20Z using quantitative proteomics on purified S-layer preparations. The S-layer protein appears to be the main cellular protein, comprising up to 20% of total cellular protein. Provided herein are recombinant S-layers and uses of recombinant S-layers as an efficient chimeric polypeptide or cellular system for use as an ultrafiltration membrane; an affinity structure; a membrane of an enzyme membrane; a micro-carrier, a biosensor; a diagnostic device, a biocompatible surface, a vaccine, a device or composition for targeting, delivery and/or encapsulation; an anchor for extracellular production of a small molecule or a protein (optionally an enzyme or a structural protein), an enzymatic system for a bioremediation or a bio-mitigation, or a pharmaceutical or a protein-based biopharmaceutical In alternative embodiments of compositions and methods as provided herein, chimeric proteins are delivered and expressed outside of the bacterial cell, e.g., chimeric proteins as provided herein are expressed extracellularly can be completely or partially exposed to an extracellular milieu. In alternative embodiments, systems as provided herein are also used to produce enzymatic or structural membranes.

We developed a protocol for genetic alterations of the S-layers for heterologous expression of proteins on a bacterial cell surface. Overview of the approach is shown in FIG. 2.

S-Layer Polypeptides, or Self-Assembling or Self-Aggregating Fragments Thereof

Exemplary S-layer polypeptides, or self-assembling or self-aggregating fragments thereof, can comprise or consist of:

```
                                            SEQ ID NO: 8
GANNQVAALQTAAGGAFDGTFFDVLSNFTVEASFEVLSQFDPETTLFVANP

IVEDVNFDIVRDVNGDVTSVSVSGGSSLGFAQSDAGFQELLEAGQVTEVVF

ENVGSLNSILVSGNFVGSYDAGGIFYESTFEFGANAGSVAEGVGTDGNIFT

IAEFTAGAAASDILDFTAMPVDNTNTAPATGHEFIAVGTEASIGDDATIIV

FTAGVAADAATIVTQFADGAGDFRSADATARNADFAIDSQLIFLIDDGAGN

TGVWYWDDTVGAVGDGIVDADELSQIAQLTGVVTAELTVDNFVLA,

SEQ ID NO: 9
TIIVFTAGVAADAATIVTQFADGAGDFRSADATARNADFAIDSQLIFLIDD

GAGNTGVWYWDDTVGAVGDGIVDADELSQIAQLTGVVTAELTVDNFVLA,

SEQ ID NO: 10
AGNTGVWYWDDTVGAVGDGIVDADELSQIAQLTGVVTAELTVDNFVLA,

SEQ ID NO: 11
VGAVGDGIVDADELSQIAQLTGVVTAELTVDNFVLA,

SEQ ID NO: 12
TAELTVDNFVLA,
or
the S-layer polypeptide as encoded by the nucleic
acid sequence of SEQ ID NO: 5, SEQ ID NO: 7 and/or
SEQ ID NO: 7, as indicated below.
```

Exemplary S-layer polypeptide self-assembling or self-aggregating fragments thereof also can comprise or consist of any self-assembling fragment, which can be readily identified by routine screening of an S-layer polypeptide.

Exemplary S-layer polypeptides or self-assembling or self-aggregating fragments thereof also comprise S-layer polypeptide sequences as described herein but comprising at least one amino acid residue conservative substitution, wherein optionally the at least one conservative substitution comprises replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or, replacement of an aromatic residue with another aromatic residue, or a combination thereof, and optionally the aliphatic residue comprises Alanine, Valine, Leucine, Isoleucine or a synthetic equivalent thereof, the acidic residue comprises Aspartic acid, Glutamic acid or a synthetic equivalent thereof; the residue comprising an amide group comprises Aspartic acid, Glutamic acid or a synthetic equivalent thereof, the basic residue comprises Lysine, Arginine or a synthetic equivalent thereof, or, the aromatic residue comprises Phenylalanine, Tyrosine or a synthetic equivalent thereof.

Recombinant Methylotrophic or Methanotrophic Bacteria to Express Heterologous Proteins In alternative embodiments, provided are compositions and methods using recombinant methylotrophic or methanotrophic bacteria, optionally a *Methylomicrobium alcaliphilum* (*M. alcaliphilum*), optionally a *M. alcaliphilum* sp. 20Z, for ectoine ((4S)-2-methyl-1,4,5,6-tetrahydropyrimidine-4-carboxylic acid), for the production or synthesis of a protein, e.g., an ectoine (1,4,5,6-tetrahydro-2-methyl-4-pyrimidinecarboxylic acid), or an enzyme, e.g., a lipase.

Provided herein are new mitigation strategies for effective conversion of atmospheric greenhouse gases (e.g., $CO_2$ or methane) to next generation chemicals which are a new technology for the reduction/stabilization of global warming. In alternative embodiments, provided are new biological processes for efficient utilization of methane, e.g., coalmine methane, and also optionally comprising the simultaneous production of e.g., amino acids; osmo-protecting, moisturizing and hydrating agents; and, industrial and/or digestive enzymes. In alternative embodiments, these processes provide both environmental (reduction of the global warming impact) and economical (production of value-added compounds) benefits. In alternative embodiments, provided are:

i) Recombinant or engineered obligate methane-oxidizing bacteria (methanotrophs) and methanotrophic catalysts to enhance ectoine production capabilities in the cells;

ii) novel genetically altered obligate methane-oxidizing bacteria (methanotrophs) and methanotrophic catalysts that produce a lipase or an ectoine;

iii) uses of stranded methane emissions, such as abandoned coal mines, to "feed" recombinant obligate methane-oxidizing bacteria (methanotrophs) as provided herein methane (to provide methane as a carbon source) for e.g., methane uptake or methane oxidation.

In alternative embodiments, methods provided herein comprise use of biological systems (microbial cells, including recombinant obligate methane-oxidizing bacteria (methanotrophs), or enzymes as provided herein) as catalysts for conversion of atmospheric greenhouse gases (e.g., $CO_2$ or methane). In alternative embodiment, methods provided herein comprise use of obligate methane-oxidizing bacteria (methanotrophs), which are a highly-specialized group of bacteria utilizing methane ($CH_4$) as a sole source of carbon and energy. Methanotrophs are ubiquitously distributed in nature and play an important role in global carbon cycling. Also, these organisms are of great importance for global warming because they reduce $CH_4$ emissions from natural ecosystems. In alternative embodiment, methods provided herein comprise use of methanotrophs, including recombinant obligate methane-oxidizing bacteria (methanotrophs), for the commercial production of both bulk and fine chemicals and bioremediation of hazardous pollutants such as halogenated methanes and trichloroethylene (TCE).

In alternative embodiment, methods provided herein comprise use of recombinant or engineered aerobic methanotrophic bacteria for controlling/monitoring methane emissions from methane-producing zones such as coal mining, feedlots, etc. In alternative embodiment, methods provided herein are a bacteria-based methane reduction technology that can be cost effective and can be combined with synthesis of valuable commercial products, such as biomass, amino acids, vitamins, and alternative fuels and chemicals.

In alternative embodiments, provided are engineered biological processes, and compositions and methods for practicing same, for the reduction of the methane content in defined space, e.g., a coal mine or industrial (e.g., factory) environment. These embodiments provide environmental (e.g., reduction of the global warming impact), safety and economical (e.g., production of value-added compounds) benefits. In alternative embodiments, provided is a microbial catalyst for efficient utilization of coal mine methane and, optionally, also for the simultaneous production of ectoine and/or lipase.

In alternative embodiments, compositions and methods as provided herein, including recombinant obligate methane-oxidizing bacteria (methanotrophs) as provided herein, use microbial catalysts to enhance ectoine production capabilities up to 10% cell dry weight (CDW). In alternative embodiments, provided are methods for the construction of a novel genetically altered microbial catalyst producing lipase, optionally up to 10% of CDW. Also provided is the testing of conditions relevant to small scale, mobile, field applications at sites of stranded methane emissions, such as abandoned coal mines and identification of lab-scale cultivation parameters suitable for implementation of the proposed technology on site.

Methanotrophic S-Layers and S-Layer-Based Enzyme Immobilization

In alternative embodiments, compositions and methods as provided herein use S-layers, which are a well-recognized microbial product with very broad biotechnological applications, see e.g., Egelseer et al., 2009, NanoBioTechnology (Shoseyov O & Levy I, eds), pp. 55-86. Humana Press, Totowa, N.J.; or Egelseer et al., The Encyclopedia of Industrial Biotechnology: Bioprocess, Bioseparation, and Cell Technology, Vol. 7 (Flickinger M C, ed.), pp. 4424-4448. John Wiley & Sons, Inc., Hoboken, N.J. In alternative embodiments, compositions and methods as provided herein comprise the construction of fusion proteins comprising S-layer proteins with attached enzymes (or other proteins) for the production of immobilized biocatalysts. In alternative embodiments, S-layers derived from *Methylomicrobium* species are used, including *M. album* BG8, *M. alcaliphilum* 20Z and *M. buryatense*. Formation of S-layers has been observed in all tested *Methylomicrobium* species. *M. album* BG8, *M. alcaliphilum* 20Z and *M. buryatense* form S-layers consisting of cup-shaped subunits arranged in p6 symmetry [Jeffries and Wilkinson 1978, Khmelenina et al., 1999]. In alternative embodiments, S-layer proteins are positioned carboxy terminal to the attached protein, although they can also be internal or amino terminus positioned.

We identified the gene encoding the major S-layer protein in *M. alcaliphilum* sp. 20Z using quantitative proteomics on purified S-layer preparations; see Example 2, below. The S-layer protein appears to be the main cellular protein, comprising up to 20% of total cellular protein. In alternative embodiments, compositions and methods as provided herein use S-layers as an efficient cellular system to deliver proteins outside of the cell. In alternative embodiments, this system is also used to produce biological filters or purification systems, and enzymatic membranes.

Generating and Manipulating Nucleic Acids

In alternative embodiments, nucleic acids used to practice methods as provided herein, or to make compositions or recombinant bacteria as provided herein, are made, isolated and/or manipulated by, e.g., cloning and expression of cDNA libraries, amplification of message or genomic DNA by PCR, and the like. The nucleic acids and genes used to practice this invention, including DNA, RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides generated from these nucleic acids can be individually isolated or cloned and tested for a desired activity. Any recombinant expression system or gene therapy delivery vehicle can be used, including e.g., viral (e.g., AAV constructs or hybrids) bacterial, fungal, mammalian, yeast, insect or plant cell expression systems or expression vehicles.

Alternatively, nucleic acids used to practice methods as provided herein, or to make compositions or recombinant bacteria as provided herein, can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids used to practice methods as provided herein, or to make compositions or recombinant bacteria as provided herein, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice methods as provided herein, or to make compositions or recombinant bacteria as provided herein, is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In alternative embodiments, a heterologous peptide or polypeptide joined or fused to a protein made by a method or a recombinant bacteria as provided herein can be an N-terminal identification peptide which imparts a desired characteristic, such as fluorescent detection, increased stability and/or simplified purification. Peptides and polypeptides made by a method or a recombinant bacteria as provided herein can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Nucleic acids or nucleic acid sequences used to practice embodiments as provided herein can be an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. Compounds use to practice this invention include "nucleic acids" or "nucleic acid sequences" including oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., e.g., double stranded iRNAs, e.g., iRNPs). Nucleic acids or nucleic acid sequences used to practice embodiments as provided herein include nucleic acids or oligonucleotides containing known analogues of natural nucleotides. Nucleic acids or nucleic acid sequences used to practice embodiments as provided herein include nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. Nucleic acids or nucleic acid sequences used to practice embodiments as provided herein include "oligonucleotides" including a single stranded polydeoxynucleotide or two complementary polydeoxynucleotide strands that may be chemically synthesized. Compounds use to practice this invention include synthetic oligonucleotides having no 5' phosphate, and thus will not ligate to another oligonucleotide without adding a phosphate with an ATP in the presence of a kinase. A synthetic oligonucleotide can ligate to a fragment that has not been dephosphorylated.

In alternative aspects, methods and recombinant bacteria as provided herein comprise use of "expression cassettes" comprising a nucleotide sequences capable of affecting expression of the nucleic acid, e.g., a structural gene or a transcript (e.g., encoding an S-layer protein, and/or an enzyme such as a lipase or a ectoine) in a host compatible with such sequences, such as e.g., methylotrophic and methanotrophic cells such as *Methylococcus, Methylothermus,* and *Methylomicrobium* bacterial cells. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes used to practice embodiments as provided herein also include plasmids, expression vectors, recombinant viruses, any form of recombinant "naked DNA" vector, and the like. In alternative aspects, a "vector" used to practice embodiments as provided herein can comprise a nucleic acid that can infect, transfect, transiently or permanently transduce a cell. In alternative aspects, a vector used to practice embodiments as provided herein can be a naked nucleic acid, or a nucleic acid complexed with protein or lipid. In alternative aspects, vectors used to practice embodiments as provided herein can comprise viral or bacterial nucleic acids and/or proteins, and/or membranes (e.g., a cell membrane, a viral lipid envelope, etc.). In alternative aspects, vectors used to practice embodiments as provided herein can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, the vector used to practice embodiments as provided herein can be stably replicated by the cells during mitosis as an autonomous structure, or can be incorporated within the host's genome.

In alternative aspects, "promoters" used to practice this invention include all sequences capable of driving transcription of a coding sequence in a bacterial cell, e.g., a methylotrophic or methanotrophic bacterial cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

Bacterial Growth Conditions

Any set of known growth conditions can be used to practice embodiments as provided herein, for example, as described in US 2016-0237398 A1, or WO/2015/058179; exemplary growth conditions and parameters are described in Example 1 and Example 2, below. Any known growth conditions for culturing methylotrophic and methanotrophic cells such as *Methylococcus, Methylothermus,* and *Methylomicrobium* bacterial cells can be used.

The invention will be further described with reference to the following examples; however, it is to be understood that the invention is not limited to such examples.

EXAMPLES

Example 1: Exemplary Methods and Compositions

This example provides exemplary methods for making compositions and bacterial cells as provided herein.

Methanotrophic Strain Best Suited for Biotechnological Exploration.

Two methanotrophic cultures were established as the most promising industrial strains: *Methylomicrobium alcaliphilum* sp. 20Z and *Methylomicrobium buryatenses* 5G (see, e.g., Ojala et al., 2011; Kalyuzhnaya et al., 2015; Puri et al., 2015; Strong et al., 2016). While *M. buryatenses* 5G represents a fast-growing methanotroph (Td=3 h), *M. alcaliphilum* sp. 20Z was found to be more stable at high-cell density. Furthermore, the latter strain has a greater potential for accumulation of extractable products (ectoine, glutamate, sucrose). Based on those characteristics, *M. alcaliphilum* sp. 20Z was selected.

Genomes of both *M. alcaliphilum* sp. 20Z and *M. buryatenses* 5G were sequenced (see e.g., Vuilleumier et al., 2012). Genetic tools for efficient metabolic engineering of the strains were developed or optimized (see e.g., Ojala et al., 2011; Puri 2015; Henard et al., 2016). The current toolbox includes: vectors for gene knockouts (incorporated via bi-parental mating or electroporation); vectors for heterologous expression with low, intermediate and high levels of expression; and vectors with tunable promoters. Provided is a whole-genome reconstruction of the *M. alcaliphilum* sp. 20Z metabolic network, which is refined via metabolomics on cells grown in liquid culture, providing a computation framework for additional optimization of metabolic pathways in producing traits.

Methanotrophic S-Layers an S-Layer-Based Enzyme Immobilization

Here we describe use of S-layers as an efficient cellular system to deliver proteins outside of the cell. In alternative embodiments, this system is also used to produce biological filters and enzymatic membranes, or purification systems.

We identified the gene encoding the major S-layer protein in *M. alcaliphilum* sp. 20Z using quantitative proteomics on purified S-layer preparations. The S-layer protein appears to be the main cellular protein, comprising up to 20% of total cellular protein.

Lipase Production in Methanotrophic Cultures.

Figure 1A:
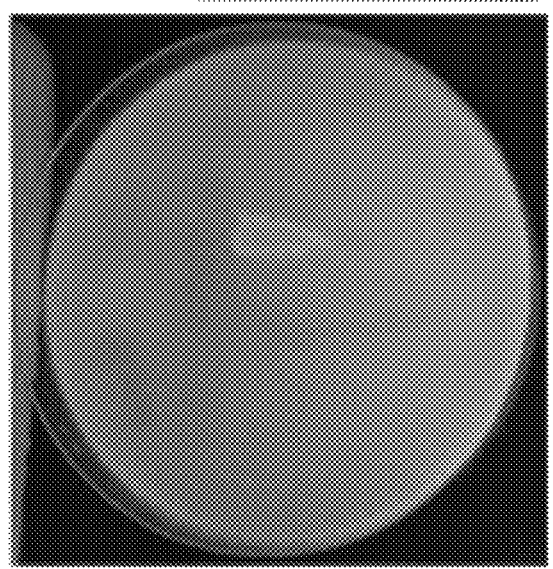

Lipase production by *Bacillus stearothermophilus* L1 [Kim et al. 2000] is optimal at 60° C. to 65° C. and pH 9 to pH 11 [Kim et al. 1998]. This lipase has been shown to have a 2 to 4 times higher activity for saturated fatty acids compared to monounsaturated ones. This makes L1 lipase a good candidate for hydrolysis of solid lipids like beef tallow and palm oil which are known to be difficult targets for currently used lipases. L1 lipase gene was codon optimized for efficient expression in methanotrophic host. The gene was synthetized and cloned into an expression vector and introduced into *Methylomicrobium* sp. AP18 for intracellular production; it's in vivo activity was detected on rhodamine B-containing plates (FIG. 1A). However, this construct showed low levels of lipase expression, i.e., the protein was not visible on Coumassie-stained polyacrylamide gel (PAAG) (FIG. 1B, lane 5).

In order to increase the expression, optimization of its ribosome binding site using in-house protocol was performed resulting in selection of clones with significantly higher expression (L1 comprising of about 1% to 2% of total cell protein (FIG. 1B, lanes 6 to 12)).

Construction of a Novel Genetically Altered Microbial Catalyst Producing Lipase (Up to 10% of CDW)

In order to further increase lipase production and simultaneously simplify its purification, an *M. alcaliphilum* 20Z strain expressing L1 lipase extracellularly as a fusion with S-layer protein is constructed. The fusion protein is introduced into the *M. alcaliphilum* 20Z chromosome using its native genetic elements to ensure high expression and proper extracellular localization of the fusion.

Figure 2A:
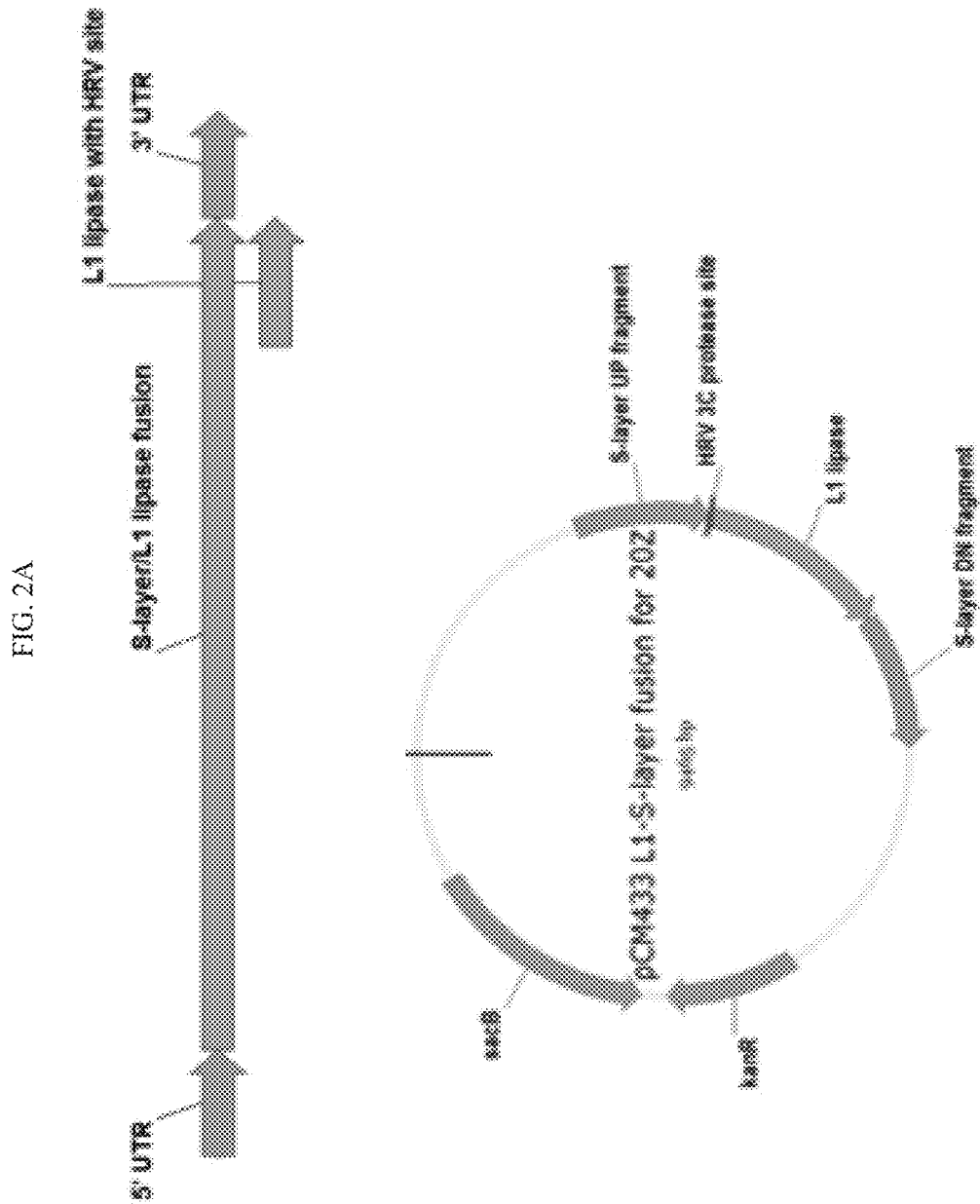
FIG. 2A-B illustrate construction and expression of a vector containing a novel genetically altered microbial catalyst producing lipase.

To facilitate lipase isolation, a site for HRV 3C protease is introduced between the S-layer and lipase polypeptides allowing the fusion protein to be cleaved with HRV 3C protease to release functional L1 lipase into solution, a genetic construct encoding this fusion protein is schematically illustrated in FIG. 2A, upper and lower images.

Figure 2B:
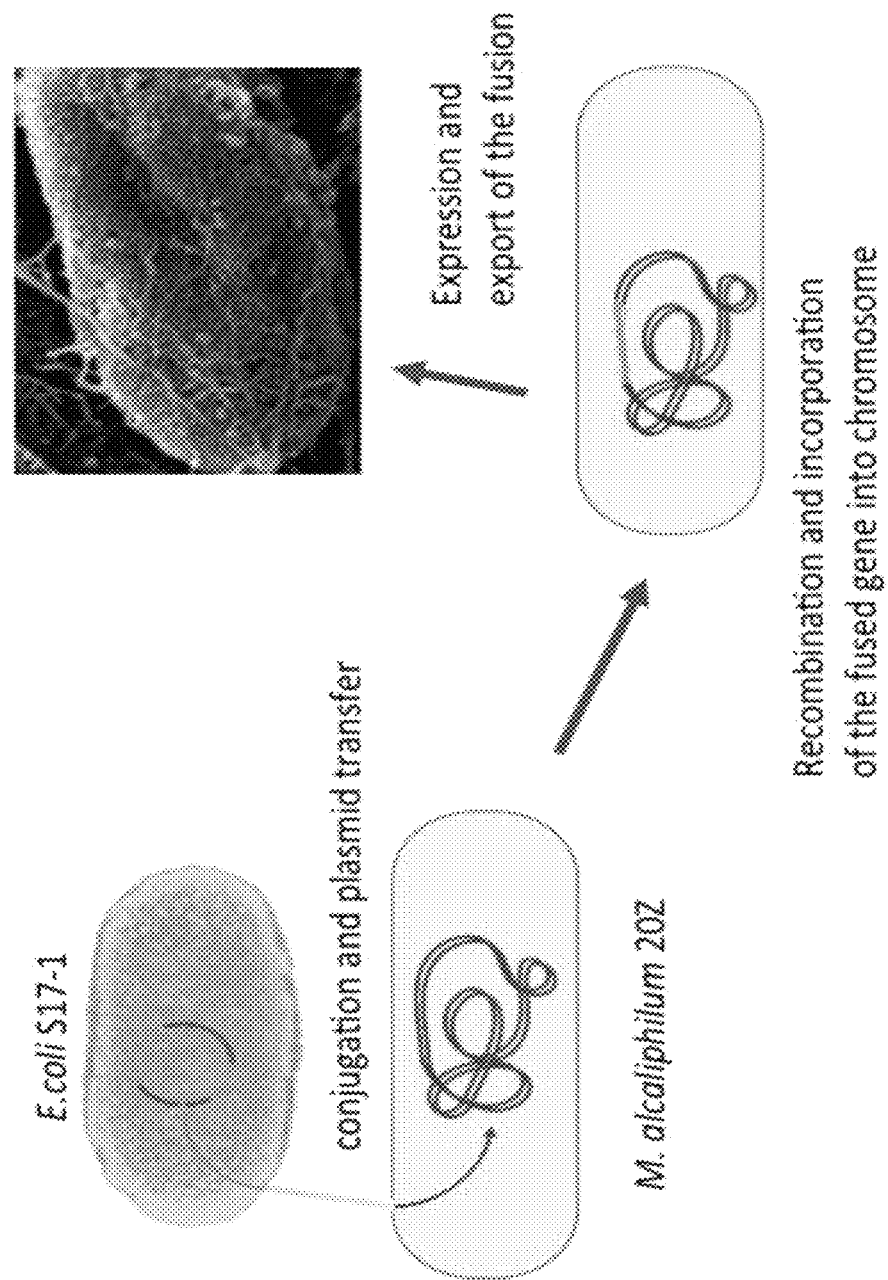

A plasmid containing this genetic construct is transferred from *E. coli* S17-1 by conjugation and plasmid transfer into an *M. alcaliphilum* 20Z strain, followed by recombination and incorporation of the fused gene (the genetic construct) into the chromosome, resulting in expression and export of the fusion protein, as schematically illustrated in FIG. 2B.

Methods.

The genetic manipulation includes the following set of steps:
1. PCR amplification of the codon optimized L1-gene and pCM433 vector;
2. PCR amplification of the S-layer upstream and downstream flanks. All reactions are done with a Q5 high-fidelity DNA polymerase;
3. Gibson assembly and transformation into *E. coli* NEB 5-alpha are performed using NEBuilder HiFi™ DNA assembly kit (NEBlabs);
4. Selected clones are validated by PCR (with Tag-polymerase, Invitrogen) and sequenced (at Eton Bioscience Center);
5. Validated plasmids are subcloned into *E. coli* S17-1 via transformation;
6. Biparental mating with *M. alcaliphilum* and clone selection is set up as described by Ojala et al. [2011];
7. Genotype characteristics is validated by PCR;
8. Phenotype characteristics of new traits is evaluated via scanning electron microscopy (SEM), lipase activity (rhodamine B assay) and SDS-PAAG electrophoresis.

Example 2: Exemplary Methods and Compositions

This example provides exemplary methods for making compositions and bacterial cells as provided herein, and practicing methods as provided herein.

Provided herein are new mitigation strategies for effective conversion of atmospheric greenhouse gases (e.g., $CO_2$ or methane) to next generation chemicals which are a new technology for the reduction/stabilization of global warming. In alternative embodiments, methods provided herein comprise use of biological systems (microbial cells or enzymes) as catalysts for conversion of e.g., $CO_2$ or methane.

Methanotrophic strain best suited for biotechnological exploration Two methanotrophic cultures were established as the most promising industrial strains: *Methylomicrobium alcaliphilumn* sp. 20Z and *Methylomicrobium buryatenses* 5G [Ojala et al., 2011; Kalyuzhnaya et al., 2015; Puri et al., 2015; Strong et al., 2016]. While *M. buryatenses* 5G represents a fast-growing methanotroph (Td=3 h), *M. alcaliphilum* sp. 20Z was found to be more stable at high-cell density. Furthermore, the latter strain has a greater potential for accumulation of extractable products (ectoine, glutamate, sucrose). Based on those characteristics, *M. alcaliphilum* sp. 20Z was selected.

Genomes of both *M. alcaliphilum* sp. 20Z and *M. buryatenses* 5G were sequenced (see e.g., Vuilleumier et al., 2012). Genetic tools for efficient metabolic engineering of the strains were developed or optimized (see e.g., Ojala et al., 2011; Puri 2015; Henard et al., 2016). The current toolbox includes: vectors for gene knockouts (incorporated via bi-parental mating or electroporation); vectors for heterologous expression with low, intermediate and high levels of expression; and vectors with tunable promoters. Provided is a whole-genome reconstruction of the *M. alcaliphilum* sp. 20Z metabolic network, which is refined via metabolomics on cells grown in liquid culture, providing a computation framework for additional optimization of metabolic pathways in producing traits.

Ectoine: Commercial Potential and Production in *Methylomicrobium alcaliphilum* Sp. 20Z.

Provided herein are methods for making ectoine ((4S)-2-methyl-1,4,5,6-tetrahydropyrimidine-4-carboxylic acid), which is a well-known microbial compatible solute. Ectoine can be used as a chemical chaperone for industrial enzymes or pharmaceuticals, a cryoprotectant, a hydrator in skin-care products, a cell stabilizer for medical treatments, and a crop-protecting agent [Graf et al., 2008; Pastor et al., 2010].

Figure 3:
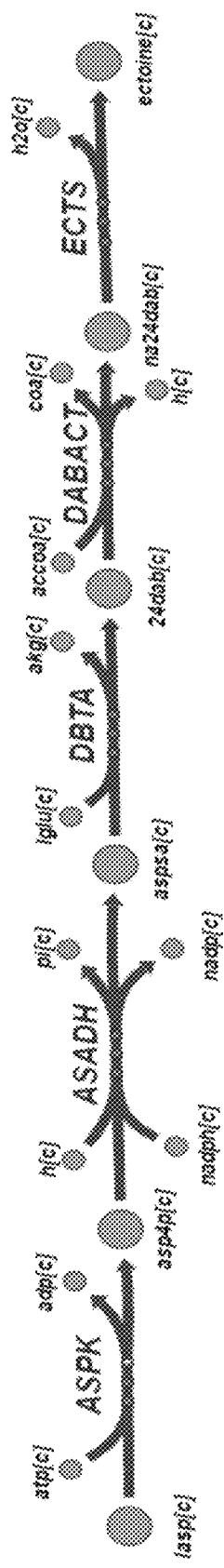
FIG. 3, schematically illustrates the ectoine biosynthesis pathway in *M. alcaliphilum* 20Z, including three specific enzymes: diaminobutyric acid (DABA) aminotransferase (EctB), DABA acetyltransferase (EctA), and ectoine synthase (EctC), as described in detail in Example 2, below.

*Methylomicrobium alcaliphilum* 20Z copes with high salinity in its growth medium by accumulating ectoine (up to 8% CDW), glutamate, and sucrose (up to 12% CDW) as major osmoprotective compounds. This strain was used as the most promising culture for ectoine production, see e.g., Totsenko et al, 2005. The ectoine biosynthesis pathway in *M. alcaliphilum* 20Z is similar to the pathway employed by halophilic/halotolerant heterotrophs and involves three specific enzymes: diaminobutyric acid (DABA) aminotransferase (EctB), DABA acetyltransferase (EctA), and ectoine synthase (EctC) (see e.g., Reshetnikov et al., 2011), as illustrated in FIG. 3. The ectoine biosynthetic gene cluster is organized as one operon (ectABCask) and is controlled by a negative transcriptional regulator (EctR1, marR-family). The EctR1 protein represses the expression of the ectABC-ask operon from the ectAp$_1$ promoter.

Baseline parameters and initial rates/titer of ectoine production for the wild strain (or wild type, WT) include: biomass yield (Y: 0.46), growth rate (0.09 h-1), $O_2$/substrate ratios (1.54), ectoine titer (1.9% DCW).

Strains Lacking the ectR-Regulator and Expressing LipL1 were Constructed

A set of strains lacking the ectR-regulator and expressing LipL1 were constructed. The strain lacking the ectR-regulator showed an ectoine titer similar to the WT; however, the strain demonstrated overproduction of a compound X, which was identified as a product of ectoine degradation. The deletion of the doeA-gene encoding ectoine hydrolase in the ΔectR background (Strain 20Z$^R$ΔectRΔdoeA) eliminated compound X accumulation and led to an increased production of ectoine (2.4% DCW). A LipL1 expression plasmid (P$_{SL}$-L1 construct) was subsequently incorporated into 20Z$^R$P$_{SL}$-L1ΔectR (to create TWC #G2) and 20Z$^R$P$_{SL}$-L1ΔectRΔdoeA (to create TWC #G2-3) which express LipL1. The specific activity of methanotrophic lipase is 1.2 U g$^{-1}$ CDW.

The growth rates of the strains TWC #G2, TWC #G2-2 and TWC #G2-3 are similar to WT. The strains TWC #G2-2 and TWC #G2-3 showed elevated ectoine (2.4% and 3.1% DCW, respectively), which corresponds to a production rates of 2.2 and 2.8 mg g$^{-1}$ CDW h$^{-1}$, respectively. The chemostat culture of TWC #G2-3 displays similar properties to WT growth kinetics and shows ectoine production as 3.3 mg g$^{-1}$ CDW h$^{-1}$. Thus TWC #G2-3 shows 1.7/1.8-fold improvement. The specific activity of methanotrophic lipase in TWC #G2-3 is 1.2 U g$^{-1}$ CDW.

Expression and purification of LipL1 protein. LipL was expressed and purified. Twelve mg of the protein with the specific activity of 589 U/mg were produced.

TABLE 1

List of exemplary genetic modifications in *M. alcaliphilum* sp. 20Z$^R$.

| Genetic alteration | Strain | Locus tag | Phenotype | IP/publication |
|---|---|---|---|---|
| Deletion: Transcriptional regulator MarR family | ΔectR::kan | MALCv4_3251 | No growth defects. Overexpression of the ectABC-ask operon. | Mustakhimov et al., 2010 |
| Deletion: Sucrose-phosphate synthase | Δsps::kan | MALCv4_0614 | No accumulation of sucrose is observed. No growth defects | WO2015058179 A1 |
| Deletion: Glycogen synthase 1 | Δglg1::kan | MALCv4_3507 MALCv4_3508 | Glycogen accumulation is reduced (10% of WT). No growth defects | WO2015058179 A1 |
| Deletion: Glycogen synthase cluster 2 | Δglg2::kan | MALCv4_3502. MALCv4_3503 MALCv4_3504 | Glycogen accumulation is reduced (5% of WT). No growth defects | WO2015058179 A1 |
| Deletion: Amylosucrose | Δams::kan | MALCv4_0617 | Significant decrease in intracellular glycogen accumulation and increase (15-20%) in sucrose accumulation. No growth defects | WO2015058179 A1 |
| Deletion: EPS biosynthesis | Δeps::kan | MALCv4_0618-MALCv4_0619 | TBD | New |
| Deletion: ectoine hydrolase | ΔdoeA | MALCv4_3246 | The strain was constructed in 20Z$^R$ ΔectR background | New |
| Overexpression of lipase | | Trait TWC#G120Z$^R$:: SL$_{Cter}$-LipL1 | No growth defects. Culture displays lipase activity (1.2 U g-1 DCW) | New |
| EctR deletion | | 20Z$^R$ ΔectR | Unmarked 20Z$^R$ ΔectR strain was constructed. No growth defects. Accumulation of products of ectoine degradation. No/mild increase in ectoine accumulation. | New |
| EctR deletion and overexpression of lipase | | Trait TWC#G2 20Z$^R$ ΔectR:: SL$_{Cter}$-LipL1 | No growth defects. Accumulation of products of ectoine degradation. No/mild increase in ectoine accumulation. | New |
| EctR deletion and DoeA deletion | | Trait TWC#G2-2 20Z$^R$ ΔectR ΔdoeA | No growth defects. Increase production of ectoine (1.6 fold increase). | New |
| EctR deletion and overexpression of lipase | | Trait TWC#G2-3 20Z$^R$:: SL$_{Cter}$-LipL1 ΔectR ΔdoeA (C-term) | No growth defects. Increase production of ectoine (1.7 fold increase). Culture displays lipase activity (1.2 U g-1 DCW). | New |
| Overexpression of Icl/ms | | Trait TWC#G2-4 20Z$^R$::P$_{hps}$-icl-ms | Improved growth (25% higher growth rate). Increased production of ectoine. | New, related to ectoine. |
| Overexpression of icl/ms | | Trait TWC#G2-v5 and v6 20Z$^R$ ΔectR ΔdoeA::P$_{hps}$-icl-ms | improved ectoine production (5.2%). No growth defects. | New |
| Overexpression of ectoine biosynthesis | | Traits TWC#G3 - TWC#G5 20Z$^R$ :: Phps-ectABC 20Z$^R$20Z$^R$ SL$_{Cter}$-LipL1ΔectR ΔdoeA:: P$_{opt}$-ectABC | No growth defects. 6.2% DCW ectoine | New |
| Multiple deletions | | TWC#G6-TWC#10 20Z$^R$ SL$_{Cter}$-LipL1 ΔectR Δsps Δglg1 Δglg2 Δeps ΔdoeA:: P$_{opt}$-ectABC-icl-ms | Traits with improved ectoine production | New |
| Multiple deletions | | Traits TWC#20 20Z$^R$ΔectR Δsps Δglg1 Δglg2 Δeps ΔdoeA:: P$_{opt}$-ectABC-icl-ms | Traits with improved ectoine production | New |

TABLE 1-continued

List of exemplary genetic modifications in M. alcaliphilum sp. 20Z$^R$.

| Genetic alteration | Strain | Locus tag | Phenotype | IP/publication |
|---|---|---|---|---|
| Expression of LipL from N-ter | TWC#G11 | 20Z$^R$:: SL$_{Nter}$-LipL1 | Lipase protein is expressed and excreted | New |
| Multiple deletions & Overexpression of lipase and ectoine | TWC#G12 | 20Z$^R$ SL$_{Cter}$-LipL1 ΔectR Δsps Δglg1 Δglg2 Δeps ΔdoeA :: P$_{opt}$-ectABC::icl-ms::SL$_{Nter}$-LipL1 | Terminated. New system for LipL expression should be constructed. | New |
| Expression of LipL from N-ter with intein | TWC#G13 | 20Z$^R$:: SL$_{Nter}$-LipL1- Ssp DnaB mini-intein | No growth defects. LipL accumulates in cytosol mostly. | New |
| Expression of LipL from N-ter | TWC#G14 | 20ZR:: SL$_{Nter}$-LipL1- Mxe GyrA | No growth defects. | New |
| Expression of GFP with SLP C-term fusion | | 20ZR:: GFP-12Cter$_{SLP}$ | Protein is expressed and excreted into growth medium | New |

Initial Cultivation Parameters for *M. alcaliphilum* 20Z$^R$ in Batch Cultures.

Strain and growth media: *M. alcaliphilum* 20Z$^R$ cells were grown using modified P media (g/L): KNO$_3$, 1; MgSO$_4$× 7H$_2$O, 0.2; CaCl$_2$)×2H$_2$O, 0.02; NaCl, 30; trace solution, 1 ml/L (Table 2); and supplemented with 20 ml/L of phosphate solution (5.44 g KH$_2$PO$_4$; 5.68 g Na$_2$HPO$_4$) and 20 ml/L of 1M carbonate buffer.

TABLE 2

Trace solution composition.

| Trace solution (1000x) | g | |
|---|---|---|
| Na$_2$EDTA | 5 | The solution was autoclaved at 121° C. for 20 minutes and stored at room temperature for up to 6 months. |
| FeSO$_4$ × 7 H$_2$O | 2 | |
| ZnSO$_4$ × 7 H$_2$O* | 0.3 | |
| MnCl$_2$ × 4 H$_2$O | 0.03 | |
| CoCl$_2$ × 6 H$_2$O | 0.2 | |
| CuSO$_4$ × 5 H$_2$O | 1.2 | |
| CuCl$_2$ × 2 H$_2$O* | 0.5 | |
| Na$_2$O$_4$W × 2H$_2$O | 0.3 | |
| NiCl$_2$ × 6 H$_2$O | 0.05 | |
| Na$_2$MoO$_4$ × 2 H$_2$O | 0.05 | |
| H$_3$BO$_3$ | 0.03 | |

*The growth media has higher concentrations of CuCl$_2$ and ZhSO$_4$ compared to our published media (modified from Demidenko et al., 2017).

Cultivation

Culturing was carried out in either closed vials (50 ml culture in 250 ml vials, with shaking at 200 r.p.m.) or bioreactor cultures (fed-batch or turbidostat). Two types of bioreactors were used: 1) a DASBOX™ (DASbox) mini bioreactor (0.5 L working volume; 200 ml culture) with two individual bioreactor units, each having automatic temperature, pH, and DO controls, a sample port for measuring OD, and a coupling to a BLUESENS™ (BlueSens) sensor system for simultaneous measuring off-gases (CH$_4$, O$_2$, and CO$_2$); or 2) a 2.7 L bench top BIOFLO (BioFlo) 110™ modular bioreactor (New Brunswick Scientific, Edison, N.J., USA). Cultures were also grown as batch cultures (in triplicate). In all cases we measured CH$_4$, O$_2$, and CO$_2$ in the headspace to determine consumption and production rates and the O$_2$/substrate utilization ratios using an SRI GC system. In addition, samples were taken for measuring ectoine concentrations in cell biomass by HPLC. The data were analyzed to assess yield (Y), growth rate, and O$_2$/substrate ratios (Table 3).

Dry Cell Weight (DCW) Measurement

Cultures (150 ml) from bioreactors were centrifuged to collect the biomass. After careful removal of the liquid phase, tubes of known weight with biomass were weighed (to obtain wet cell biomass weight), lyophilized overnight using a LABCONCO™ freeze-dry system and weighed again. The observed DCW parameters were as follows: 1 L of cell culture with OD=1 corresponds to 0.336±0.025 g CDW.

FIG. 4A graphically illustrates data showing the growth of *M. alcaliphilum* 20ZR in a DASBOX™ (DASbox) mini bioreactor (0.5 L working volume; 200 ml culture), as batch (0-20 hours (h)) and chemostat mode (20 h-90 h). Steady-state was reached at 60-80 h. B-C. O$_2$ and CH$_4$ consumptions and CO$_2$ production in steady-state for bioreactor replicate 1 (FIG. 4B) and 2 (FIG. 4C).

HPLC Protocol

Twenty mg of lyophilized biomass was re-suspended in 200 μl of water. One ml of 0.2M sodium citrate buffer (pH 2.2) was added and quickly (15 sec) sonicated to re-suspend. The mixture was allowed to sit on the bench at room temperature overnight (18 h) and then sonicated again (15 sec). After centrifugation for 10 min, the clarified lysate was filtered through 3 kDa centrifugal filter units (Millipore) and the filtrate was analyzed by high performance liquid chromatography (HPLC). Ectoine concentrations were determined by using a previously published assay (He at al., 2015), i.e., an isocratic mobile phase of acetonitrile and water (70:30 v/v), flow rate of 0.5 ml/min and a detection wavelength of 210 nm. Samples (10 μl) were chromatographed using an Agilent 1100™ HPLC system equipped with a NUCLEOSIL NH2-HPLC™ column, 5 μm particle size, 25 cm×4.6 mm (Macherey-Nagel). Pure ectoine purchased from Sigma was used as a reference (FIG. 3A).

Figure 5A:
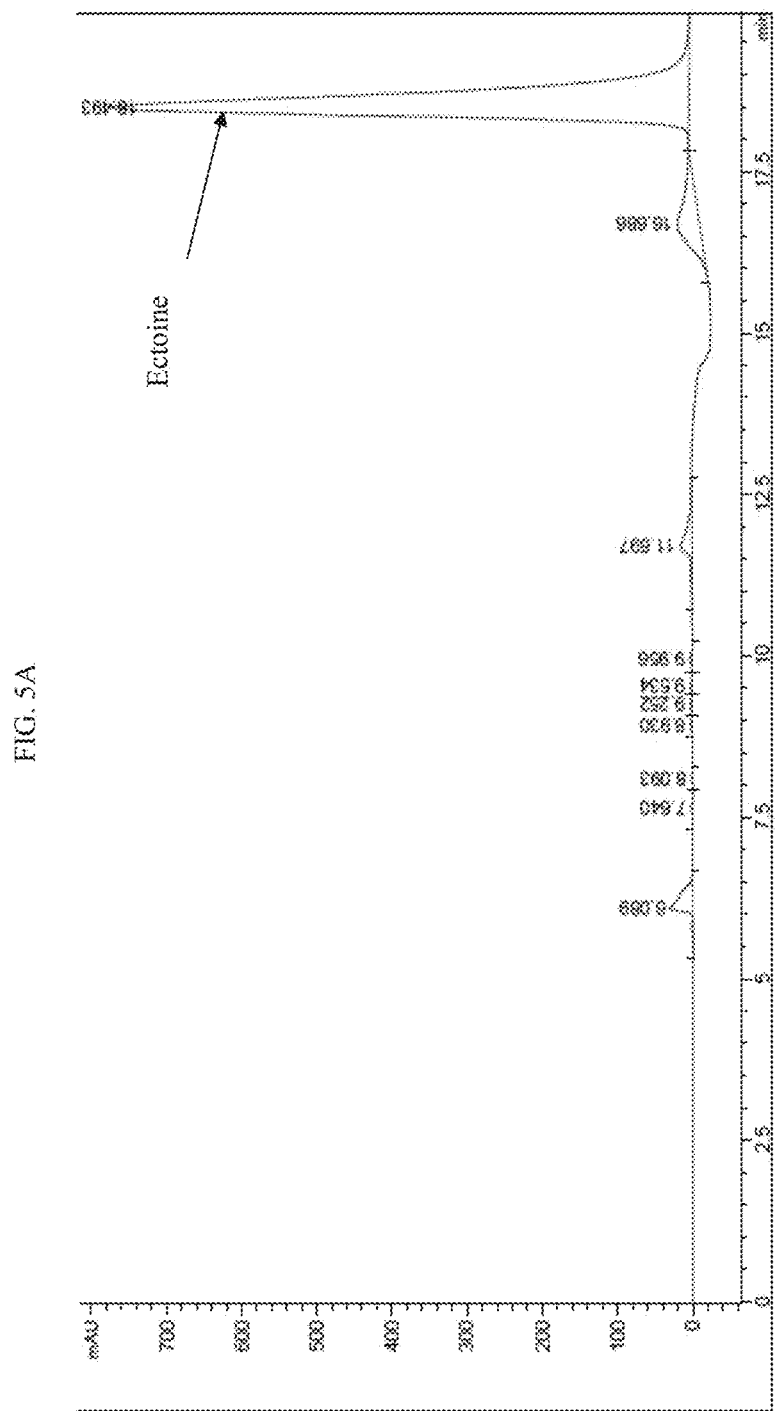
FIG. 5A-B.
Figure 5B:
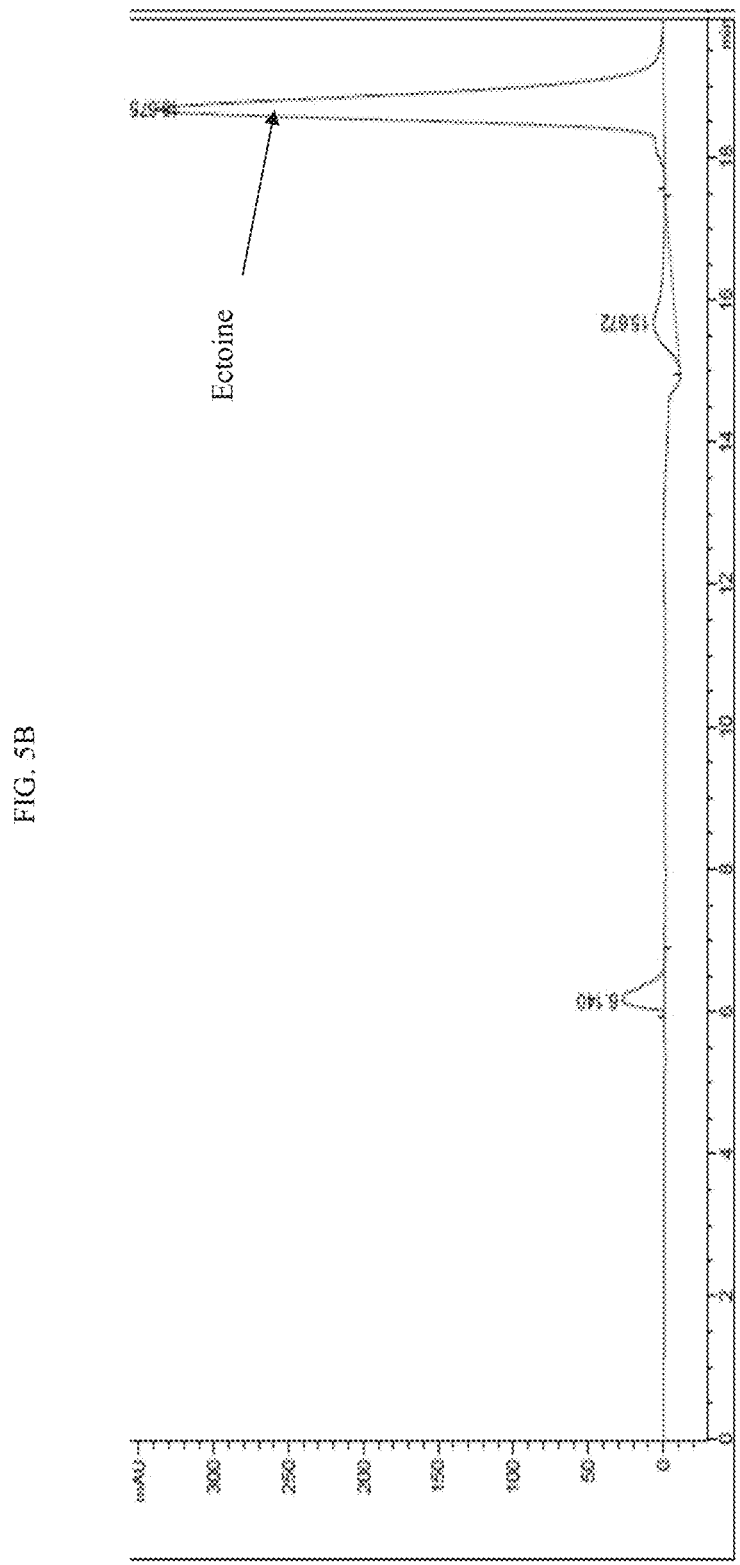

FIG. 5A illustrates a chromatogram of 1 mM ectoine solution; ectoine peak area=8497; FIG. 5B illustrates a chromatogram of 20ZR cell extract; ectoine peak area=18066 (corresponding to 370 ug of ectoine per 20 mg of dry cells, or 1.85%).

Results

A bench-scale New Brunswick BIOFLOW (Bioflow) 310™ bioreactor was used to accumulate cell biomass. A DASBOX™ (DASbox) mini bioreactor system was used to generate performance parameters for continuous cultures grown on methane. The parameters measured from these growth conditions include cell dry weight, CH$_4$ and O$_2$ uptake rates, glycogen content, and excreted organic acids.

The parameters for continuous culture conditions and catalyst performances are shown in Table 3, below. A maximal growth rate of 0.13 hr$^{-1}$ was obtained under fed-batch conditions using our standard gas mixture. The specific growth rate in the continuous culture was 0.09-0.1 hr$^{-1}$ (see FIG. 4) at DCW 1.15 g/L.

TABLE 3

Baseline parameters for M. alcaliphilum 20Z$^R$ grown in a bioreactor with methane as a source of carbon/energy.

| Parameter | | SD |
|---|---|---|
| Gas input | 5% CH$_4$:3.5% O$_2$:N$_2$ balance | |
| Gas flow | 1.6-1.7 L/h | |
| Bioreactor volume | 0.2-2 L | |
| Growth rate (h$^{-1}$) | 0.09 | 0.01 |
| Methane consumption (mmol g DCW$^{-1}$ h$^{-1}$) | 12.2 | 0.9 |
| Oxygen consumption (mmol g DCW$^{-1}$ h$^{-1}$) | 19.7 | 3.3 |
| CO$_2$ produced (mmol g DCW$^{-1}$ h$^{-1}$) | 4.6 | 0.9 |
| Y CO2 (%) | 0.37 | 0.05 |
| Y (biomass) | 0.46 | 0.02 |
| O$_2$/CH$_4$ | 1.54 | 0.04 |
| Ectoine (% DCW) | 1.86 | 0.07 |
| Productivity (g ectoine g$^{-1}$ DCW h$^{-1}$) | 0.0016 | 6.3 × 10$^{-5}$ |

Construction of a Methanotrophic Strains Lacking ectR-Regulator and Expressing LipL1.

Construction of 20Z$^R$ΔectR strain lacking ectR-regulator. The strain was constructed and tested for ectoine production:

Strain construction. Plasmid pCM433kanT carrying approximately 800 base pairs (bp) of sequences flanking ectR gene was constructed and introduced to 20ZR strain by biparental conjugation. After mating, single-crossover, kanamycin-resistant clones were plated on rifampicin to counter-select against E. coli. Then, to select for Kan-sensitive double crossover clones with a deleted ectR gene, single-crossover clones were passaged on plates with 2.5% sucrose and the resulting colonies were PCR-genotyped for the absence of ectR followed by sequencing (underlined sequences, as described below).

Figure 6:
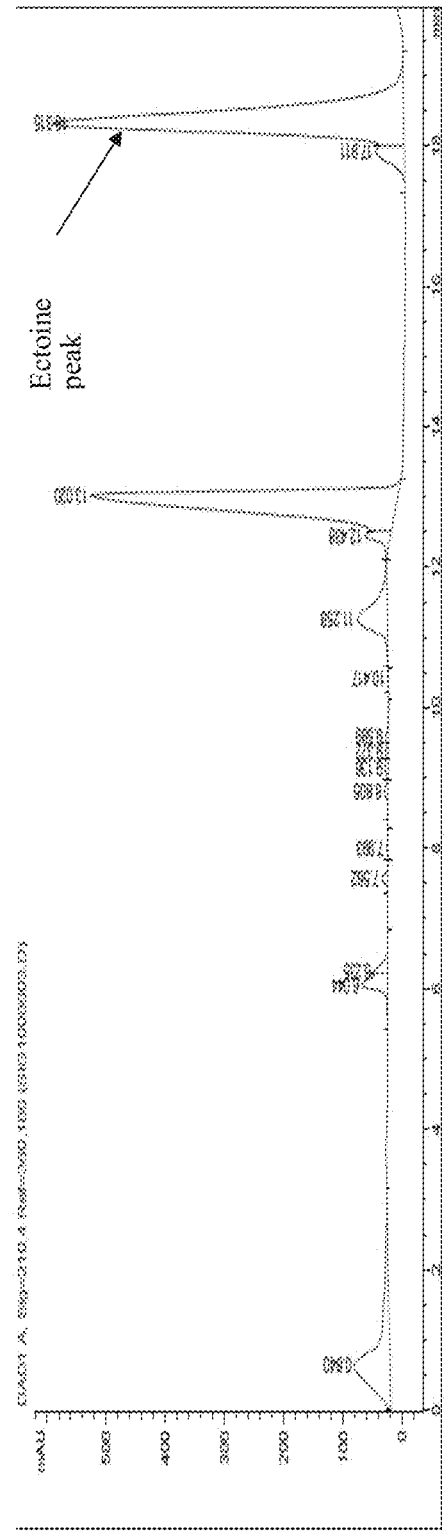
FIG. 6 illustrates a chromatogram of an HPLC analysis of $20Z^R$ wild-type as a batch culture, as described in detail in Example 2, below.
Figure 7:
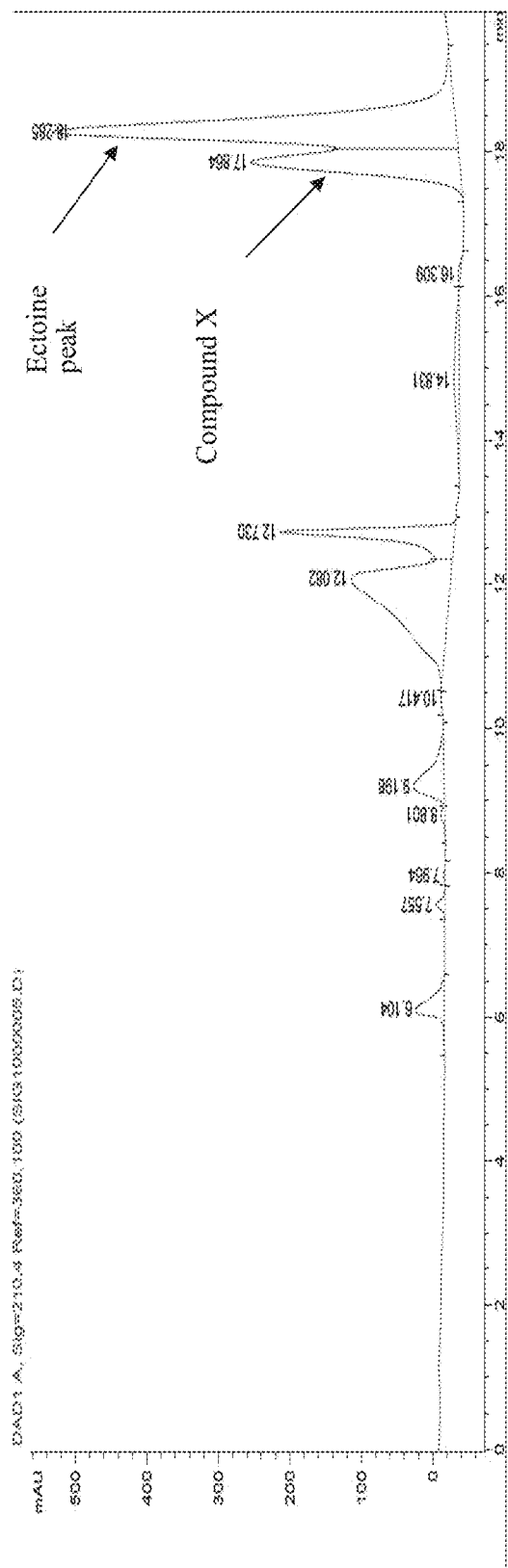
FIG. 7 illustrates a chromatogram of an HPLC analysis of $20Z^R\Delta ectR$ strain in batch culture, as described in detail in Example 2, below.

Results. Amounts of ectoine in 20Z$^R$ΔectR strain are similar to the parental (WT) strain, see FIG. 6 (illustrates HPLC analysis of 20Z$^R$ wild-type (batch culture)) and FIG. 7 (illustrates HPLC analysis of 20Z$^R$ΔectR strain (batch culture). However, the peak adjacent to ectoine (at 17.8 min) was significantly enriched in the ΔectR strain (FIG. 7). It was suggested that the peak might be an intermediate of the ectoine degradation, thus an additional mutation, knockout of the ectoine hydrolase (doeA) gene, was generated.

Construction of the 20Z$^R$ΔectRΔdoeA Strain.

Strain construction. The strain 20Z$^R$ΔectR was used as the parental strain. The ΔdoeA knockout was constructed the same way as for the ectR deletion. The selected clones were PCR-genotyped for the absence of the doeA gene followed by sequencing.

Figure 8:
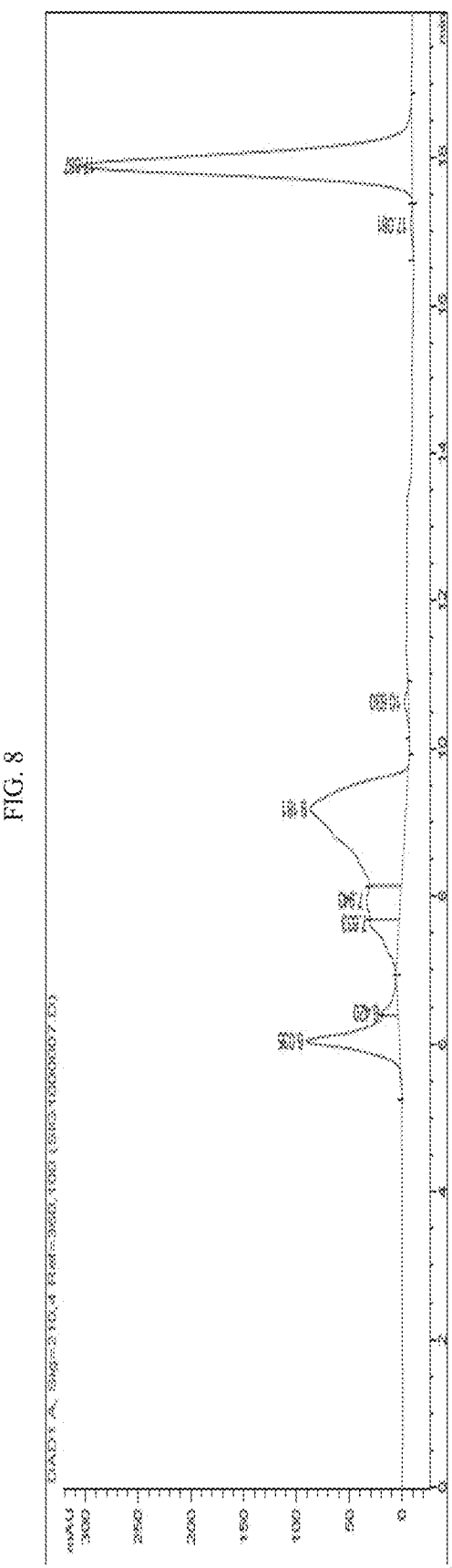
FIG. 8 illustrates a chromatogram of an HPLC analysis of $20Z^R\Delta ectR\Delta doeA$ strain (batch culture), as described in detail in Example 2, below.

Results. HPLC analyses of the cell extracts showed increased level of ectoine in the 20Z$^R$ΔectRΔdoeA strain (26% more than in WT, Table 4) and no ectoine degradation intermediate (compound X) was observed, see FIG. 8 (illustrates HPLC analysis of 20Z$^R$ΔectRΔdoeA strain (batch culture)).

Construction of the TWC #G2 and TWC #G2-2 Strains Expression LipL1.

Strains for simultaneous production of lipase (as a fusion with S layer protein) and ectoine 20Z$^R$P$_{SL}$-L1ΔectR (TWC #G2) and 20Z$^R$P$_{SL}$-L1ΔectRΔdoeA (TWC #G2-2) have been made.

Strain construction. EctR and doeA genes were introduced into WT and TWC #G1.

Figure 9A:
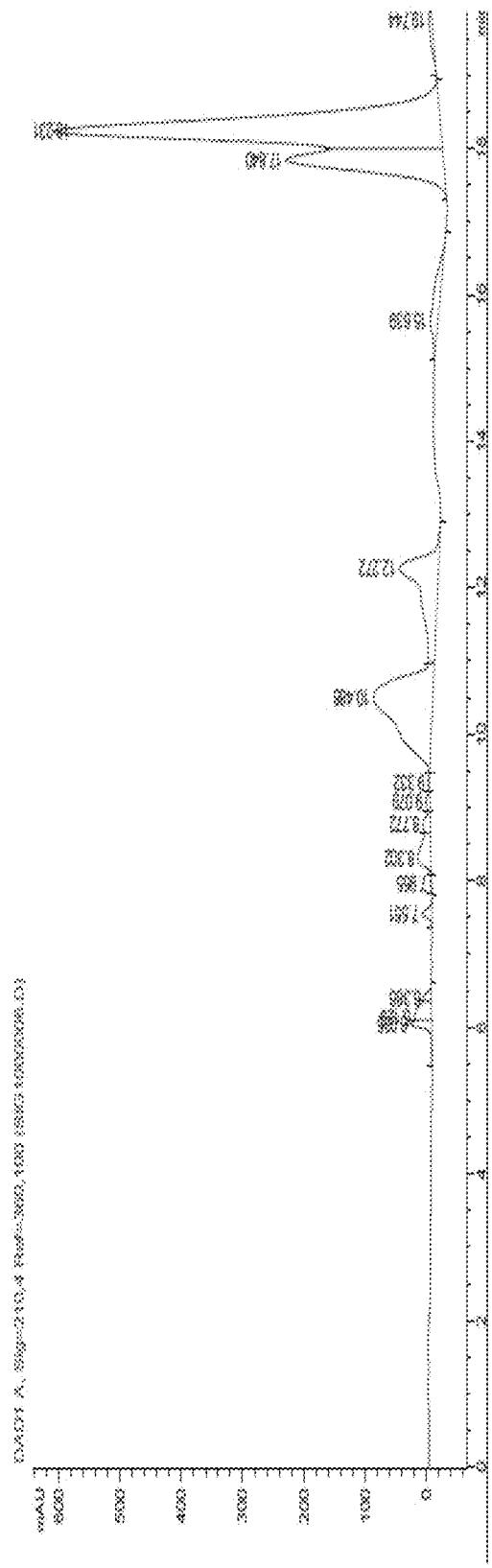
FIG. 9A-B illustrates chromatograms HPLC analyses that reveal the highest levels of ectoine.
Figure 9B:
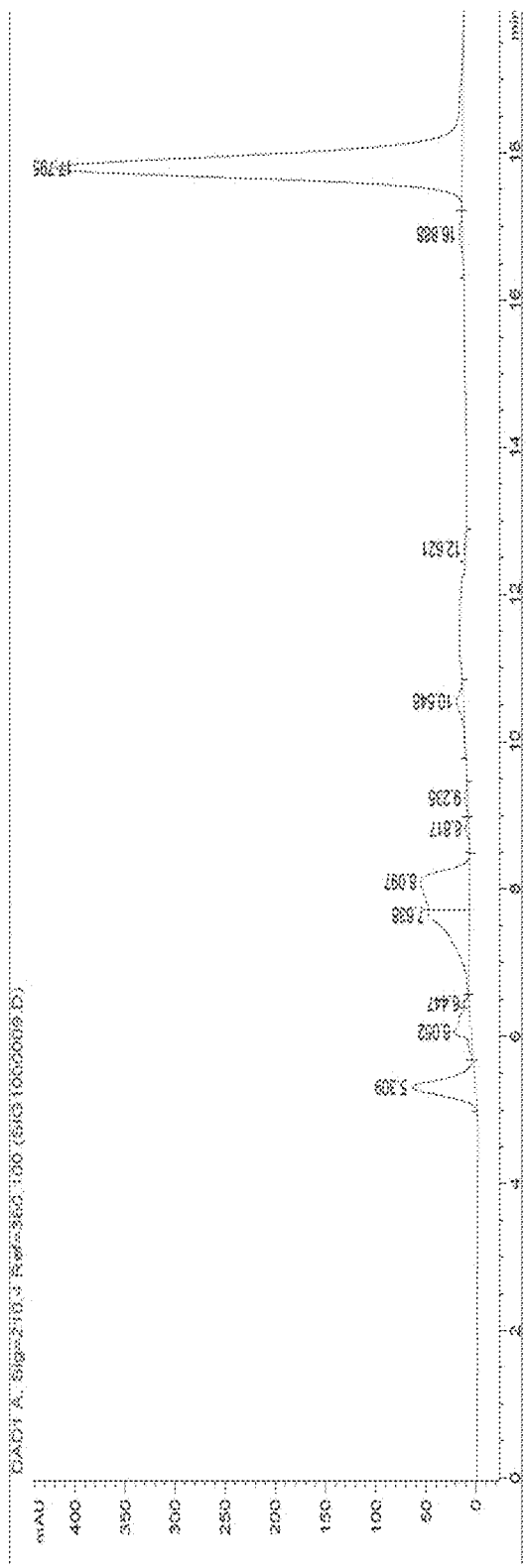

Results. HPLC analysis reveals the highest levels of ectoine, 160% more than in WT 20Z$^R$, Table 4, FIG. 9A-B (illustrates HPLC analysis of HPLC analysis of 20Z::P$_{SL}$-L1ΔectR (FIG. 9A) and 20Z$^R$P$_{SL}$-L1ΔectR ΔdoeA (FIG. 9B) strains (batch cultures).

Additional Genetic Strategies for Improving Ectoine Production.

As an additional way to improve ectoine production, an isocitrate lyase/malate synthase fusion was expressed in the 20Z$^R$ strain under hps promoter (P$_{hps}$). The expression of the construct was expected to provide an additional route for oxaloacetate production, a key intermediate in ectoine biosynthesis. As expected, the level of ectoine in the strain 20Z$^R$::P$_{hps}$-icl-ms was increased (26% more, Table 4) compared to the wild type strain. Incorporation of the pCM132::P$_{hps}$-icl-ms producing plasmid into strain TCW #G2-2 strain is in progress.

Batch Culture Cultivation.

Growth characterization of the strain was done as described for WT. All batch cultures showed the same growth rate as WT cultures. Ectoine concentrations were estimated as described in Table 4. Each additional experiment included WT cells as a control.

TABLE 4

Ectoine titer and production rate in genetically modified methanotrophic traits: Averaged data (n = 2-6) for ectoine production

| Strain genotype | Strain name | Ectoine, % of DCW | % of initial | Productivity (mg g$^{-1}$, CDW h$^{-1}$) |
|---|---|---|---|---|
| WT- ref$^R$ | 20Z$^R$ | 1.9 ± 0.04 | 100 | 1.6 |
| ΔectR | 20Z$^R$ ΔectR | 2.0 ± 0.15 | 100 | 1.6 |
| 20Z$^R$P$_{SL}$-L1ΔectR | TWC#G2 | 2.6 ± 0.06 | 100 | 2.3 |
| 20Z$^R$ΔectRΔdoeA | TWC#G2-2 | 2.4 ± 0.3 | 125 | 2.2 |
| 20Z$^R$P$_{SL}$-L1ΔectRΔdoeA | TWC#G2-3 | 3.1 ± 0.06 | 160 | 2.8 |
| 20Z$^R$::P$_{hps}$-ms-icl | TWC#G2-4 | 2.4 ± 0.02 | 125 | 2.7* |

*The strain has improved growth rate (was recalculated to specific growth rate in the continuous culture as 0.12 vs 0.09 h$^{-1}$)

Cultivation in Mini-Bioreactor in Continuous and High Cell Density Batch Modes.

Cultivation of TWC #G2-3 was performed in a DAS-BOX™ (DASbox) mini bioreactor (0.5 L working volume; 200 ml culture with two individual bioreactor units. Gas input and operational parameters were the same way as described for WT strain. Collected data are summarize in Table 5 and shown in FIG. 10A-C (FIG. 10A illustrates growth of M. alcaliphilum 20Z$^R$P$_{SL}$-L1ΔectRΔdoeA (TWC #G2-3) in DASbox mini bioreactor (0.5 L working volume; 200 ml culture), as batch (0-65 h) and chemostat mode (65 h-120 h); Steady-state was reached at 90-100 h. FIG. 10B-C illustrates O$_2$ and CH$_4$ consumptions and CO$_2$ production in steady-state for bioreactor replicate 1 (FIG. 10B) and 2 (FIG. 10C)).

The strain TWC #G2-3 grown in continuous culture in mini-bioreactor produce twice the amount of ectoine as WT (Table 5). The ectoine productivity was calculated as was 3.3±0.3 mg h$^{-1}$ g$^{-1}$ CDW.

TABLE 5

Parameters for TWC#G2-3 grown in a bioreactor with methane as a source of carbon/energy.

| Parameter | | SD |
|---|---|---|
| Gas input | 5% CH$_4$:3.5% O$_2$:N$_2$ balance | |
| Gas flow | 1 L/h | |
| Bioreactor volume | 0.2 | |
| Growth rate (h$^{-1}$) | 0.09 | 0.01 |
| Methane consumption (mmol g DCW$^{-1}$ h$^{-1}$) | 8.6 | 1.2 |
| Oxygen consumption (mmol g DCW$^{-1}$ h$^{-1}$) | 11.6 | 1.6 |
| CO$_2$ produced (mmol g DCW$^{-1}$ h$^{-1}$) | 3.1 | 0.4 |
| Y CO$_2$ (%) | 0.37 | 0.45 |
| Y (biomass) | 0.59 | 0.13 |
| O$_2$/CH$_4$ | 1.35 | 0.01 |
| Ectoine (% DCW) | 3.1 | 0.07 |
| Productivity (g ectoine g$^{-1}$ DCW h$^{-1}$) | 0.0033 | 2.9 × 10$^{-5}$ |

Expression and Purification of LipL1 Protein.

Purification of lipase after expression in *E. coli* BL21 (DE3).

Strain Construction.

Codon-optimized sequence of LipL1 with N-terminal His6 tag was cloned into pET21 plasmid under T7 promoter; the construct was introduced into *E. coli* BL21(DE3) strain.

Expression and Purification.

Cells were grown in 300 ml of LB with ampicillin (100 ug/ml), at which point lipase production was induced by addition of IPTG (0.5 mM final) at OD600=0.5 and continued for 7 h at 37° C. Cells were collected by centrifugation. For purification, cells were lysed by French Press (purifications 1 and 2) or by sonication in the presence of 0.5% Triton X-100 (purification 3), clarified lysate was loaded to Talon resin (Clontech) for one-step purification by metal affinity chromatography. After washing of the resin and elution of lipase with 200 mM imidazole, lipase prep was dialyzed against 20 mM tris-HCl (pH 8.0) and 100 mM NaCl buffer followed by addition of glycerol to 50% w/w and stored at −20° C.

Activity Assay.

Activity of the isolated lipase has been confirmed on Rhodamine B plates and by p-nitrophenoldecanoate assay. One unit was defined as the amount of enzyme that released 1 μmol 4-nitrophenol.

Purity Validation.

Purity of the purified lipase was checked by electrophoresis on SDS-PAAG (12% mini-Protean TGX™ gels, Bio-Rad) according to manufacturer's protocol. Gels were analyzed and quantified with IMAGELAB (ImageLab) 4.1™ software (Bio-Rad) and are shown below (FIG. 7); in all 3 cases only the protein band corresponding to LipL1 is visible, no other (contaminating) proteins are present.

Three sets of LipL1 expression and purification were performed. In total, about 12 mg of pure L1 lipase were isolated.

TABLE 6

Summary of LipL1 protein preparation

| Preparation | Volume ml | Protein mg | Specific activity* U/mg |
|---|---|---|---|
| P# 1 | 1.5 | 3 | 630 |
| P# 2 | 2 | 7 | 400 |
| P# 3 | 2 | 2 | 1200 |
| Total | 5.5 | 12 | 589 |

*1 unit (U) is the amount of enzyme that catalyses the reaction of 1 umol of substrate per minute.

Lipase Production in Methanotrophic Strain TWC #G1, TWC #G2 and TWC #2-G2:

Different constructs have been made for production of lipase from plasmids (under different promoters) and from genomic DNA as a fusion with S-layer protein. All of the strains have been shown (qualitatively) to produce active lipase by both Rhodamine B and p-nitrophenoldecanoate assays. The specific activity of methanotrophic lipase in TWC #G2-3 is 1.2 U g$^{-1}$ CDW. FIG. 11 illustrates LipL1 preparations.

Construction of Strains TWC #1, TWC #2 and TWC #2-2:

The coding sequence for LipL lipase was introduced into the 20Z genome as C-terminal fusion with S-layer protein of 20Z$^R$. A HRV3C protease recognition site was placed in frame between the S-layer protein and lipase sequences to allow protease cleavage of the fusion polypeptide and release of the free lipase. The codon-optimized LipL lipase sequence (synthesized at GENSCRIPT™ (GenScript)) with the HRV site was introduced by PCR. Plasmid pCM433kanT carrying approximately 800 base pairs (bp) of sequences flanking the fusion site of S-layer protein was constructed and introduced to the 20ZR strain by biparental conjugation. After mating, single-crossover kanamycin-resistant clones were plated on rifampicin to counter-select against *E. coli*. Then, to select for Kan-sensitive double crossover clones with inserted lipase gene, single-crossover clones were passaged on plates with 2.5% sucrose and the resulting colonies were PCR-genotyped for the presence of lipase followed by sequencing.

```
Genomic region of ectR (MALCv4_3251) with upstream and
downstream flanks. The genetic region deleted in ΔectR strain
(ectR gene) is underlined) (SEQ ID NO: 1):
gaaccgctttgaacggcccaaccttcaccagcatttcggtttcatgttgatctgcaa aatggcgtgtcttatcaaacatcacagcactgccaatttgagtgtccagttttttttg ccagcccctcaaacagagcccatgaggccttattattcggagtaatggtcgtctcga ttcggttaatatcctgattgaccggccgcgccagtatggctttcagcatccgcgtgg caagcccttggccacgggcttttcgccgacagccacctgccagacaaacagcgtat ccggacgttgcggaatacgataacccgagacaaaaccaaccaactcatcgccaattt
```

-continued tggccgccaccgccgtttcagaaaaatggctgctctgcagcaaattgcagtacatcg aattgggatccaggggcgggcatttgctaatcagccgatgcacctgcgctccgactt cggcagtaggctggctaagtgtaataatcggcaaggcagttttatcaggcaacatat aaataactctattatttagatttctgtgcaattaactcggctttaactgaataagcc gggctcgaatttgattttttatggccatcagcacgaatattctggcttcattgaaaa acataatatatagtacactaaataatttaaatgtccaggccgcgtacttttgcctta gattaattagatgtcatatcaaattatgcctttcgaacttcaaatttcggtagcgcc ctaggatgcgccgggcggagcaccgaattttgttcttcgagggtatacaataatggc tttgtaacgcgacggcctctatttca<u>atgattggtgatcaatgatgcaaaacccaca</u>

<u>accgcacgcccctcattcgctggatacgctcgacttgaatccggttgaaaaggaaca</u>

<u>tttgctgaatcaaattgaagaagtactggtcgcgttacgtagagtgattcgcgccac</u>

<u>cgatttacactcaaaatatctggcaaaaaccactagcctgaccgcaccgcagattct</u>

<u>tttgttgcagacactgcgcgccaaaggtcaactgaccattggtgagctagctcagga</u>

<u>catgagtctcagccaagcgactgtgacaacaattctggatcgcctggaaaaacgtca</u>

<u>attggtgttccggcagcgctcccagactgataaacgaaaagtccatgtctatatgac</u>

<u>ggaggcggccacggaaatgctaataaacgcccctatccctttgcaggatcgctttac</u>

<u>gcgagaattcagtaaactacaggaatgggaacaattgatgattattgcatcactgca</u>

<u>acgtgtcgctcagatgatggacgcgcagaacatccctgtcgctaaagaagcgtttga</u>

<u>ttttccggtttaagctctaataatt</u>cagctcagctgcaacccgcatcacgcttttc ccaagctccagcttgggaaaaacaccccggaagctccagcttccagaaaccgagata acctccgcacattctcaatcaaccccgactcgctcgttcaatcttttttcctgattag caagatgcttcaacttgctgaagccaattgtccgagcagtggccagtcgtagccact tctgcgggacgggttatttaacccatccccaacgtttcggtttgccctaaacatttc ggctgacttcggccaaagtcaaaacgtttaggacggggctgcaaaccccgtcctgct aaggatatgctggttttcgggctttagctgaagaaacttgctaatcaggatcttttt tgattgtcgggaagctagagcttcctgaatagattacccaagccggatcgctcgccg ctatacacaaatatcggtaaacttgctaaacagaggtcgccgtatacttggaagcgg tgctgtttgataaatctgcggatattggacatcagtggcttcgaagtcgggaacgtt gggcgataaaaaatggtatcgaggcctcattggttaagattgcaaaagggtaatttt tgacttatgtataacgatgaggtaactattcagtcccccggcaattatcgttcccac gctctgcgtgggaatgcctgagtaccgctccagcggtacgagacgctagagcgtctc ggtcttcattcccacgccggagcgtgagaacgataggcggtgtgaataattacacga tgagagctggagcttgggtaacagcacaaaggcatatttagcctagttgc Genomic region of doeA (MALCv4_3246) with upstream and
downstream flanks. The genetic region deleted in ΔdoeA strain
(doeA gene) is underlined (SEQ ID NO: 2):
gtagcaagccttgcgtagagattattgccgggtgtaaaggcgtctatgct -continued agcagatcagcgtgcttgcaatgcaccagtcaatgcgtcaagtcgatatgcagtttg tgattgatgaagatgcctacactgatgcgatgaaaagtttgcattgtcatctggtgg aggtccatgatcacggcattgcaatatgcctcgcgtcctgattgtactgatgtttct taccc ctaaatacggggaaatttctcaaactgggaattgctgccaaagaaatgaaaa tgccttgcgtcttcagtcttgcgctgaacgacaaggaagcgcataaggcttaaagcg tttaccactcgaccgctgaagcggtagcggattaaggcgagtcgcaagtcaattttc gtccaaggttaggttgttcatggcaagtcagtcgagcaatgaatgacttaaccgtct attttt caataaactgaagatgtacgggtaagccctgcgtaagttgggaatggccga tgatcgagggctatctgttgtcgcgaagtctttaatcaaaaaaatgggtttaatatt caatgattaccgagaatgccgcacagtccgaacaaagtgaagatttttatcaatcac gtaacggtagtaagccgaaaataattccgcgcgtagacccggtagtttatgcgcaaa cagctaatccaggtctcattgcagaggacttgcaagcacgttatgagcaacaaggtt ttcttgttattgataatgttttt aatgagagggaggtcgactgtttcaagcaagagc tcaaacgcttgaacgacgatgaaaagataaaagcctcggcggaagcgataactgaat tatccagcgacgaactccgttcactatttaaaattcatgaagtcagtccggttttta aaaggttagctgccgataatcgattagcgggactggctcaacatcttttgaacgacc gggtttatattcatcagtcgcgcttaaactataagccgggttttcgcggcaaggaat tttactggcattcggactttgaaacttggcatgtagaagacggtatgcctagaatgc gtgcgctcagcatgtccattattcttaccgaaaacgatcagcataacgggcctttga tgttggttcccggatcgcataaaaaatttgtcgtttgcgaagaggaaacgccggaaa atcattattcggtctcgttgaaaaagcaggagtacggcatacccagcgatgaatgct tggctagcttggttgccgatggcggcatcgtatcggccaatggaaaacccggcagtg tcttgattttcgacagtaatgtcatgcacggttcgaatagtaatatcactccatggc ctcgctcgaatctctttttcgtctataacgcgatcaataatcgagtaacatggccgt tttgcggtttattgccgcgtcctgaatatctttgcagtcgcaagaatatacgagtta tcgaaccgcggccttttatcgcggccgccgatcaattgatatgcttagaatgtta ataatgttgatcgtgctggcgccctgttccgtgttgggcgagagcgtcaacgatgaa gcagaggttcaagagcgcttagatgcggttgaatctttggataagcctttatatagt ccgttcatcgagcgctatatgctggatgaactcaaacaattgcgtatggacatggca gcgcagaggaatgagctgattcagcaaattgtggatagagagcttagctcggtcgat agaggcgttacttacgccactaatactgtcacatattttttctacttgattgccggt gccagtaccattttggtgttgctgggttggacctcgctcagagatatcaaagagcgt gtgcagtccatggcggataagaaagtatcgaaactggtccatgaatacgaagagcgc ttggcaattgtcgaacaacaactcaacaaggaagcacaattgattgagaaaatcggc gaggatatcgggcggacgcaagatgtgcaatctctctggcttagagcaggtcaagca ggcagcttggccaataaaatcgccatctacgatcaaattttaaaattgcgtcccgag gattgcgaagcattgacttataaggccgatgcggtactcgatatgggcgagccgcag tgggccgtcaatttatgtcagcaagcgttgaaaatcgaccctgaaaacggccatgct ttttaccaattggcttgtgcgtataccgcattggatcaatatgaagaggccgttaac tgtttatccgaagccttggcgcgtaccgaggattatcgcgataagtttgccgatgac cccgcgctgcaagcgttaaaaggttttgagccgt -continued LipL sequence (His6 tag is underlined) (SEQ ID NO: 3):
ATGGGTCATCATCATCATCATCATCTGGAAGTCCTGTTTCAAGGCCCGATGGCCTCG

CCGCGTGCGAACGATGCGCCGATTGTGCTGTTACATGGTTTTACGGGCTGGGGCCGG

GAAGAAATGCTGGGTTTCAAATACTGGGCGGCGTCCGCGGCGATATCGAACAATGG

TTGAATGATAATGGCTATCGCACCTATACCTTGGCCGTCGGCCCGTTGTCGAGCAAT

TGGGATCGCGCGTGCGAAGCGTATGCCCAATTGGTCGGCGGCACCGTCGATTATGGT

GCCGCGCATGCCGCGAATGATGGCCATGCCCGCTTTGGCCGCACCTATCCGGGCTTG

TTGCCGGAATTGAAACGCGGCGGCCGTGTCCATATCATTGCCCATAGCCAAGGCGGC

CAAACGGCCCGTATGTTGGTCTCGTTGTTGGAAAATGGCAGCCAAGAAGAACGCGAA

TATGCCAAAGAACATAATGTCTCGTTGAGCCCGTTGTTTGAAGGCGGCCATCGCTTC

GTCTTGTCGGTCACCACCATCGCCACCCCGCATGATGGCACCACCTTGGTCAATATG

GTCGATTTTACCGATCGCTTTTTCGATTTGCAAAAAGCCGTCTTGGAAGCCGCCGCA

GTCGCGTCGAATGCCCCGTACACCAGCGAAATTTATGATTTCAAATTGGATCAATGG

GGCTTGCGTCGCGAACCGGGCGAATCGTTTGATCATTATTTCGAACGCTTGAAACGC

TCGCCGGTCTGGACCAGCACGGATACGGCCCGCTATGATTTGAGCGTCCCGGGCGCC

GAAACCTTGAATCGCTGGGICAAAGCGTCGCCGAATACCTATTATTIGTCGTICAGC

ACCGAACGCACCTATCGTGGCGCCTTGACCGGCAATTATTATCCGGAATTGGGCATG

AATGCGTITICGGCCATCGTCTGCGCGCCGTTCTTGGGCAGCTATCGCAATGCGGCC

TTGGGCATTGATTCGCATTGGTTGGGCAATGATGGCATCGTCAATACCATTTCGATG

AATGGCCCGAAACGCGGCAGCAATGATCGCATCGTCCCGTATGATGGCACCITGAAG

AAAGGCGTCTGGAATGATATGGGCACCTATAAAGTCGATCATTTGGAAGTCATTGGC

GTCGATCCGAATCCGTCGTTCAACATTCGTGCGTTTTATCTGCGTTTAGCGGAACAA

CTGGCGTCCCTGCGTCCGTGA

Sequence of the S-laver protein (MALCv4 0971)-Lipase fusion
incorporated into Methylomicrobium alcaliphilum 20Z$^R$
chromosome. HRV protease site is single underlined (i.e., is
ctggaagtcctgtttcaaggcccg), and the lipase sequence is
shown bold (SEQ ID NO: 4):
atggcaacactctcagtggatatcgctcaatcctatatggagaccttacggtcctat gggcttgagtttaacataagacaaaccaacaacctgaccaatcggataattaaccgc ttggaaaatcgcggccacacacctgagcaagtagcagactggcttatgagcagggtt gcggttaaacagcaattgagaaaactggttaaacaaggcgaattggccgagtttgat ctggatggcaatggccgcctcaatcgatctgaattgctaaatgcaatgtctgctctg tccgagacagcggtcgaagaagcgccggtcgaagatcccacgactcccaagcctccg gccgatcctagcatcacgaccttaacgcttactgagattccgactcagcgtacggct acgttaaaatggaacaatgtcgatgccgatttggccatcgatttcatgcaagacgta ctgaaactagatctaaatcgactaggctggatggaagacggtcaattgaccgtcaac atcgacaatatcgcgatcagcgattcggacagtaattctgatatcaacatcggtatg gtcgatggcgaagaattttttgttcagcgtaaatacgccagtggcgctgtataccaat attatatttgatttgaagcaaaacgatgatgtcattcaaaccggcatcgtgctaacg ccgaccgaaaacaacggcggttcgtttgaaaacggcattacctccgatgccgacaac cacatcatcgccggtcgtcctgaattgctgcacggcgcctacatcgacggcggcggg ggctacaacacgttggaagtcgacatgaaaggcttctttgcgcagccgttccaactg -continued

```
ttgaacatccaagagatccacgtacaaaacctcccgaatgtctacagtttcgatcaa acaattttcagcgacaccgaaggcgactattttgctaattttccaattcctacgaat ttggatggcgatgatagcattcttgacttgagccgggccactagcctagaaagactg gtcattaacgaagcacgctttcccggtagcgcaaatgccttaggcgacctctacctg gtcggtatcaaagccgatgcggtcgcccgtctagaaggcaacttcaccgaagacgta aacttgttctatggtcgcggcttgggtaatgcgatcaacctggaatttgccaatgtc acgatgagtgatagtgagggggggggtgaattggtgctgggtcataatgccggtacc gtgaatctgctttccgaaggtcgtctgaacgtcttggaatctgttgatttcggtagt ttcctgcgcgaactcaccatcaccggtaccggagagttggttattgatgacgcctc gcattcgccttggcgaagtacatatcgatgcctctgctaataccggtggtattcgc ctcaaggtcgacagcgttgcagacggtagcagcctatccaatgaaatcggcttttct gcggttcttgacgaagtcaccatcaaaggctcacaaggtcgtgacgttatcgagatc tccggcactgctgcaggcgtattgcttgacatcgacaccggtgctggccgcgacacc gttttcttgaccgacgatactttgagtgctggcgctggctcagtgatcaccggtgat aatttgacagttgtggtgacagccaccgccgatctgcgtaaggccgatgttgttggc gttgaccgctttgtactgaatgcaggtcccgcagccgctggcaacctggttttgact cagacccaagtagaagccatggatgccggtgtgttcaccgcagcccataatactatc gcagttctgtcagtcgaaatcaccgaagcgggtacggttctgtcagatctgatcgat ctttcggcactgagcagtgatgttaagctggccttcaatgttgttaaaggtgcaagc cttgaaatgaccgctgaagaactgcataagtatgtagcttttgaaggcatcgatgca actatggctggtcacctggtgatcaccggtgcgggtctgggctttgatcctgaagat caatctgactacgatactggtggtacgattgccaattacggtcttacaccagaccaa aatatctccattattcgtgatccaaacggttttgagcgcccggcgcccgataccaac actgacatcctgaccattgataccacaggtggaatcaccatcggtgccaatgcactg tcagatgacgatgccttctcaaccaatgcaaccaccttgatcatcgaaggtgcaggt gatattacctttaatgcaccgttggaaatgttattagataactacaccatcgattt tccggcctgaccggcaatctcaatggcctgaccattctcgatttccagaacatcacg gatggaaacgatccgagcgactggggccagattatcggtaaccccgatgttaatacc cgtatcaacgtggtcattgaggacggtaaggaagttggtgatgacagtttaggcaat gccaatggcggcctcaagtcttccggtgtcgaaacctacgtagttctgggaactgtc ggcgaaacctacaccttcaatgtttgtgataccacgcaaggccttgaagtcctcggt ttccgtggtctgggtgatgtcacgttcaaccagatcaactggggcaccaacctgctg ctggaaggcgatggctttgaaaactttggtgatattccgaaggcttttgccaacccg aaccaatccaacatcggcagcatcgaagccaactacttcttcgatggtgctactgta gatgttgccatcaacaaccagggtcaagctctgggcaccacctctacaggggcagcg cgtcccttagtggtagaaaagcatcgtggtaaacggtgctgagaccgtaaacctggca atcgaagacggcagcgcctggatcaaatctgttgatggctctgttctcgaagatctg accgtcaccagtgatttccacgttacactctcgctgatcgctgccaacagcgacctc gaatctatcgatggatctggtgtcgtaggtgtcatggctctggagattagtgatgtt gatggcgccggggatcctactgccctgaccgtagacctctcttctacagaactgagc ggcatcgaccagatcgatctgggcccattggctgatctcactctgaacattgatcag
```

-continued

```
attgaggacatcggcacagcaaacatcgcctttaccggtacggctgcacaagctcaa aatgatccagcgacgctgaacattggtcagtttgctgaacaagagtttgatattacg acagtcggtctggaagccggtgttgaactgggtactgttacctttgttgcgaatgca ggtgaaatcactatgcatccagacaccaacctgtccggtgcaactgcaatcgtgatt ccagaaggcacaaccgtgaatatgacggctgcgcagtatgagcagatcgtagatggt ggaaacggtagcagcttctcaggcctcggtgtgttgaacatcaccgacctgctgggt gagcctgaactggatacaaatggtgatccgatcccaggagcctttgcttccgacatc aatctgtccggtgtacctgtcgaaatgatgggcagcatcagcctggcagcgggtgtc gatagcatgcgcctgacgggtaatatcggtatcgctcagtttgaagaaagggaaatt gctgatcctgataatacagacttcgtatcggttcagacttcgcataattttcatgaa ctgaccggcgaaacgcagggcttcagctttgtgctggccgaagatcagaacctgatc ttcaccacagaagcgcaggcccataaccgtgtggttgaaggcgatggctctaaagtc acgctggcgtttgctgtgctgctggactctcaggtcaacttcaatacgctgggcggc actcttgctgttgatggtctgaacctggcctactacagcgatttgaccgatcttgaa gtgcttcaggccttggtagctggtactaacgttgagcagatcctgggtaatctggat gaaaatacagttgttcagatttctgagtttattgctggcgctaactttgctaatccg actttccgcgatgtggaagtgttggaaggtgtaactgttgccggcggtctggtcttc gagaacctgaacgatgagttaccggatagcctcaagctgactgaactgagtctcagc ctgttgggtgatgcgactatcacaggtacggttgatattagtggtgcaccactgctg gatcagggcttcgaaaccctgaccatcaactcgctgggtgatgatcccaacaccatc aataatgtcgtagcgacaggcaacgatctgatcgatgtcgtgatcaatgctgaacag gatctgtcagttcaaaccatcaccttgagctttgttccaaaaacacctggtcaaaca tcagacgcaaccttgacagtcaatggtgatgcagatgtaaccatcaagacactggat agcactgatcctgatatcaacgtagttaacattgataacaacctgactggcggtgcc acactcaccttcacaggtggttcagctgcattcgagggtgatgatacagatagcctg atccttaccggtgcaggtaacactgtatttgatactgaaggtgcaagtacgggtggt atcgactccgatagcctgtcactgatcgatgcttctgagcacaccggtgatctggac ctgggtcgtatcatcagtgttgacgaagctaacttcagcctgctgacctccgccggt aatgcctcagctacgctgcaagccactatgaatgatcaaggctttaatgccgcggtc ctggcttacaacgccgctctggcagcggatcctgttgttccgggaaacgttactgca gcgctaactgctctaactactgctgcaggtcttcttggctttgtagatgcaaatgaa gatccgctggccttcactcaggctaacgcggctgatctgatcgcagagttccgtcct gaatggaactttgagctgggtgctaacaccgagctaaccatcgatggagatgacatc gttggagctgactttgttgccggtgccctggtgatatccggtggcaagttgatcatc gaaggtgaagtcgatctgcgtgatctggctgtactggacatctctgatgtcgagatt gagctggccgcaggtgcacgtatcctgatgactgacgagcagttcgacgcgctggac aacgtcaccttctctggcccaggtcagacgctggaagttgatgatgcgctgctggct gagctttctatcgtcaacgatatcactgatattcgcggtgtcactgagattcagttg gaagaaggcctggttgaagacatcaccatgacagctgagcaggcgcgtatcgcgact gtagtcgatgccgacggtaaccctgtcctggttgacttcgatgttgatccaactgtg
```

-continued

```
atcgatgctgcgggtgaccctgttgaagccggagacttccgtacccttacaggttct
gttgttaccgtcgaagtaacaggtaacgacgatctgaccgatctggctggcctgaat
cgcattgaaatcgtcagtgatgatctggttgatctgaaagtggcactggatcttgat
ggtgctaacaaccaggttgccgcgttgcaaactgcagcgggtgggagcgtttgacggc
acattcttcgatgtgttgagcaacttcactgttgaagcaagctttgaggtgctgagc
cagtttgaccctgaaaccacgttgttcgttgccaatccgatcgtggaggatgtcaac
ttcgacatcgtacgtgatgtgaatggtgatgtgacttcagtcagcgtcagcggtggc
tcttcccttggtttcgcccagagcgatgccggcttccaggagttgttggaagccggt
caggtaactgaggtggtgttcgagaatgttggttcactcaacagcatccttgttagt
ggcaacttcgtcggtagctacgatgccggtggtattttctacgagagcacctttgag
ttcggcgcaaatgctggttcggttgctgaaggggtgggtacagatggcaacatcttc
accattgctgaattcacagccggtgcagcagccagtgatatccttgatttcactgcc
atgcctgttgataacacgaacactgctccagccactgggcatgagttcatcgcggta
ggcactgaagctagcattggtgacgatgccaccatcattgtcttcacggcgggtgtt
gcggccgacgcagcaaccatcgtgacacagtttgctgatggtgcgggagatttccgt
tcagcagatgctactgcacgtaacgctgactttgctattgatagccagttgatcttc
ctgattgacgatggcgctggtaataccggtgtctggtattgggatgatacagttggt
gctgttggcgatggtattgtcgatgctgatgagctttcgcagattgcccagttgact
ggagtcgtcactgccgagctgacggttgataacttcgtcctcgctctggaagtcctg
tttcaaggcccgatggcctcgccgcgtgcgaacgatgcgccgattgtgctgttacat
ggttttacgggctggggccgggaagaaatgctgggtttcaaatactggggcggcgtc
cgcggcgatatcgaacaatggttgaatgataatggctatcgcacctataccttggcc
gtcggcccgttgtcgagcaattgggatcgcgcgtgcgaagcgtatgcccaattggtc
ggcggcaccgtcgattatggtgccgcgcatgccgcgaatgatggccatgccgctt
ggccgcacctatccgggcttgttgccggaattgaaacgcggcggccgtgtccatatc
attgcccatagccaaggcggccaaacggcccgtatgttggtctcgttgttggaaaat
ggcagccaagaagaacgcgaatatgccaaagaacataatgtctcgttgagcccgttg
tttgaaggcggccatcgcttcgtcttgtcggtcaccaccatcgccacccccgcatgat
ggcaccaccttggtcaatatggtcgatttaccgatcgcttttttcgatttgcaaaaa
gccgtcttggaagccgccgcagtcgcgtcgaatgccccgtacaccagcgaaatttat
gatttcaaattggatcaatggggcttgcgtcgcgaaccgggcgaatcgtttgatcat
tatttcgaacgcttgaaacgctcgccggtctggaccagcacggatacggcccgctat
gatttgagcgtcccgggcgccgaaaccttgaatcgctgggtcaaagcgtcgccgaat
acctattatttgtcgttcagcaccgaacgcacctatcgtggcgccttgaccggcaat
tattatccggaattgggcatgaatgcgttttcggccatcgtctgcgcgccgttcttg
ggcagctatcgcaatgcggccttgggcattgattcgcattggttgggcaatgatggc
atcgtcaataccatttcgatgaatgggccgaaacgcggcagcaatgatcgcatcgtc
ccgtatgatggcaccttgaagaaaggcgtctggaatgatatgggcacctataaagtc
gatcatttggaagtcattggcgtcgatccgaatccgtcgttcaacattcgtgcgttt
tatctgcgtttagcggaacaactggcgtccctgcgtccgtga
```

Example 3: Exemplary Methods and Compositions

This example provides exemplary methods for making compositions and bacterial cells as provided herein, and practicing methods as provided herein.

Producing Lipase Outside of the Cell as N-Terminal Fusion to S-Layer Protein.

Previous attempts to generate C-terminal fusion of lipase to S-layer resulted in no lipase activity and no S-layer in mutant cells. Upon thorough theoretical analysis, it was hypothesized that fusion of lipase to the N-terminus of S-layer proteins should solve the problem and be sufficient to ensure transporting of the fusion to outside of the cell.

Two genetic constructs comprising an exemplary recombinant polypeptide: (i) Green Florescent Protein (GFP) and (ii) L1 lipase fused to N-terminus of S layer protein were generated and introduced into 20Z chromosome (in a 20ZR-L1-SL strain).

Figure 12:
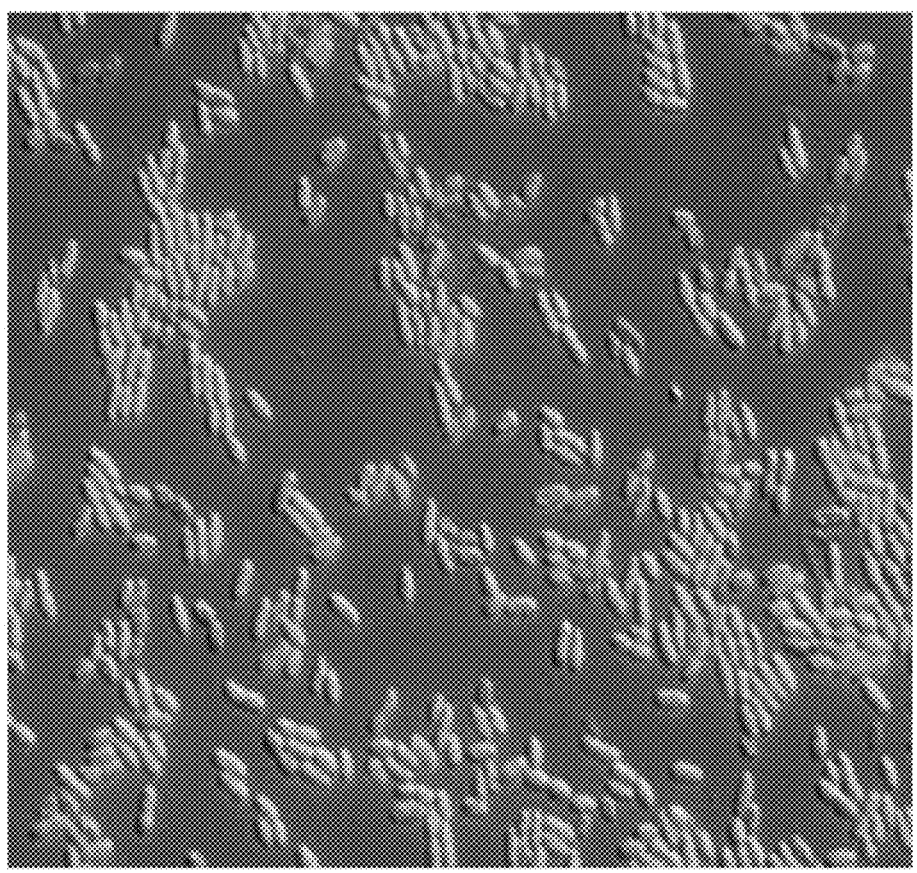
FIG. 12 illustrates an image of production of the GFP-comprising recombinant protein by the 20ZR-L1-SL strain, as described in detail in Example 3, below.

GFP-S layer fusion synthesizes active GFP which is distributed throughout whole cell volume which is in agreement with its putative outside localization, as illustrated in FIG. 12. Moreover, those cells excrete GFP-containing crystalline-like material which accumulates in extracellular media.

The strain TWC #11 (20$Z^R$::SL$_{Nter}$-LipL1, N-terminal fusion) yielded 133 U/g DCW of lipase, the majority of which was localized outside of the cell. The lipase is fused with S-layer and expected to co-purify with S-layers. Initial tests with the strain TWC #11 indicate SL$_{Nter}$-LipL1 fusion is loosely attached to the cell wall (Table 1). We tested a previously published protocol (see Shchukin V. N et al., 2011, Mikrobiologiya. 80: 595-605) for separating S-layers. Alternative protocols for S-layer separation can also be applied as described e.g., in Hasting and Brinton (1979); Sara, M, et al, J Bacteriol. 1998 August; 180(16): 4146-4153; or, Sleytr, U B, et al, FEMS Microbiol Rev. 2014 September; 38(5): 823-864.

Figure 13:
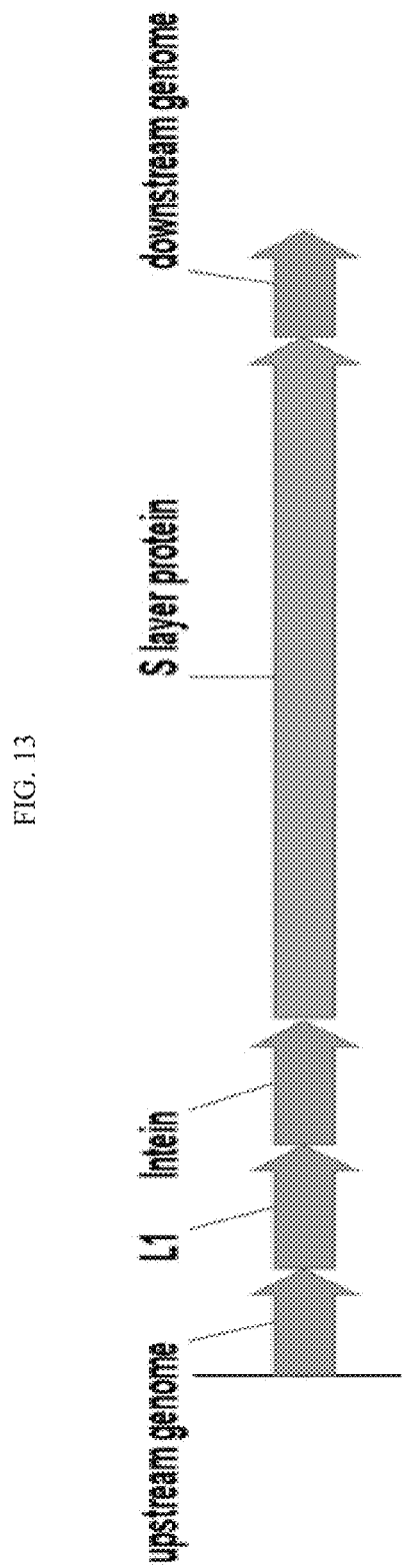
FIG. 13 schematically illustrates exemplary genetic constructs containing self-cleavable inteins, which were inserted between the lipase and the S-layer, as described in detail in Example 3, below.

Finally, we tested the applicability of inteins for protein expression. Two methanotrophic strains were made, and two genetic constructs containing self-cleavable intein were inserted between lipase and S-layer were made (as illustrated in FIG. 13, including:

(i) Mxe GyrA intein, which is activated by addition of thiol reagents like DTT, beta-ME, etc.; and, (ii) Ssp DnaB mini-intein, which is activated by pH shift to 6.0-7.0.

Figure 14:
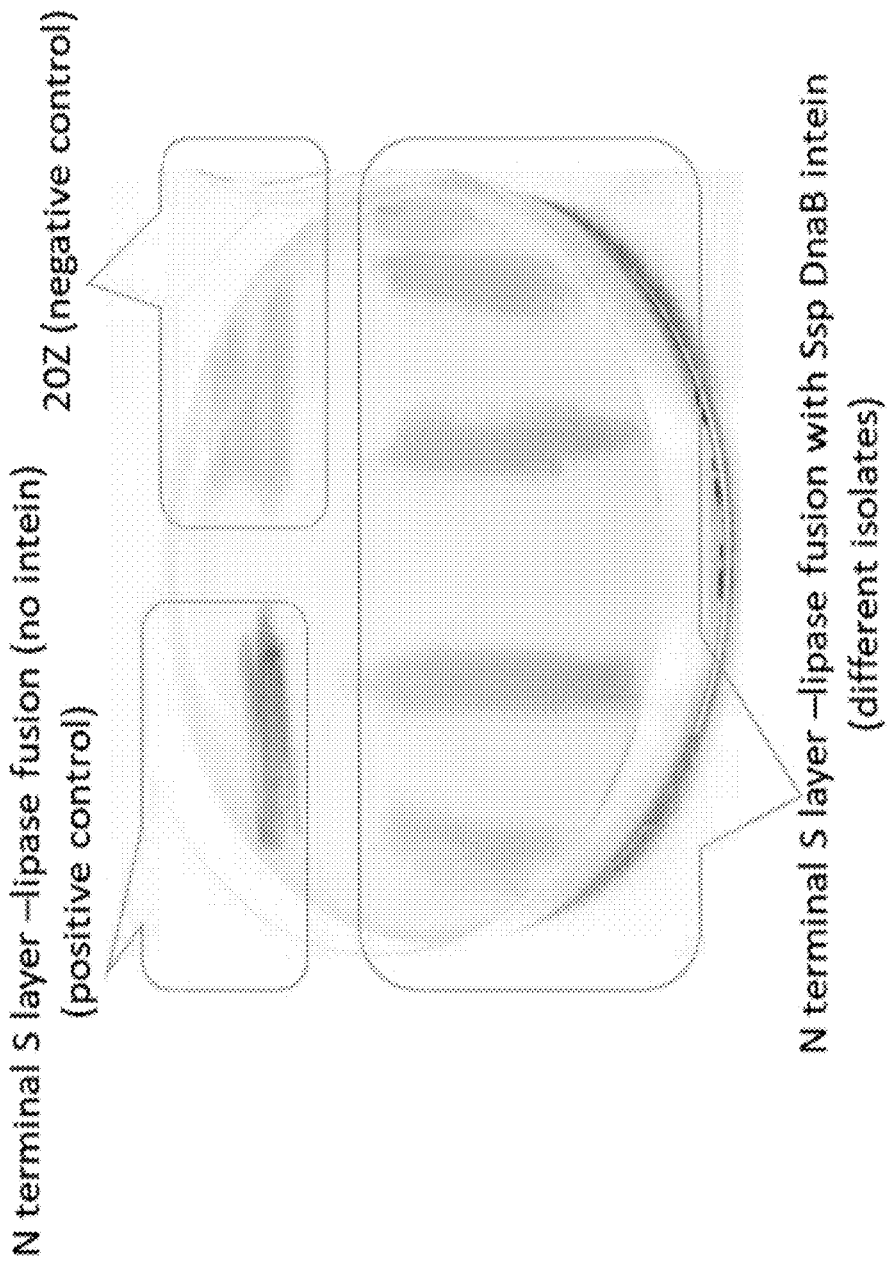
FIG. 14 illustrates an image of extracellular lipase localization and activity in a Rhodamine B assay with TWC #11 (top left of the plate), wild type (WT) (top right of the plate) and lipL-Ssp DnaB intein mutants (bottom of the plate), as described in detail in Example 3, below.

The strains of M. alcaliphilum 20$Z^R$ with Ssp DnaB mini-intein and Mxe GyrA intein were obtained. The strain Ssp DnaB intein showed lipase activity; however, the activity per dry cell weight was about 50-60% compared to N-terminal S-layer-lipase fusion (with no intein). About 70% of that activity is localized inside the cells in the soluble fraction, suggesting that the intein cuts inside of cells. The difference in extracellular lipase localization is illustrated as the Rhodamine B assay in FIG. 14, where the strong magenta color indicates lipase activity.

TABLE M4-1

Lipase activity as determine by p-nitrophenol assay.

|  | 20ZR::SL$_{Nter}$-LipL1 | 20ZR::SL$_{Nter}$-LipLI-ssp intein Mutant 1 | 20ZR::SL$_{Nter}$-LipL1-ssp intein Mutant 2 |
|---|---|---|---|
| whole cells (U/gDCW)* | 34.6 | 9.7 | 7.5 |
| supernatant | 8.3 | NT | NT |
| cytosol/envelops (U/mg protein) | 14.9 | 9.2 | 12.0 |
| cell debris (U/mg protein) | 0.6 | 1.4 | 4.5 |

*Whole cell assay-only cell-surface enzyme are active. SD ≤ 5%; NT, not tested.

These results lead us to conclude that the majority of lipase-Ssp DnaB mini-intein-S-layer protein fusions are self-cleaved inside the cell with only a minor fraction exported to the outer cell surface.

Figure 15:
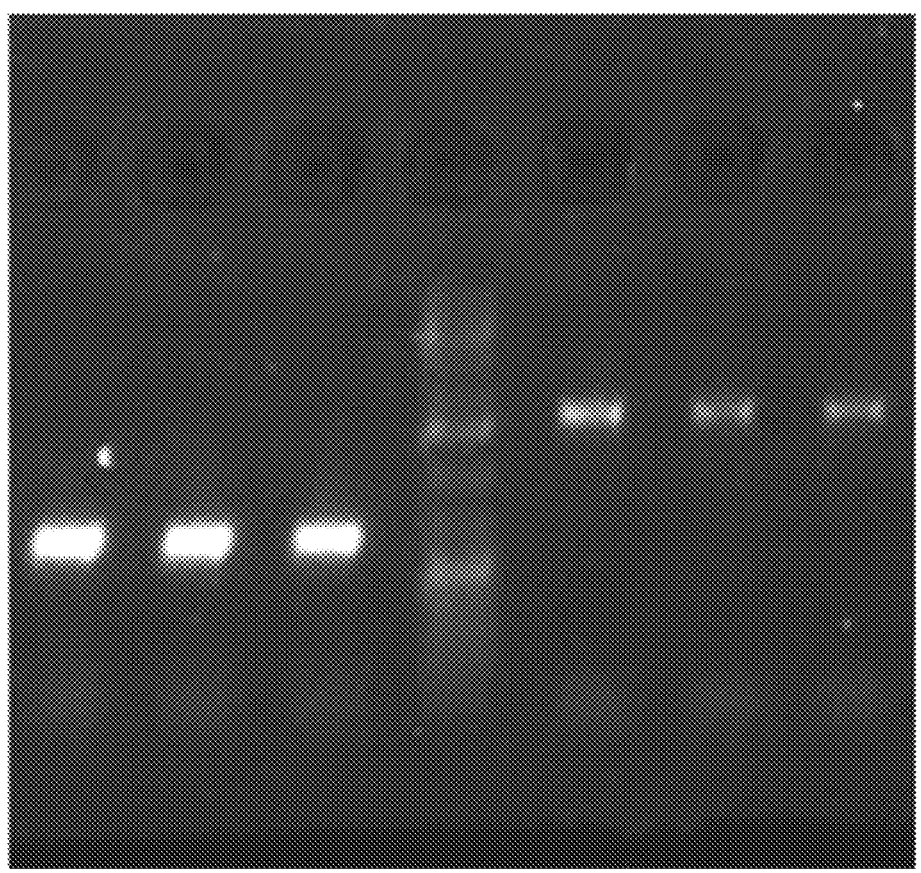
FIG. 15 illustrates an image of a gel separating amplified nucleic acid from a PCR-genotyping of TWC #G14 20ZR::$SL_{Nter}$-LipL1-Mxe GyrA strain.

Several mutants of 20$Z^R$ strain harboring LipL gene fused to S-layer protein via Mxe GyrA intein has been constructed. The genotyping of the strains was carried out, and we show that all mutants harbor the LipL (see FIG. 15, left), and the gene locates in correct orientation LipL-MxeGyrA-S-layer (see FIG. 15, right).

Since LipL-Mxe GyrA intein requires high concentrations of thiol reagents for cleavage, the chance of intracytoplasmic self-cleavage of that construct are minimal. An alternative approach for lipase expression includes the addition of a C-terminus to the lipase gene.

Expression of GFP Protein Fused to C-Term of S-Layer Protein

Figure 16:
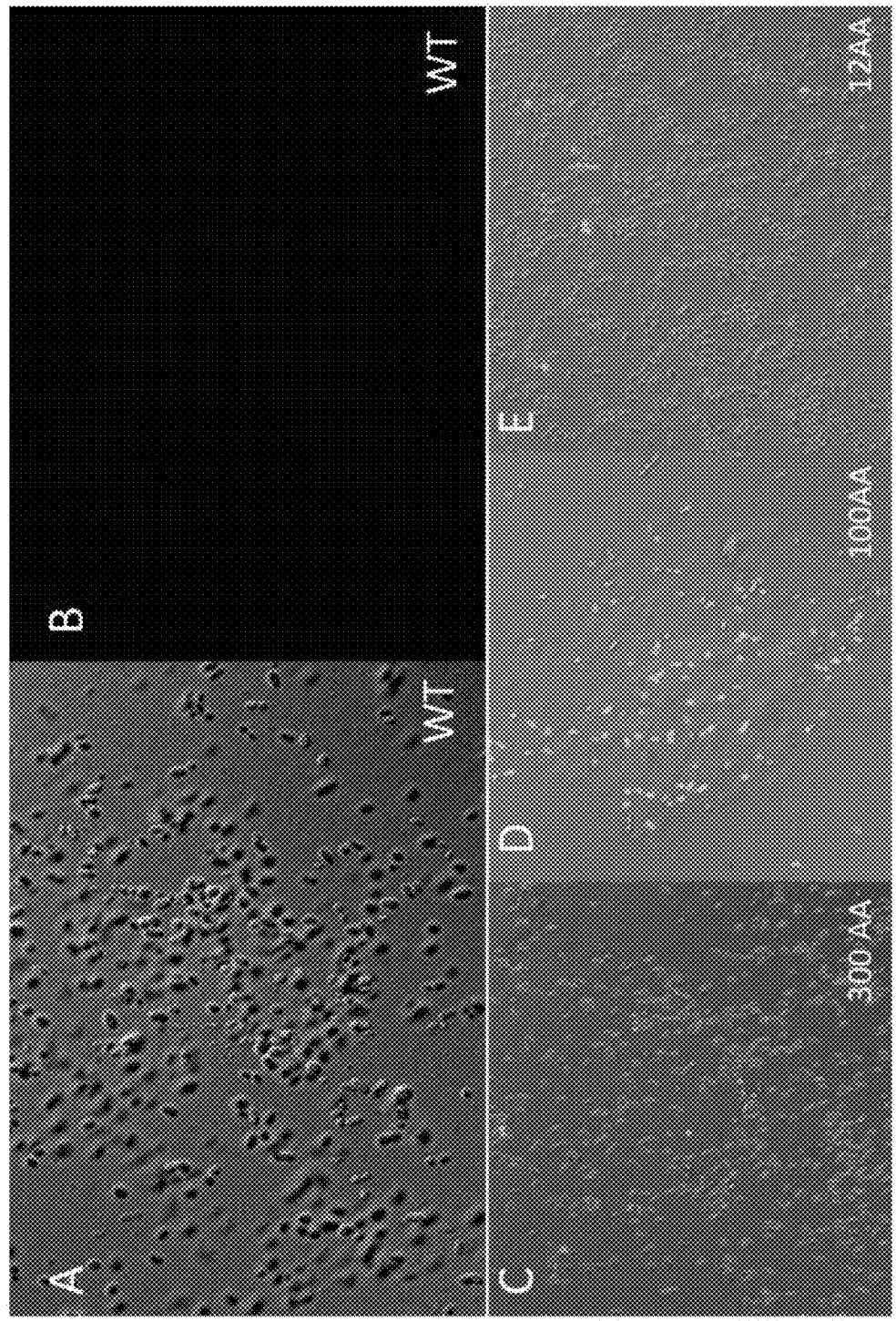
FIG. 16A-E illustrate images of cells harboring various GFP fusions.

We found that S-layer proteins are excreted via Type I secretion system. The benefits of this systems are as follows: typically proteins are produced and folded in cytosol; Type I secretion systems recognizes a specific tag at the C-term of a protein, upon recognition the protein is translocated from cytosol to extracellular environment. If efficient the system would enable direct production of the targeted proteins in cell culture. Several GFP construct fused with 900 bp, 300 bp, 108 bp and 36 bp of C-term of S-layer protein were made. The construct is expected to carry C-term recognition domain, which is used by Type I secretion system for the protein export outside of cells. Out of five constructs, three were obtained (900 bp, 300 bp, and 36 bp). The images of cells harboring GFP-fused proteins are shown in FIG. 16. Relative fluorescence of the supernatants was measured using a fluorimeter and background fluorescence in wild type cells compared with the construct strains, see Table 3, below. The GFP construct with 36 bp of S-layer C-term display highest fluorescens in supernatant, and has similar to other construct GFP per cell, indicating that the construct is efficiently exported from cells.

TABLE 3

Relative fluorescent units for GFP-fusions.

| C-term fusion | Supernatant (RFU) | RFU per cell (GFP/μm$^2$) |
|---|---|---|
| 300 AA (900 bp) | 1200 | 105.43 ± 120.82 |
| 100 AA (300 bp) | 3025 | 103.15 ± 38.68 |
| 12 AA (36 bp)* | 28899* | 110.31 ± 123.15 |
| WT | 1544 | none |

Exemplary Recombinant Polypeptide Sequences, as Discussed Above, are:

(noting that all the exemplary recombinant polypeptides, below, have C-terminal S layer protein domains)

Slayer$_{Nterm}$-L1lip fusion, sequence
(the following 3 domains are linked to constitute the complete recombinant protein, however, the individual domains are separated from each other, below, so that the sequence of each domain can be identified) (SEQ ID NO: 5):
upstream sequence, non-coding
tttaacattctaaatgggcgcaagtccgtataaatttaccacgaatcgggtttaatcgcagagcggcgaggcatcgtttacaa cccgcccggcaaagaaagtgttgtgggggcgacgcctacgtcgcgataaatcgaagtcgtgtcgctaatcgacaaaaca aacgtactcgaagcccctacggcacgaagcccggcagcgtagcggaattcgggaatggcctggctccgaactccccgg attgcgccatgctccatccgggctgcgctgtttagactcgccgaaagcggtcggtagcgatttatcagcgagaaaccttgtt aactttatgcgtatgggcgacaaccccgtccggcataagggcggcaaagaaagtgttgtgggagcgacgcctacgtcg cgataaatcgaagtcgtgtcgctaatcgacaaaacaaacggactcgaagcccctacggcacgaagcccggcagcgtagc ggaattcgggaatggcctggctccgaactccccggattgcgccatgctccatccgggctacgttgtttagactcgccgaaa gcggtcgctagcgatttatcagcgagaatctttgttagctttatgcgtatgggcgacaaccccgtccggcataagggcaac aaaaagttcagctatggaatcgatatatcgataaataaacaatgaaaaaacattttaattaaatcaaatatataaaacttaaatta cactaaaatacttcaatcatagtaatagaaagccaaattttaagcattatttcacccaaaataagggcggtccctagaaaaatt attaaaaactctctatactcaagcaccgtaagctatcaactcagtccagctctttacttagaaaggctgatcaaggtatagtgc atacaaaattcagtgcgtatcaaaacgtgtctagagttcttttctaacaaaaagcgaaaacctcaattggagatttaac L1 lipase
atggcctcgccgcgtgcgaacgatgcgccgattgtgctgttacatggttttacgggctggggccgggaagaaatgctgggt ttcaaatactggggcggcgtccgcggcgatatcgaacaatggttgaatgataatggctatcgcacctataccttggccgtcg gcccgttgtcgagcaattgggatcgcgcgtgcgaagcgtatgcccaattggtcggcggcaccgtcgattatggtgccgcg catgccgcgaatgatggccatgcccgctttggccgcacctatccgggcttgttgccggaattgaaacgcggcggccgtgtc catatcattgcccatagccaaggcggccaaacggcccgtatgttggtctcgttgttggaaaatggcagccaagaagaacgc gaatatgccaaagaacataatgtctcgttgagcccgttgtttgaaggcggccatcgcttcgtcttgtcggtcaccaccatcgc caccccgcatgatggcaccaccttggtcaatatggtcgattttaccgatcgcttttcgatttgcaaaaagccgtcttggaagc cgccgcagtcgcgtcgaatgccccgtacaccagcgaaatttatgatttcaaattggatcaatggggcttgcgtcgcgaacc gggcgaatcgtttgatcattatttcgaacgcttgaaacgctcgccggtctggaccagcacggatacggcccgctatgatttg agcgtcccgggcgccgaaaccttgaatcgctgggtcaaagcgtcgccgaatacctattatttgtcgttcagcaccgaacgc acctatcgtggcgccttgaccggcaattattatccggaattgggcatgaatgcgttttcggccatcgtctgcgcgccgttcttg ggcagctatcgcaatgcggccttgggcattgattcgcattggttgggcaatgatggcatcgtcaataccatttcgatgaatgg cccgaaacgcggcagcaatgatcgcatcgtcccgtatgatggcaccttgaagaaaggcgtctggaatgatatgggcacct ataaagtcgatcatttggaagtcattggcgtcgatccgaatccgtcgttcaacattcgtgcgttrtatctgcgtttagcggaaca actggcgtccctgcgtccg S layer protein (in-frame with L1 lip)
gcaacactctcagtggatatcgctcaatcctatatggagaccttacggtcctatgggcttgagtttaacataagacaaaccaa caacctgaccaatcggataattaaccgcttggaaaatcgcggccacacacctgagcaagtagcagactggcttatgagca gggttgcggttaaacagcaattgagaaaactggtaaacaaggcgaattggccgagtttgatctggatggcaatggccgcc tcaatcgatctgaattgctaaatgcaatgtctgctctgtccgagacageggtcgaagaagcgccggtcgaagatcccacga ctcccaagcctccggccgatcctagcatcacgaccttaacgcttactgagattccgactcagcgtacggctacgttaaaatg gaacaatgtcgatgccgatttggccatcgatttcatgcaagacgtactgaaactagatctaaatcgactaggctggatggaa gacggtcaattgaccgtcaacatcgacaatatcgcg atcagcgattcggacagtaattctgatatcaac atcggtatggtcga tggcgaagaattttttgttcagcgtaaatacgccagtggcgctgtataccaatattatatttgatttgaagcaaaacgatgatgtc -continued

```
attcaaaccggcatcgtgctaacgccgaccgaaaacaacggcggttcgtttgaaaacggcattacctccgatgccgacaa ccacatcatcgccggtcgtctgaattgctgcacggcgcctacatcgacggeggeggggggctacaacacgttggaagtcg acatgaaaggcttctttgcg
```

Slayer<sub>Nterm</sub>-L1lip-ssp DnaB intein fusion, sequence
(the following 4 domains are linked to constitute the complete recombinant protein,
however, the individual domains are separated from each other, below, so that the
sequence of each domain can be identified) (SEQ ID NO: 6):
upstream sequence, non-coding

```
tttaacattctaaatgggcgcaagtccgtataaatttaccacgaatcgggtttaatcgcagagcggcgaggcatcgttttacaa cccgcccggcaaagaaagtgttgtgggggcgacgcctacgtcgcgataaatcgaagtcgtgtcgctaatcgacaaaaca aacgtactcgaagcccctacggcacgaagcccggcagcgtagcggaattcgggaatggcctggctccgaactccccgg attgcgccatgctccatccgggctgcgctgtttagactcgccgaaagcggtcggtagcgatttatcagcgagaaaccttgtt aactttatgcgtatgggcgacaaccccgtccggcataagggcggcaaagaaagtgttgtgggagcgacgcctacgtcg cgataaatcgaagtcgtgtcgctaatcgacaaaacaaacggactcgaagcccctacggcacgaagcccggcagcgtagc ggaattcgggaatggc ctggctccgaactccccggattgcgccatgctccatccgggctacgttgtttagactcgccgaaa gcggtcgctagcgatttatcagcgagaatctttgttagctttatgcgtatgggcgacaaccccgtccggcataagggcaac aaaaagttcagctatgaatcgatatatcgataaataaacaatgaaaaaacattttaattaaatcaaatatataaaacttaaatta cactaaaatacttcaatcatagtaatagaaagccaaattttaagcattatttcacccaaaataagggcggtccctagaaaaatt attaaaaactctctatactcaagcaccgtaagctatcaactcagtccagctctttacttagaaaggctgatcaaggtatagtgc atacaaaattcagtgcgtatcaaaacgtgtctagagttctttctaacaaaaagcgaaaacctcaattggagatttaac
```

L1 lipase

```
atggcctcgccgcgtgcgaacgatgcgccgattgtgctgttacatggttttacgggctggggccgggaagaaatgctgggt ttcaaatactgggcggcgtccgcggcgatatcgaacaatggttgaatgataatggctatcgcacctataccttggccgtcg gcccgttgtcgagcaattgggatcgcgcgtgcgaagcgtatgcccaattggtcggeggcaccgtcgattatggtgccgcg catgccgcgaatgatggccatgcccgctttggccgcacctatccgggcttgttgccggaattgaaacgcggcggccgtgtc catatcattgcccatagccaaggeggccaaacggcccgtatgttggtctcgttgttggaaaatggcagccaagaagaacgc gaatatgccaaagaacataatgtctcgttgagcccgttgtttgaaggcggccatcgcttcgtcttgtcggtcaccaccatcgc caccccgcatgatggcaccaccttggtcaatatggtcgattttaccgatcgcttttttcgatttgcaaaaagccgtcttggaagc cgccgcagtcgcgtcgaatgccccgtacaccagcgaaatttatgatttcaaattggatcaatggggcttgcgtcgcgaacc gggcgaatcgtttgatcattatttcgaacgcttgaaacgctcgccggtctggaccagcacggatacggcccgctatgatttg agcgtcccgggcgccgaaaccttgaatcgctgggtcaaagcgtcgccgaataccattatttgtcgttcagcaccgaacgc acctatcgtggcgccttgaccggcaattattatccggaattgggcatgaatgcgttttcggccatcgtctgcgcgccgttcttg ggcagctatcgcaatgcggccttgggcattgattcgcattggttgggcaatgatggcatcgtcaataccatttcgatgaatgg cccgaaacgcggcagcaatgatcgcatcgtcccgtatgatggcaccttgaagaaaggcgtctggaatgatatgggcacct ataaagtcgatcatttggaagtcattggcgtcgatccgaatccgtcgttcaacattcgtgcgttttatctgcgtttagcggaaca actggcgtccctgcgtccg
```

Ssp DnaB intein

```
tgtagagcaatggccatcagcggcgattcgttgatctcgttggcctcgaccggcaaacgcgtcagcatcaaagatttgttgg atgaaaagatttcgaaatctgggccattaatgaacaaaccatgaaattggaaagcgcgaaagtctcgcgcgtcttctgcac cggcaaaaaattggtctatatcttgaaaacccgcttgggccgcaccattaaagccaccgcgaatcatcgcttttttgaccatcg atggctggaaacgcttggatgaattgagcttgaaagaacatattgccttgccgcgcaaattggaatcgtcgtcgttgcaattgt cgccggaaatcgaaaaattgagccaatcggatatttattgggatagcatcgtctcgattaccgaaaccggcgtcgaagaagt ctttgatttgaccgtcccgggcccgcataatttcgtcgcgaatgatattattgtccataat
```

-continued

S layer protein (in-frame with L1 lip)
Gcaacactctcagtggatatcgctcaatcctatatggagaccttacggtcctatgggcttgagtttaacataagacaaaccaa caacctgaccaatcggataattaaccgcttggaaaatcgcggccacacacctgagcaagtagcagactggcttatgagca gggttgcggttaaacagcaattgagaaaactggttaaacaaggcgaattggccgagtttgatctggatggcaatggccgcc tcaatcgatctgaattgctaaatgcaatgtctgctctgtccgagacagcggtcgaagaagcgccggtcgaagatcccacga ctcccaagcctccggccgatcctagcatcacgaccttaacgcttactgagattccgactcagcgtacggctacgttaaaatg gaacaatgtcgatgccgatttggccatcgatttcatgcaagacgtactgaaactagatctaaatcgactaggctggatggaa gacggtcaattgaccgtcaacatcgacaatatcgcgatcagcgattcggacagtaattctgatatcaacatcggtatggtcga tggcgaagaatttttgttcagcgtaaatacgccagtggcgctgtataccaatattatatttgatttgaagcaaaacgatgatgtc attcaaaccggcatcgtgctaacgccgaccgaaaacaacggcggttcgtttgaaaacggcattacctccgatgccgacaa ccacatcatcgccggtcgtcctgaattgctgcacggcgcctacatcgacggcggcgggggctacaacacgttggaagtcg acatgaaaggcttctttgcg Slayer$_{Nterm}$-L1lip-Mxe GyrA intein fusion, sequence
(the following 4 domains are linked to constitute the complete recombinant protein,
however, the individual domains are separated from each other, below, so that the
sequence of each domain can be identified) (SEQ ID NO: 7):
upstream sequence, non-coding
tttaacattctaaatgggcgcaagtccgtatataaatttaccacgaatcgggtttaatcgcagagcggcgaggcatcgttttacaa cccgcccggcaaagaaagtgttgtgggggcgacgcctacgtcgcgataaatcgaagtcgtgtcgctaatcgacaaaaca aacgtactcgaagcccctacggcacgaagcccggcagcgtagcggaattcgggaatggcctggctccgaactccccgg attgcgccatgctccatccgggctgcgctgtttagactcgccgaaagcggtcggtagcgatttatcagcgagaaaccttgtt aactttatgcgtatgggcgacaaccccgtccggcataagggcggcaaagaaagtgttgtgggagcgacgcctacgtcg cgataaatcgaagtcgtgtcgctaatcgacaaaacaaacggactcgaagcccctacggcacgaagcccggcagcgtagc ggaattcgggaatggcctggctccgaactccccggattgcgccatgctccatccgggctacgttgtttagactcgccgaaa gcggtcgctagcgatttatcagcgagaatctttgttagctttatgcgtatgggcgacaaccccgtccggcataagggcaac aaaaagttcagctatggaatcgatatatcgataaataaacaatgaaaaaacattttaattaaatcaaatatataaaacttaaatta cactaaaatacttcaatcatagtaatagaaagccaaattttaagcattatttcacccaaaataagggcggtccctagaaaaatt attaaaaactctctatactcaagcaccgtaagctatcaactcagtccagctctttacttagaaaggctgatcaaggtatagtgc atacaaaattcagtgcgtatcaaaacgtgtctagagttctttctaacaaaaagcgaaaacctcaattggagatttaac L1 lipase
atggcctcgccgcgtgcgaacgatgcgccgattgtgctgttacatggttttacgggctggggccgggaagaaatgctgggt ttcaaatactggggcggcgtccgcggcgatatcgaacaatggttgaatgataatggctatcgcacctataccttggccgtcg gcccgttgtcgagcaattgggatcgcgcgtgcgaagcgtatgcccaattggtcggcggcaccgtcgattatggtgccgcg catgccgcgaatgatggccatgcccgctttggccgcacctatccgggcttgttgccggaattgaaacgcggcggccgtgtc catatcattgcccatagccaaggcggccaaacggcccgtatgttggtctcgttgttggaaaatggcagccaagaagaacgc gaatatgccaaagaacataatgtctcgttgagcccgttgtttgaaggcggccatcgcttcgtcttgtcggtcaccaccatcgc caccccgcatgatggcaccaccttggtcaatatggtcgattttaccgatcgcttttcgatttgcaaaaagccgtcttggaagc cgccgcagtcgcgtcgaatgccccgtacaccagcgaaatttatgatttcaaattggatcaatggggcttgcgtcgcgaacc gggcgaatcgtttgatcattatttcgaacgcttgaaacgctcgccggtctggaccagcacggatacggcccgctatgatttg agcgtcccgggcgccgaaaccttgaatcgctgggtcaaagcgtcgccgaataacctattatttgtcgttcagcaccgaacgc acctatcgtggcgccttgaccggcaattattatccggaattgggcatgaatgcgttttcggccatcgtctgcgcgccgttcttg ggcagctatcgcaatgcggccttgggcattgattcgcattggttgggcaatgatggcatcgtcaataccatttcgatgaatgg -continued cccgaaacgcggcagcaatgatcgcatcgtcccgtatgatggcaccttgaagaaaggcgtctggaatgatatgggcacct ataaagtcgatcatttggaagtcattggcgtcgatccgaatccgtcgttcaacattcgtgcgttttatctgcgtttagcggaaca actggcgtccctgcgtccg Mxe GyrA intein
gcaatgcgcatgtgcatcaccggcgatgcgttggtcgccttgccggaaggcgaatcggtccgtattgccgatattgtcccg ggcgcccgtccgaatagcgataatgcgattgatttgaaagtcttggatcgtcatggcaatccggtcttggccgatcgcttgtt ccattcgggcgaacatccggtctataccgtccgtacggtcgaaggtttgcgtgtcacgggcaccgcgaatcatccgttgttg tgcttggtcgatgtcgccggcgtcccgaccttgttgtggaaattgatcgatgaaatcaaaccgggcgattatgcggtcatcca acgctcggccttttcggtcgattgcgccggttttgcccgtggcaaaccggaatttgccccgaccacctatacggtcggcgtc ccgggtttggtccgcttcttggaagcccatcatcgcgatccggatgcccaagcgatcgccgatgaattgaccgatggccgc ttttattatgcgaaagtcgcctcggtcacggatgcgggcgtccaaccggtctatagcttgcgcgtcgataccgcggatcatg cctttattaccaatggcttcgtcagccatgcc S layer protein (in-frame with L1 lip)
gcaacactctcagtggatatcgctcaatcctatatggagaccttacggtcctatgggcttgagtttaacataagacaaaccaa caacctgaccaatcggataattaaccgcttggaaaatcgcggccacacacctgagcaagtagcagactggcttatgagca gggttgcggttaaacagcaattgagaaaactggttaaacaaggcgaattggccgagtttgatctggatggcaatggccgcc tcaatcgatctgaattgctaaatgcaatgtctgctctgtccgagacageggtcgaagaagcgccggtcgaagatcccacga ctcccaagcctccggccgatcctagcatcacgaccttaacgcttactgagattccgactcagcgtacggctacgttaaaatg gaacaatgtcgatgccgatttggccatcgatttcatgcaagacgtactgaaactagatctaaatcgactaggctggatggaa gacggtcaattgaccgtcaacatcgacaatatcgcgatcagcgattggacagtaattctgatatcaacatcggtatggtcga tggcgaagaattttttgttcagcgtaaatacgccagtggcgctgtataccaatattatatttgatttgaagcaaaacgatgatgtc attcaaaccggcatcgtgctaacgccgaccgaaaacaacggcggttcgtttgaaaacggcattacctccgatgccgacaa ccacatcatcgccggtcgtcctgaattgctgcacggcgcctacatcgacggcggcgggggctacaacacgttggaagtcg acatgaaaggcttctttgcg

REFERENCES EXAMPLE 2

1. Anthony, C. 1982. The biochemistry of methylotrophs. London; New York: Academic Press 431p.
2. Demidenko A, et al. 2017. Fatty Acid Biosynthesis Pathways in *Methylomicrobium buryatense* 5G(B1). Front Microbiol. 17:2167.
3. Egelseer, E. M., et al. 2009. S-Layers, Microbial, Biotechnological Applications. in: *Encyclopedia of Industrial Biotechnology*, John Wiley & Sons, Inc.
4. Graf R, et al. 2008. The multifunctional role of ectoine as a natural cell protectant. Clin Dermatol. 26:326-33.
5. Henard C A, et al. 2016. Bioconversion of methane to lactate by an obligate methanotrophic bacterium. Sci Rep. 2016 6:21585. doi: 10.1038/srep21585.
6. He Y-Z, et al. 2015. High production of ectoine from aspartate and glycerol by use of whole-cell biocatalysis in recombinant *Escherichia coli*. Microbial Cell Factories 14:55.
7. Jeffries P, Wilkinson J F. Electron Microscopy of the cell wall complex of *Methylomonas albus*. Arch Microbiol 1978; 119:227-29.
8. Kalyuzhnaya M. G., Puri A., & Lidstrom M. E. 2015. Metabolic engineering in methanotrophic bacteria. Metab Eng. 29, 142-52.
9. Kim H K, et al. 1998. Gene cloning and characterization of thermostable lipase from *Bacillus stearothermophilus* L1. Biosci Biotechnol Biochem. 62(1):66-71.
10. Kim M H, et al. 2000. Thermostable lipase of *Bacillus Stearothermophilus*: high-level production, purification, and calcium-dependent thermostability. Biosci Biotechnol Biochem. 64:280-6.
11. Khmelenina, V. N., et al. 1992. The synthesis of polysaccharides by *Methylococcus capsulatus* under various conditions of cultivation. Mikrobiologiia (Russian). 61, 404-410.
12. Khmelenina V N, Kalyuzhnaya M G, Sakharovsky V G et al. Osmoadaptation in halophilic and alkaliphilic methanotrophs, *Arch Microbiol* 1999; 172:321-29.
13. Khmelenina V N, et al. Structural and functional features of methanotrophs from hypersaline and alkaline lakes. Microbiology (Russia) 2010; 9:472-82.
14. Mustakhimov I. I., et al. 2010. Identification and characterization of EctR, a new transcriptional regulator of the ectoine biosynthesis genes in the halotolerant methanotroph *Methylomicrobium alcaliphilum* 20Z. J. Bacteriol. 192, 410-7.
15. Ojala, D. S., et al. Genetic systems for moderately halo(alkali)philic bacteria of the genus *Methylomicrobium*. Methods Enzymol. Methods Enzymol. 495, 99-118.
16. Pastor J M, et al, 2010. Ectoines in cell stress protection: uses and biotechnological production. Biotechnol. Adv. 28 782-801.
17. Puri, A. W., et al. 2015. Genetic tools for the industrially promising methanotroph *Methylomicrobium buryatense*. Appl Environ Microbiol. 81, 1775-81.

18. Reshetnikov A S, et al. 2011. Genes and enzymes of ectoine biosynthesis in halotolerant methanotrophs. Methods in Enzymol. 495:15-30.
19. Riis, V., et al. 2003. Highly sensitive determination of ectoine and other compatible solutes by anion-exchange chromatography and pulsed amperometric detection. Anal. Bioanal. Chem. 377:203-207.
20. Strong P J, et al. 2016. A methanotroph-based biorefinery: Potential scenarios for generating multiple products from a single fermentation. Bioresour Technol. 215:314-23.
21. Trotsenko, Y. A., et al. Biotechnological potential of aerobic methylotrophic bacteria: a review of current state and future prospects. *Appl. Biochem. Microbiol.* 2005; 41, 433-441.
22. Vuilleumier S., et al. 2012. Genome Sequence of the Haloalkaliphilic Methanotrophic Bacterium *Methylomicrobium alcaliphilum* 20Z. J Bacteriol. 194, 551-2.

A number of embodiments of the invention have been described. Nevertheless, it will be understood that various modifications may be made without departing from the spirit and scope of the invention. Accordingly, other embodiments are within the scope of the following claims.

What is claimed is:

1. A method for making a chimeric S-layer fusion protein, or a self-aggregating or self-assembling fragment thereof, and a heterologous polypeptide or peptide, the method comprising:
   (a) recombinantly engineering a methylotrophic or methanotrophic bacteria to recombinantly express a chimeric fusion polypeptide comprising an S-layer polypeptide and a heterologous polypeptide or peptide,
   wherein the methylotrophic or methanotrophic bacteria comprises a type I secretion system,
   and the methylotrophic or methanotrophic bacteria is selected from the group consisting of a *Methylococcus*, a *Methylomonas*, a *Methylomicrobium*, a *Methylobacter*, a *Methylomarinum*, a *Methylovulum*, a *Methylocaldum*, a *Methylothermus*, a *Methylomarinovum*, a *Methylosphaera*, a *Methylocystis*, and a *Methylosinus* bacteria;
   and the S-layer polypeptide is derived from a methylotrophic or methanotrophic bacteria selected from the group consisting of a *Methylococcus*, a *Methylomonas*, a *Methylomicrobium*, a *Methylobacter*, a *Methylomarinum*, a *Methylovulum*, a *Methylocaldum*, a *Methylothermus*, a *Methylomarinovum*, a *Methylosphaera*, a *Methylocystis*, and a *Methylosinus* bacteria, and
   (b) culturing the recombinantly engineered methylotrophic or methanotrophic bacteria under culture conditions wherein the chimeric S-lay fusion protein is secreted extracellularly or is at least in part partially exposed to an extracellular environment or milieu by the recombinantly engineered methylotrophic or methanotrophic bacteria.

2. A method for displaying or immobilizing chimeric S-layer fusion proteins or a self aggregating or self-assembling fragment thereof on an engineered methylotrophic or methanotrophic bacteria, comprising:
   (a) recombinantly engineering a methylotrophic or methanotrophic bacteria to recombinantly express a chimeric fusion polypeptide comprising an S-layer polypeptide and a heterologous polypeptide or peptide,
   wherein the methylotrophic or methanotrophic bacteria comprises a type I secretion system,
   and the methylotrophic or methanotrophic bacteria is selected from the group consisting of a *Methylococcus*, a *Methylomonas*, a *Methylomicrobium*, a *Methylobacter*, a *Methylomarinum*, a *Methylovulum*, a *Methylocaldum*, a *Methylothermus*, a *Methylomarinovum*, a *Methylosphaera*, a *Methylocystis*, and a *Methylosinus* bacteria;
   and the S-layer polypeptide is derived from a methylotrophic or methanotrophic bacteria selected from the group consisting of a *Methylococcus*, a *Methylomonas*, a *Methylomicrobium*, a *Methylobacter*, a *Methylomarinum*, a *Methylovulum*, a *Methylocaldum*, a *Methylothermus*, a *Methylomarinovum*, a *Methylosphaera*, a *Methylocystis*, and a *Methylosinus* bacteria, and
   (b) culturing the recombinantly engineered methylotrophic or methanotrophic bacteria under culture conditions wherein the chimeric S-lay fusion protein is secreted extracellularly and immobilized, displayed or is at least in part partially exposed to an extracellular environment or milieu by the recombinantly engineered methylotrophic or methanotrophic bacteria.

3. The method of claim 1, wherein the chimeric S-layer fusion protein or self-aggregating or self-assembling fragment thereof comprises or is a lipoprotein.

4. The method of claim 1, wherein:
   the methylotrophic or methanotrophic bacteria is derived from a bacteria of the genus *Methylotuvimicrobium*; or,
   the S-layer polypeptide is derived from a methylotrophic or methanotrophic bacteria of the genus *Methylotuvimicrobium*.

5. The method of claim 1, wherein the methylotrophic or methanotrophic bacteria is a *Methylotuvimicrobium alcaliphilum* sp. 20Z.

6. The method of claim 1, wherein the chimeric S-layer fusion protein or self-aggregating or self-assembling fragment thereof, is expressed on the surface of a methylotrophic or methanotrophic bacteria, and the chimeric S-layer fusion protein or self-aggregating or self-assembling fragment thereof, is at least in part exposed to an extracellular environment or milieu.

7. The method of claim 1, wherein the recombinant or isolated chimeric S-layer fusion protein or self-aggregating or self-assembling fragment thereof, is isolated from the methylotrophic or methanotrophic bacteria.

8. The method of claim 1, wherein the chimeric S-layer fusion protein, comprises or is an enzyme, a structural protein, a fluorescent or a chemiluminescent protein, a ligand, a receptor, an antibody or antigen binding protein, or an antigen, a tolerogen or an immunogen.

9. The method of claim 8, wherein the enzyme is an industrial enzyme, or the enzyme is a lipase, a protease, a nitrogenase, a hydrogenase, a monooxygenase, an amylase, an isomerase, a cellulase or hemicellulase, a laccase, an epimerase, a decarboxylase, a glucanase or a fl-glucanase, a glucosidase, a phosphorylase, a phosphatase, a halogenase or a dehalogenase, a GlcNAc transferase, an N-acetylglucosamine, a GlcNAc transferase, a neuraminidase or sialidase, a nuclease, a peroxidase or an oxidase, or a metalloproteinase.

10. The method of claim 1, wherein the chimeric S-layer fusion protein or self-assembling fragment thereof, or the recombinant methylotrophic or methanotrophic bacteria, act as or are a part of: an ultrafiltration membrane; an affinity structure; nitrogen fixation; converting carbon dioxide into methane; methane uptake or methane oxidation; converting nitrogen gas to ammonia; a membrane of an enzyme membrane; a micro-carrier; a biosensor; a diagnostic device; a biocompatible surface; a vaccine; a device or composition for targeting, delivery and/or encapsulation; an anchor for extracellular production of a small molecule or a protein (optionally an enzyme or a structural protein), an enzymatic system for a bioremediation or a bio-mitigation, or a pharmaceutical or a protein-based biopharmaceutical.

11. A recombinant methylotrophic or methanotrophic bacteria, optionally a *Methylomicrobium alcaliphilum* (*M. alcaliphilum*), optionally a *M. alcaliphilum* sp. 20Z, for ectoine ((4S)-2-methyl-1,4,5,6-tetrahydropyrimidine-4-carboxylic acid) production or synthesis, wherein:
  (a) the recombinant or engineered methylotrophic or methanotrophic bacteria comprises an ectoine biosynthetic gene cluster organized as one operon (ectABC-ask), wherein the operon comprises genes encoding: a diaminobutyric acid (DABA) aminotransferase (EctB); a DABA acetyltransferase (EctA), and an ectoine synthase (EctC); and
  (b) the recombinant or engineered methylotrophic or methanotrophic bacteria:
    (i) is engineered to lack or not express a functional EctR1 repressor;
    (ii) comprises an isocitrate lyase/malate synthase fusion (transcriptionally controlled by a hps promoter (Phps); and/or,
    (iii) comprises one or more of the genetic modifications selected from the group consisting of:
      (1) deletion or inactivation of a MarR transcriptional regulator gene;
      (2) deletion or inactivation of a sucrose-phosphate synthase gene;
      (3) deletion or inactivation of a glycogen synthase 1 gene;
      (4) deletion or inactivation of a glycogen synthase cluster 2 gene;
      (5) deletion or inactivation of an amylosucrose gene;
      (6) deletion or inactivation of a gene for exopolysaccharide (EPS) biosynthesis;
      (7) deletion or inactivation of an ectoine hydrolase gene;
      (8) overexpression of a gene encoding for a lipase;
      (9) deletion or inactivation of an ectoine-R (EctR) gene;
      (10) deletion or inactivation of an ectoine-R (EctR) gene and overexpression of a lipase gene;
      (11) deletion or inactivation of an ectoine-R (EctR) gene and deletion or inactivation of a DoeA gene;
      (12) overexpression of an Icl/ms gene;
      (13) deletion or inactivation of: 20ZR SLCter-LipL1 ΔectR Δsps Δglg1 Δglg2 Δeps ΔdoeA::Popt-ectABC-icl-ms;
      (14) deletion or inactivation of: 20ZRΔectR Δsps Δglg1 Δglg2 Δeps ΔdoeA::Popt-ectABC-icl-ms;
      (15) expression of LipL from N-ter;
      (16) expression of LipL from N-ter with intein; and
      (17) expression of GFP with SLP C-term fusion.

12. The method of claim 11, wherein a doeA-gene encoding ectoine hydrolase is deleted or mutated such that a functional ectoine hydrolase is not expressed.

13. The method of claim 11, wherein the recombinant methylotrophic or methanotrophic bacteria further comprises an exogenous nucleic acid capable of expressing a methanotrophic lipase, or a functional lipase fragment thereof, in the recombinant methylotrophic or methanotrophic bacteria.

14. The method of claim 13, wherein:
  (a) the recombinant bacteria is engineered such that the ectoine and/or the lipase, or a functional lipase fragment thereof, is expressed as an S layer protein chimeric polypeptide; or
  (b) the methylotrophic or methanotrophic bacteria further comprises the ability to express: a heterologous or exogenous protein or enzyme, optionally an industrial enzyme; or a chimeric protein comprising an S-layer protein and the heterologous or exogenous protein or enzyme,
  wherein optionally the protein or enzyme is a lipase, a protease, a nitrogenase, a hydrogenase, a monooxygenase, an amylase, an isomerase, a cellulase or hemicellulase, a laccase, an epimerase, a decarboxylase, a glucanase or a fl-glucanase, a glucosidase, a phosphorylase, a phosphatase, a halogenase or a dehalogenase, a GlcNAc transferase, an N-acetylglucosamine, a GlcNAc transferase, a neuraminidase or sialidase, a nuclease, a peroxidase or an oxidase, or a metalloproteinase.

15. The method of claim 1, wherein the S-layer peptide is on the carboxy terminal end of the chimeric S-layer fusion protein.

16. The method of claim 1, wherein the chimeric S-layer fusion protein has assembled or is self-assembled to form a monomolecular layer.

17. The method of claim 2, wherein the S-layer protein or self-aggregating or self-assembling fragment thereof is on the carboxy terminal end of the chimeric S-layer fusion protein.

18. The method of claim 2, wherein the chimeric S-layer fusion protein or self-aggregating or self-assembling fragment thereof has assembled or is self-assembled to form a monomolecular layer.

19. The method of claim 1, further comprising isolating the chimeric S-layer fusion protein.

20. The method of claim 14, where the recombinant bacteria is engineered such that the ectoine and/or the lipase or the functional lipase fragment thereof is expressed as an lipase-S protein fusion protein, or the S-layer protein is positioned at the amino terminus.

* * * * *

SEQUENCE LISTING

```
<160> NUMBER OF SEQ ID NOS: 12

<210> SEQ ID NO 1
<211> LENGTH: 2216
<212> TYPE: DNA
<213> ORGANISM: Artificial Sequence
<220> FEATURE:
<223> OTHER INFORMATION: Synthetic: Genomic region of ectR (MALCv4_3251)
      with upstream and downstream flanks

<400> SEQUENCE: 1
gaaccgcttt gaacggccca accttcacca gcatttcggt ttcatgttga tctgcaaaat      60
ggcgtgtctc atcaaacatc acagcactgc caatttgagt gtccagtttt tttgccagcc     120
cctcaaacag agcccatgag gccttattat tcggagtaat ggtcgtctcg attcggttaa     180
tatcctgatt gaccggccgc gccagtatgg ctttcagcat ccgcgtggca agcccttggc     240
cacgggcttt ttcgccgaca gccacctgcc agacaaacag cgtatccgga cgttgcggaa     300
tacgataacc cgagacaaaa ccaaccaact catcgccaat tttggccgcc accgccgttt     360
cagaaaaatg gctgctctgc agcaaattgc agtacatcga attgggatcc aggggcgggc     420
atttgctaat cagccgatgc acctgcgctc cgacttcggc agtaggctgg ctaagtgtaa     480
taatcggcaa ggcagtttta tcaggcaaca tataaataac tctattattt agatttctgt     540
gcaattaact cggctttaac tgaataagcc gggctcgaat ttgatttttt atggccatca     600
gcacgaatat tctggcttca ttgaaaaaca taatatatag tacactaaat aatttaaatg     660
tccaggccgc gtacttttgc cttagattaa ttagatgtca tatcaaatta tgcctttcga     720
acttcaaatt tcggtagcgc cctaggatgc gccgggcgga gcaccgaatt ttgttcttcg     780
agggtataca ataatggctt tgtaacgcga cggcctctat ttcaatgatt ggtgatcaat     840
gatgcaaaac ccacaaccgc acgcccctca ttcgctggat acgctcgact tgaatccggt     900
tgaaaaggaa catttgctga atcaaattga agaagtactg gtcgcgttac gtagagtgat     960
tcgcgccacc gatttacact caaaatatct ggcaaaaacc actagcctga ccgcaccgca    1020
gattcttttg ttgcagacac tgcgcgccaa aggtcaactg accattggtg agctagctca    1080
ggacatgagt ctcagccaag cgactgtgac aacaattctg gatcgcctgg aaaaacgtca    1140
attggtgttc cggcagcgct cccagactga taaacgaaaa gtccatgtct atatgacgga    1200
ggcggccacg gaaatgctaa taaacgcccc tatccctttg caggatcgct ttacgcgaga    1260
attcagtaaa ctacaggaat gggaacaatt gatgattatt gcatcactgc aacgtgtcgc    1320
tcagatgatg gacgcgcaga acatccctgt cgctaaagaa gcgtttgatt ttccggttta    1380
agctctaata attcagctca gctgcaaccc gcatcacgct ttttcccaag ctccagcttg    1440
ggaaaaacac cccggaagct ccagcttcca gaaaccgaga taacctccgc acattctcaa    1500
```

| | |
|---|---|
| tcaaccccga ctcgctcgtt caatctttt cctgattagc aagatgcttc aacttgctga | 1560 |
| agccaattgt ccgagcagtg gccagtcgta gccacttctg cgggacgggt tatttaaccc | 1620 |
| atccccaacg tttcggtttg ccctaaacat ttcggctgac ttcggccaaa gtcaaaacgt | 1680 |
| ttaggacggg gctgcaaacc ccgtcctgct aaggatatgc tggttttcgg ctttagctg | 1740 |
| aagaaacttg ctaatcagga tcttttttga ttgtcgggaa gctagagctt cctgaataga | 1800 |
| ttacccaagc cggatcgctc gccgctatac acaaatatcg gtaaacttgc taaacagagg | 1860 |
| tcgccgtata cttggaagcg gtgctgtttg ataaatctgc ggatattgga catcagtggc | 1920 |
| ttcgaagtcg ggaacgttgg gcgataaaaa atggtatcga ggcctcattg gttaagattg | 1980 |
| caaaagggta attttgact tatgtataac gatgaggtaa ctattcagtc ccccggcaat | 2040 |
| tatcgttccc acgctctgcg tgggaatgcc tgagtaccgc tccagcggta cgagacgcta | 2100 |
| gagcgtctcg gtcttcattc ccacgccgga gcgtgagaac gataggcggt gtgaataatt | 2160 |
| acacgatgag agctggagct tgggtaacag cacaaaggca tatttagcct agttgc | 2216 |

<210> SEQ ID NO 2
<211> LENGTH: 2656
<212> TYPE: DNA
<213> ORGANISM: Artificial Sequence
<220> FEATURE:
<223> OTHER INFORMATION: Synthetic: Genomic region of doeA (MALCv4_3246) with upstream and downstream flanks

<400> SEQUENCE: 2

| | |
|---|---|
| gtagcaagcc ttgcgtagag attattgccg ggtgtaaagg cgtctatgct ttcgaggtgt | 60 |
| tcgatcaaaa catggccggc gagattcaca attacgatcg ggaaatcctg gggcaaattc | 120 |
| gccgcttcag agcgcatatt gtttccaaag atattaatgc caataccatt actcattatt | 180 |
| tgtctgccag tctgaaaaca attcgccgca tccgcgatgc cttgcaagaa atctatccgg | 240 |
| atgccgaaat caatcagcaa aaagtttcga ttgtttccgc catcggcagt gacatgaaaa | 300 |
| ttcccggtat tctggccaaa actgtctcgg cgctggcaga gaagcagatc agcgtgcttg | 360 |
| caatgcacca gtcaatgcgt caagtcgata tgcagtttgt gattgatgaa gatgcctaca | 420 |
| ctgatgcgat gaaaagtttg cattgtcatc tggtggaggt ccatgatcac ggcattgcaa | 480 |
| tatgcctcgc gtcctgattg tactgatgtt tcttacccct aaatacgggg aaatttctca | 540 |
| aactgggaat tgctgccaaa gaaatgaaaa tgccttgcgt cttcagtctt gcgctgaacg | 600 |
| acaaggaagc gcataaggct taaagcgttt accactcgac cgctgaagcg gtagcggatt | 660 |
| aaggcgagtc gcaagtcaat tttcgtccaa ggttaggttg ttcatggcaa gtcagtcgag | 720 |
| caatgaatga cttaaccgtc tatttttcaa taaactgaag atgtacgggt aagccctgcg | 780 |
| taagttggga atgccgatg atcgagggct atctgttgtc gcgaagtctt taatcaaaaa | 840 |
| aatgggttta atattcaatg attaccgaga atgccgcaca gtccgaacaa agtgaagatt | 900 |
| tttatcaatc acgtaacggt agtaagccga aaataattcc gcgcgtagac ccggtagttt | 960 |
| atgcgcaaac agctaatcca ggtctcattg cagaggactt gcaagcacgt tatgagcaac | 1020 |
| aaggttttct tgttattgat aatgttttta atgagaggga ggtcgactgt ttcaagcaag | 1080 |
| agctcaaacg cttgaacgac gatgaaaaga taaaagcctc ggcggaagcg ataactgaat | 1140 |
| tatccagcga cgaactccgt tcactattta aaattcatga agtcagtccg gtttttaaaa | 1200 |
| ggttagctgc cgataatcga ttagcgggac tggctcaaca tcttttgaac gaccgggttt | 1260 |
| atattcatca gtcgcgctta aactataagc cgggttttcg cggcaaggaa ttttactggc | 1320 |

```
attcggactt tgaaacttgg catgtagaag acggtatgcc tagaatgcgt gcgctcagca    1380
tgtccattat tcttaccgaa aacgatcagc ataacgggcc tttgatgttg gttcccggat    1440
cgcataaaaa atttgtcgtt tgcgaagagg aaacgccgga aaatcattat tcggtctcgt    1500
tgaaaaagca ggagtacggc atacccagcg atgaatgctt ggctagcttg gttgccgatg    1560
gcggcatcgt atcggccaat ggaaaacccg gcagtgtctt gattttcgac agtaatgtca    1620
tgcacggttc gaatagtaat atcactccat ggcctcgctc gaatctcttt ttcgtctata    1680
acgcgatcaa taatcgagta acatggccgt tttgcggttt attgccgcgt cctgaatatc    1740
tttgcagtcg caagaatata cgagttatcg aaccgcggcc ttttatcgcg gccgccgatc    1800
aattgatata tgcttagaat gttaataatg ttgatcgtgc tggcgccctg ttccgtgttg    1860
ggcgagagcg tcaacgatga agcagaggtt caagagcgct tagatgcggt tgaatctttg    1920
gataagcctt tatatagtcc gttcatcgag cgctatatgc tggatgaact caaacaattg    1980
cgtatggaca tggcagcgca gaggaatgag ctgattcagc aaattgtgga tagagagctt    2040
agctcggtcg atagaggcgt tacttacgcc actaatactg tcacatattt tttctacttg    2100
attgccggtg ccagtaccat tttggtgttg ctgggttgga cctcgctcag agatatcaaa    2160
gagcgtgtgc agtccatggc ggataagaaa gtatcgaaac tggtccatga atacgaagag    2220
cgcttggcaa ttgtcgaaca acaactcaac aaggaagcac aattgattga gaaaatcggc    2280
gaggatatcg gcggacgca agatgtgcaa tctctctggc ttagagcagg tcaagcaggc    2340
agcttggcca ataaaatcgc catctacgat caaattttaa aattgcgtcc cgaggattgc    2400
gaagcattga cttataaggc cgatgcggta ctcgatatgg gcgagccgca gtgggccgtc    2460
aatttatgtc agcaagcgtt gaaaatcgac cctgaaaacg gccatgcttt ttaccaattg    2520
gcttgtgcgt ataccgcatt ggatcaatat gaagaggccg ttaactgttt atccgaagcc    2580
ttggcgcgta ccgaggatta tcgcgataag tttgccgatg accccgcgct gcaagcgtta    2640
aaaggttttg agccgt                                                    2656

<210> SEQ ID NO 3
<211> LENGTH: 1218
<212> TYPE: DNA
<213> ORGANISM: Artificial Sequence
<220> FEATURE:
<223> OTHER INFORMATION: Synthetic: LipL sequence

<400> SEQUENCE: 3
atgggtcatc atcatcatca tcatctggaa gtcctgtttc aaggcccgat ggcctcgccg      60
cgtgcgaacg atgcgccgat tgtgctgtta catggtttta cgggctgggg ccgggaagaa     120
atgctgggtt tcaaatactg gggcggcgtc cgcggcgata tcgaacaatg gttgaatgat     180
aatggctatc gcacctatac cttggccgtc ggcccgttgt cgagcaattg ggatcgcgcg     240
tgcgaagcgt atgcccaatt ggtcggcggc accgtcgatt atggtgccgc gcatgccgcg     300
aatgatggcc atgcccgctt ggccgcacc tatccgggct tgttgccgga attgaaacgc     360
ggcggccgtg tccatatcat tgcccatagc caaggcggcc aaacggcccg tatgttggtc     420
tcgttgttgg aaaatggcag ccaagaagaa cgcgaatatg ccaaagaaca taatgtctcg     480
ttgagcccgt tgtttgaagg cggccatcgc ttcgtcttgt cggtcaccac catcgccacc     540
ccgcatgatg caccaccttt ggtcaatatg tcgattttta ccgatcgctt tttcgatttg     600
caaaaagccg tcttggaagc cgccgcagtc gcgtcgaatg ccccgtacac cagcgaaatt     660 tatgattca aattggatca atggggcttg cgtcgcgaac cgggcgaatc gtttgatcat     720
```

-continued

```
tatttcgaac gcttgaaacg ctcgccggtc tggaccagca cggatacggc ccgctatgat      780
ttgagcgtcc cgggcgccga aaccttgaat cgctgggtca aagcgtcgcc gaatacctat      840
tatttgtcgt tcagcaccga acgcacctat cgtggcgcct tgaccggcaa ttattatccg      900
gaattgggca tgaatgcgtt ttcggccatc gtctgcgcgc cgttcttggg cagctatcgc      960
aatgcggcct tgggcattga ttcgcattgg ttgggcaatg atggcatcgt caataccatt     1020
tcgatgaatg ccccgaaacg cggcagcaat gatcgcatcg tcccgtatga tggcaccttg     1080
aagaaaggcg tctggaatga tatgggcacc tataaagtcg atcatttgga agtcattggc     1140
gtcgatccga atccgtcgtt caacattcgt gcgttttatc tgcgtttagc ggaacaactg     1200
gcgtccctgc gtccgtga                                                    1218
```

<210> SEQ ID NO 4
<211> LENGTH: 7737
<212> TYPE: DNA
<213> ORGANISM: Artificial Sequence
<220> FEATURE:
<223> OTHER INFORMATION: Synthetic: Sequence of the S-layer protein
(MALCv4_0971)-Lipase fusion incorporated into Methylomicrobium
alcaliphilum 20ZR chromosome

<400> SEQUENCE: 4

```
atggcaacac tctcagtgga tatcgctcaa tcctatatgg agaccttacg gtcctatggg       60
cttgagttta acataagaca aaccaacaac ctgaccaatc ggataattaa ccgcttggaa      120
aatcgcggcc acacacctga gcaagtagca gactggctta tgagcagggt tgcggttaaa      180
cagcaattga gaaaactggt taaacaaggc gaattggccg agtttgatct ggatggcaat      240
ggccgcctca atcgatctga attgctaaat gcaatgtctg ctctgtccga cagcggtc       300 gaagaagcgc cggtcgaaga tcccacgact cccaagcctc cggccgatcc tagcatcacg      360
accttaacgc ttactgagat tccgactcag cgtacggcta cgttaaaatg aacaatgtc      420 gatgccgatt tggccatcga tttcatgcaa gacgtactga aactagatct aaatcgacta      480
ggctggatgg aagacggtca attgaccgtc aacatcgaca atatcgcgat cagcgattcg      540
gacagtaatt ctgatatcaa catcggtatg gtcgatggcg aagaattttt gttcagcgta      600
aatacgccag tggcgctgta taccaatatt atatttgatt tgaagcaaaa cgatgatgtc      660
attcaaaccg gcatcgtgct aacgccgacc gaaaacaacg gcggttcgtt tgaaaacggc      720
attacctccg atgccgacaa ccacatcatc gccggtcgtc ctgaattgct gcacggcgcc      780
tacatcgacg gcggcggggg ctacaacacg ttggaagtcg acatgaaagg cttctttgcg      840
cagccgttcc aactgttgaa catccaagag atccacgtac aaaacctccc gaatgtctac      900
agtttcgatc aaacaatttt cagcgacacc gaaggcgact attttgctaa ttttccaatt      960
cctacgaatt tggatggcga tgatagcatt cttgacttga gccgggccac tagcctagaa     1020
agactggtca ttaacgaagc acgctttccc ggtagcgcaa atgccttagg cgacctctac     1080
ctggtcggta tcaaagccga tgcggtcgcc cgtctagaag gcaacttcac cgaagacgta     1140
aacttgttct atggtcgcgg cttgggtaat gcgatcaacc tggaatttgc caatgtcacg     1200
atgagtgata gtgaggggg gggtgaattg gtgctgggtc ataatgccgg taccgtgaat     1260
ctgctttccg aaggtcgtct gaacgtcttg gaatctgttg atttcggtag tttcctgcgc     1320
gaactcacca tcaccggtac cggagagttg gttattgatg acgccctcgc attcgccttt     1380
ggcgaagtac atatcgatgc ctctgctaat accggtggta ttcgcctcaa ggtcgacagc     1440
```

-continued

```
gttgcagacg gtagcagcct atccaatgaa atcggctttt ctgcggttct tgacgaagtc    1500
accatcaaag gctcacaagg tcgtgacgtt atcgagatct ccggcactgc tgcaggcgta    1560
ttgcttgaca tcgacaccgg tgctggccgc gacaccgttt tcttgaccga cgatactttg    1620
agtgctggcg ctggctcagt gatcaccggt gataatttga cagttgtggt gacagccacc    1680
gccgatctgc gtaaggccga tgttgttggc gttgaccgct ttgtactgaa tgcaggtccc    1740
gcagccgctg gcaacctggt tttgactcag acccaagtag aagccatgga tgccggtgtg    1800
ttcaccgcag cccataatac tatcgcagtt ctgtcagtcg aaatcaccga agcgggtacg    1860
gttctgtcag atctgatcga tctttcggca ctgagcagtg atgttaagct ggccttcaat    1920
gttgttaaag gtgcaagcct tgaaatgacc gctgaagaac tgcataagta tgtagctttt    1980
gaaggcatcg atgcaactat ggctggtcac ctggtgatca ccggtgcggg tctgggcttt    2040
gatcctgaag atcaatctga ctacgatact ggtggtacga ttgccaatta cggtcttaca    2100
ccagaccaaa atatctccat tattcgtgat ccaaacggtt ttgagcgccc ggcgccgat    2160 accaacactg acatcctgac cattgatacc acaggtggaa tcaccatcgg tgccaatgca    2220
ctgtcagatg acgatgcctt ctcaaccaat gcaaccacct tgatcatcga aggtgcaggt    2280
gatattacct ttaatgcacc gttggaaatg ttattagata actacaccat cgattttcc    2340 ggcctgaccg gcaatctcaa tggcctgacc attctcgatt ccagaacat cacggatgga    2400 aacgatccga gcgactgggg ccagattatc ggtaaccccg atgttaatac ccgtatcaac    2460
gtggtcattg aggacggtaa ggaagttggt gatgacagtt taggcaatgc caatggcggc    2520
ctcaagtctt ccggtgtcga aacctacgta gttctgggaa ctgtcggcga aacctacacc    2580
ttcaatgttt gtgataccac gcaaggcctt gaagtcctcg gtttccgtgg tctgggtgat    2640
gtcacgttca accagatcaa ctgggccacc aacctgctgc tggaaggcga tggctttgaa    2700
aactttggtg atattccgaa ggcttttgcc aacccgaacc aatccaacat cggcagcatc    2760
gaagccaact acttcttcga tggtgctact gtagatgttg ccatcaacaa ccagggtcaa    2820
gctctgggca ccacctctac aggggcagcg cgtcccttag tggtagaaag catcgtggta    2880
aacggtgcta gaccgtaaa cctggcaatc gaagacggca gcgcctggat caaatctgtt    2940
gatggctctg ttctcgaaga tctgaccgtc accagtgatt ccacgttac actctcgctg    3000 atcgctgcca acagcgacct cgaatctatc gatggatctg gtgtcgtagg tgtcatggct    3060
ctggagatta gtgatgttga tggcgccggg gatcctactg ccctgaccgt agacctctct    3120
tctacagaac tgagcggcat cgaccagatc gatctgggcc cattggctga tctcactctg    3180
aacattgatc agattgagga catcggcaca gcaaacatcg cctttaccgg tacggctgca    3240
caagctcaaa atgatccagc gacgctgaac attggtcagt tgctgaaca agagtttgat    3300 attacgacag tcggtctgga agccggtgtt gaactgggta ctgttacctt tgttgcgaat    3360
gcaggtgaaa tcactatgca tccagacacc aacctgtccg gtgcaactgc aatcgtgatt    3420
ccagaaggca caaccgtgaa tatgacggct gcgcagtatg agcagatcgt agatggtgga    3480
aacggtagca gcttctcagg cctcggtgtg ttgaacatca ccgacctgct gggtgagcct    3540
gaactggata caaatggtga tccgatccca ggagcctttg cttccgacat caatctgtcc    3600
ggtgtacctg tcgaaatgat gggcagcatc agcctggcag cgggtgtcga tagcatgcgc    3660
ctgacgggta atatcggtat cgctcagttt gaagaaaggg aaattgctga tcctgataat    3720
acagacttcg tatcggttca gacttcgcat aattttcatg aactgaccgg cgaaacgcag    3780
ggcttcagct ttgtgctggc cgaagatcag aacctgatct tcaccacaga agcgcaggcc    3840
```

```
cataaccgtg tggttgaagg cgatggctct aaagtcacgc tggcgttttgc tgtgctgctg    3900
gactctcagg tcaacttcaa tacgctgggc ggcactcttg ctgttgatgg tctgaacctg    3960
gcctactaca gcgatttgac cgatcttgaa gtgcttcagg ccttggtagc tggtactaac    4020
gttgagcaga tcctgggtaa tctgatgaa aatacagttg ttcagatttc tgagtttatt    4080
gctggcgcta actttgctaa tccgactttc cgcgatgtgg aagtgttgga aggtgtaact    4140
gttgccggcg tctggtctt cgagaacctg aacgatgagt taccggatag cctcaagctg    4200
actgaactga gtctcagcct gttgggtgat gcgactatca caggtacggt tgatattagt    4260
ggtgcaccac tgctggatca gggcttcgaa accctgacca tcaactcgct gggtgatgat    4320
cccaacacca tcaataatgt cgtagcgaca ggcaacgatc tgatcgatgt cgtgatcaat    4380
gctgaacagg atctgtcagt tcaaaccatc accttgagct tgttccaaa aacacctggt    4440
caaacatcag acgcaacctt gacagtcaat ggtgatgcag atgtaaccat caagacactg    4500
gatagcactg atcctgatat caacgtagtt aacattgata caacctgac tggcggtgcc    4560
acactcacct tcacaggtgg ttcagctgca ttcgagggtg atgatacaga tagcctgatc    4620
cttaccggtg caggtaacac tgtatttgat actgaaggtg caagtacggg tggtatcgac    4680
tccgatagcc tgtcactgat cgatgcttct gagcacaccg gtgatctgga cctgggtcgt    4740
atcatcagtg ttgacgaagc taacttcagc ctgctgacct ccgccggtaa tgcctcagct    4800
acgctgcaag ccactatgaa tgatcaaggc tttaatgccg cggtcctggc ttacaacgcc    4860
gctctggcag cggatcctgt tgttccggga aacgttactg cagcgctaac tgctctaact    4920
actgctgcag gtcttcttgg cttttgtagat gcaaatgaag atccgctggc cttcactcag    4980
gctaacgcgg ctgatctgat cgcagagttc cgtcctgaat ggaactttga gctgggtgct    5040
aacaccgagc taaccatcga tggagatgac atcgttggag ctgactttgt tgccggtgcc    5100
ctggtgatat ccggtggcaa gttgatcatc gaaggtgaag tcgatctgcg tgatctggct    5160
gtactggaca tctctgatgt cgagattgag ctggccgcag gtgcacgtat cctgatgact    5220
gacgagcagt tcgacgcgct ggacaacgtc accttctctg gcccaggtca gacgctggaa    5280
gttgatgatg cgctgctggc tgagcttttct atcgtcaacg atatcactga tattcgcggt    5340
gtcactgaga ttcagttgga agaaggcctg gttgaagaca tcaccatgac agctgagcag    5400
gcgcgtatcg cgactgtagt cgatgccgac ggtaaccctg tcctggttga cttcgatgtt    5460
gatccaactg tgatcgatgc tgcgggtgac cctgttgaag ccggagactt ccgtacccct    5520
acaggttctg ttgttaccgt cgaagtaaca ggtaacgacg atctgaccga tctggctggc    5580
ctgaatcgca ttgaaatcgt cagtgatgat ctggttgatc tgaaagtggc actggatctt    5640
gatggtgcta caaccaggt tgccgcgttg caaactgcag cgggtggagc gtttgacggc    5700
acattcttcg atgtgttgag caacttcact gttgaagcaa gctttgaggt gctgagccag    5760
tttgaccctg aaaccacgtt gttcgttgcc aatccgatcg tggaggatgt caacttcgac    5820
atcgtacgtg atgtgaatgg tgatgtgact tcagtcagcg tcagcggtgg ctcttccctt    5880
ggtttcgccc agagcgatgc cggcttccag gagttgttgg aagccggtca ggtaactgag    5940
gtggtgttcg agaatgttgg ttcactcaac agcatccttg ttagtggcaa cttcgtcggt    6000
agctacgatg ccggtggtat tttctacgag agcaccttttg agttcggcgc aaatgctggt    6060
tcggttgctg aaggggtggg tacagatggc aacatcttca ccattgctga attcacagcc    6120
ggtgcagcag ccagtgatat ccttgatttc actgccatgc ctgttgataa cacgaacact    6180
```

```
gctccagcca ctgggcatga gttcatcgcg gtaggcactg aagctagcat tggtgacgat    6240
gccaccatca ttgtcttcac ggcgggtgtt gcggccgacg cagcaaccat cgtgacacag    6300
tttgctgatg gtgcgggaga tttccgttca gcagatgcta ctgcacgtaa cgctgacttt    6360
gctattgata gccagttgat cttcctgatt gacgatggcg ctggtaatac cggtgtctgg    6420
tattgggatg atacagttgg tgctgttggc gatggtattg tcgatgctga tgagctttcg    6480
cagattgccc agttgactgg agtcgtcact gccgagctga cggttgataa cttcgtcctc    6540
gctctggaag tcctgtttca aggcccgatg gcctcgccgc gtgcgaacga tgcgccgatt    6600
gtgctgttac atggttttac gggctggggc cgggaagaaa tgctgggttt caaatactgg    6660
ggcggcgtcc gcggcgatat cgaacaatgg ttgaatgata atggctatcg cacctatacc    6720
ttggccgtcg gcccgttgtc gagcaattgg gatcgcgcgt gcgaagcgta tgcccaattg    6780
gtcggcggca ccgtcgatta tggtgccgcg catgccgcga atgatggcca tgcccgcttt    6840
ggccgcacct atccgggctt gttgccgaaa ttgaaacgcg gcggccgtgt ccatatcatt    6900
gcccatagcc aaggcggcca aacggcccgt atgttggtct cgttgttgga aaatggcagc    6960
caagaagaac gcgaatatgc caaagaacat aatgtctcgt tgagcccgtt gtttgaaggc    7020
ggccatcgct tcgtcttgtc ggtcaccacc atcgccaccc gcatgatgg caccaccttg    7080 gtcaatatgg tcgattttac cgatcgcttt ttcgatttgc aaaaagccgt cttggaagcc    7140
gccgcagtcg cgtcgaatgc cccgtacacc agcgaaattt atgatttcaa attggatcaa    7200
tggggcttgc gtcgcgaacc gggcgaatcg tttgatcatt atttcgaacg cttgaaacgc    7260
tcgccggtct ggaccagcac ggatacggcc cgctatgatt tgagcgtccc gggcgccgaa    7320
accttgaatc gctgggtcaa agcgtcgccg aataccattt atttgtcgtt cagcaccgaa    7380
cgcacctatc gtgcgccttt gaccggcaat tattatccgg aattgggcat gaatgcgttt    7440
tcggccatcg tctgcgcgcc gttcttgggc agctatcgca atgcggcctt gggcattgat    7500
tcgcattggt tgggcaatga tgcatcgtc aataccattt cgatgaatgg cccgaaacgc    7560
ggcagcaatg atcgcatcgt cccgtatgat ggcaccttga agaaaggcgt ctggaatgat    7620
atgggcacct ataaagtcga tcatttggaa gtcattggcg tcgatccgaa tccgtcgttc    7680
aacattcgtg cgttttatct gcgtttagcg gaacaactgg cgtccctgcg tccgtga      7737
```

<210> SEQ ID NO 5
<211> LENGTH: 2980
<212> TYPE: DNA
<213> ORGANISM: Artificial Sequence
<220> FEATURE:
<223> OTHER INFORMATION: Synthetic: SlayerNtermL1lip fusion, sequence

<400> SEQUENCE: 5

```
tttaacattc taaatgggcg caagtccgta taaatttacc acgaatcggg tttaatcgca      60
gagcggcgag gcatcgtttt acaacccgcc cggcaaagaa agtgttgtgg gggcgacgcc     120
tacgtcgcga taaatcgaag tcgtgtcgct aatcgacaaa acaaacgtac tcgaagcccc     180
tacggcacga agcccggcag cgtagcggaa ttcgggaatg gcctggctcc gaactccccg     240
gattgcgcca tgctccatcc gggctgcgct gtttagactc gccgaaagcg gtcggtagcg     300
atttatcagc gagaaacctt gttaacttta tgcgtatggg cgacaacccc cgtccggcat     360
aagggcggca agaaagtgt tgtgggagcg acgcctacgt cgcgataaat cgaagtcgtg     420
tcgctaatcg acaaaacaaa cggactcgaa gcccctacgg cacgaagccc ggcagcgtag     480
cggaattcgg gaatggcctg gctccgaact ccccggattg cgccatgctc catccgggct     540
```

```
acgttgttta gactcgccga aagcggtcgc tagcgattta tcagcgagaa tctttgttag    600
ctttatgcgt atgggcgaca accccgtcc ggcataaggg caacaaaaag ttcagctatg    660
gaatcgatat atcgataaat aaacaatgaa aaaacatttt aattaaatca aatatataaa   720
acttaaatta cactaaaata cttcaatcat agtaatagaa agccaaattt taagcattat   780
ttcacccaaa ataagggcgg tccctagaaa aattattaaa aactctctat actcaagcac   840
cgtaagctat caactcagtc cagctcttta cttagaaagg ctgatcaagg tatagtgcat   900
acaaaattca gtgcgtatca aaacgtgtct agagttcttt ctaacaaaaa gcgaaaacct   960
caattggaga tttaacatgg cctcgccgcg tgcgaacgat gcgccgattg tgctgttaca  1020
tggttttacg ggctggggcc gggaagaaat gctgggtttc aaatactggg cggcgtccg   1080 cggcgatatc gaacaatggt tgaatgataa tggctatcgc acctatacct tggccgtcgg  1140
cccgttgtcg agcaattggg atcgcgcgtg cgaagcgtat gcccaattgg tcggcggcac  1200
cgtcgattat ggtgccgcgc atgccgcgaa tgatggccat gcccgctttg ccgcaccta   1260 tccgggcttg ttgccggaat tgaaacgcgg cggccgtgtc catatcattg cccatagcca  1320
aggcggccaa acgcccgta tgttggtctc gttgttggaa aatggcagcc aagaagaacg   1380
cgaatatgcc aaagaacata atgtctcgtt gagcccgttg tttgaaggcg ccatcgctt   1440 cgtcttgtcg gtcaccacca tcgccacccc gcatgatggc accaccttgg tcaatatggt  1500
cgattttacc gatcgctttt tcgatttgca aaaagccgtc ttggaagccg ccgcagtcgc  1560
gtcgaatgcc ccgtacacca gcgaaattta tgatttcaaa ttggatcaat ggggcttgcg  1620
tcgcgaaccg ggcgaatcgt ttgatcatta tttcgaacgc ttgaaacgct cgccggtctg  1680
gaccagcacg gatacggccc gctatgattt gagcgtcccg ggcgccgaaa ccttgaatcg  1740
ctgggtcaaa gcgtcgccga ataccatta tttgtcgttc agcaccgaac gcacctatcg   1800
tggcgccttg accggcaatt attatccgga attgggcatg aatgcgtttt cggccatcgt  1860
ctgcgcgccg ttcttgggca gctatcgcaa tgcggccttg ggcattgatt cgcattggtt  1920
gggcaatgat ggcatcgtca ataccatttc gatgaatggc ccgaaacgcg gcagcaatga  1980
tcgcatcgtc ccgtatgatg gcaccttgaa gaaaggcgtc tggaatgata tgggcaccta  2040
taaagtcgat catttggaag tcattggcgt cgatccgaat ccgtcgttca acattcgtgc  2100
gttttatctg cgtttagcgg aacaactggc gtccctgcgt ccggcaacac tctcagtgga  2160
tatcgctcaa tcctatatgg agaccttacg gtcctatggg cttgagttta acataagaca  2220
aaccaacaac ctgaccaatc ggataattaa ccgcttggaa aatcgcggcc acacacctga  2280
gcaagtagca gactggctta tgagcagggt tgcggttaaa cagcaattga gaaaactggt  2340
taaacaaggc gaattggccg agtttgatct ggatggcaat ggccgcctca atcgatctga  2400
attgctaaat gcaatgtctg ctctgtccga gacagcggtc aagaagcgc cggtcgaaga   2460 tcccacgact cccaagcctc cggccgatcc tagcatcacg accttaacgc ttactgagat  2520
tccgactcag cgtacggcta cgttaaaatg aacaatgtc gatgccgatt tggccatcga   2580
tttcatgcaa gacgtactga aactagatct aaatcgacta ggctggatgg aagacggtca  2640
attgaccgtc aacatcgaca atatcgcgat cagcgattcg gacagtaatt ctgatatcaa  2700
catcggtatg gtcgatggcg aagaattttt gttcagcgta aatacgccag tggcgctgta  2760
taccaatatt atatttgatt tgaagcaaaa cgatgatgtc attcaaaccg gcatcgtgct  2820
aacgccgacc gaaaacaacg gcggttcgtt tgaaaacggc attacctccg atgccgacaa  2880
```

```
ccacatcatc gccggtcgtc ctgaattgct gcacggcgcc tacatcgacg gcggcggggg      2940
ctacaacacg ttggaagtcg acatgaaagg cttctttgcg                            2980

<210> SEQ ID NO 6
<211> LENGTH: 3454
<212> TYPE: DNA
<213> ORGANISM: Artificial Sequence
<220> FEATURE:
<223> OTHER INFORMATION: Synthetic: SlayerNtermL1lipssp DnaB intein
      fusion, sequence

<400> SEQUENCE: 6
tttaacattc taaatgggcg caagtccgta taaatttacc acgaatcggg tttaatcgca        60
gagcggcgag gcatcgtttt acaacccgcc cggcaaagaa agtgttgtgg gggcgacgcc       120
tacgtcgcga taaatcgaag tcgtgtcgct aatcgacaaa acaaacgtac tcgaagcccc       180
tacggcacga agcccggcag cgtagcggaa ttcgggaatg gcctggctcc gaactccccg       240
gattgcgcca tgctccatcc gggctgcgct gtttagactc gccgaaagcg gtcggtagcg       300
atttatcagc gagaaacctt gttaacttta tgcgtatggg cgacaacccc cgtccggcat       360
aagggcggca agaaagtgt tgtgggagcg acgcctacgt cgcgataaat cgaagtcgtg        420
tcgctaatcg acaaaacaaa cggactcgaa gcccctacgg cacgaagccc ggcagcgtag       480
cggaattcgg gaatggcctg gctccgaact ccccggattg cgccatgctc catccgggct       540
acgttgttta gactcgccga agcggtcgc tagcgattta tcagcgagaa tctttgttag        600
ctttatgcgt atgggcgaca accccgtcc ggcataaggg caacaaaaag ttcagctatg        660
gaatcgatat atcgataaat aaacaatgaa aaacattttt aattaaatca aatatataaa       720
acttaaatta cactaaaata cttcaatcat agtaatagaa agccaaattt taagcattat       780
ttcacccaaa ataagggcgg tccctagaaa aattattaaa aactctctat actcaagcac       840
cgtaagctat caactcagtc cagctcttta cttagaaagg ctgatcaagg tatagtgcat       900
acaaaattca gtgcgtatca aaacgtgtct agagttcttt ctaacaaaaa gcgaaaacct       960
caattggaga tttaacatgg cctcgccgcg tgcgaacgat gcgccgattg tgctgttaca      1020
tggttttacg ggctggggcc gggaagaaat gctgggtttc aaatactggg gcggcgtccg      1080
cggcgatatc gaacaatggt tgaatgataa tggctatcgc acctatacct tggccgtcgg      1140
cccgttgtcg agcaattggg atcgcgcgtg cgaagcgtat gcccaattgg tcggcggcac      1200
cgtcgattat ggtgccgcgc atgccgcgaa tgatggccat gcccgctttg ccgcaccta       1260 tccgggcttg ttgccggaat tgaaacgcgg cggccgtgtc catatcattg cccatagcca      1320
aggcggccaa acggcccgta tgttggtctc gttgttggaa atggcagcc aagaagaacg      1380 cgaatatgcc aaagaacata atgtctcgtt gagcccgttg tttgaaggcg ccatcgctt       1440 cgtcttgtcg gtcaccacca tcgccacccc gcatgatggc accaccttgg tcaatatggt      1500 cgatttttacc gatcgctttt tcgatttgca aaaagccgtc ttggaagccg ccgcagtcgc      1560
gtcgaatgcc ccgtacacca gcgaaattta tgatttcaaa ttggatcaat ggggcttgcg      1620
tcgcgaaccg ggcgaatcgt ttgatcatta tttcgaacgc ttgaaacgct cgccggtctg      1680
gaccagcacg gatacggccc gctatgattt gagcgtcccg ggcgccgaaa ccttgaatcg      1740
ctgggtcaaa gcgtcgccga ataactatta tttgtcgttc agcaccgaac gcacctatcg      1800
tggcgccttg accggcaatt attatccgga attgggcatg aatgcgtttt cggccatcgt      1860
ctgcgcgccg ttcttgggca gctatcgcaa tgcggccttg gcattgatt cgcattggtt      1920
```

| | | |
|---|---|---|
| gggcaatgat ggcatcgtca ataccatttc gatgaatggc ccgaaacgcg gcagcaatga | 1980 |
| tcgcatcgtc ccgtatgatg gcaccttgaa gaaaggcgtc tggaatgata tgggcaccta | 2040 |
| taaagtcgat catttggaag tcattggcgt cgatccgaat ccgtcgttca acattcgtgc | 2100 |
| gttttatctg cgtttagcgg aacaactggc gtccctgcgt ccgtgtagag caatggccat | 2160 |
| cagcggcgat tcgttgatct cgttggcctc gaccggcaaa cgcgtcagca tcaaagattt | 2220 |
| gttggatgaa aaagatttcg aaatctgggc cattaatgaa caaccatga aattggaaag | 2280 |
| cgcgaaagtc tcgcgcgtct tctgcaccgg caaaaaattg gtctatatct tgaaaacccg | 2340 |
| cttgggccgc accattaaag ccaccgcgaa tcatcgcttt ttgaccatcg atggctggaa | 2400 |
| acgcttggat gaattgagct tgaaagaaca tattgccttg ccgcgcaaat tggaatcgtc | 2460 |
| gtcgttgcaa ttgtcgccgg aaatcgaaaa attgagccaa tcggatattt attgggatag | 2520 |
| catcgtctcg attaccgaaa ccggcgtcga agaagtcttt gatttgaccg tcccgggccc | 2580 |
| gcataatttc gtcgcgaatg atattattgt ccataatgca acactctcag tggatatcgc | 2640 |
| tcaatcctat atggagacct tacggtccta tgggcttgag tttaacataa gacaaaccaa | 2700 |
| caacctgacc aatcggataa ttaaccgctt ggaaaatcgc ggccacacac ctgagcaagt | 2760 |
| agcagactgg cttatgagca gggttgcggt taaacagcaa ttgagaaaac tggttaaaca | 2820 |
| aggcgaattg gccgagtttg atctggatgg caatggccgc ctcaatcgat ctgaattgct | 2880 |
| aaatgcaatg tctgctctgt ccagacagc ggtcgaagaa gcgccggtcg aagatcccac | 2940 |
| gactcccaag cctccggccg atcctagcat cacgaccta acgcttactg agattccgac | 3000 |
| tcagcgtacg gctacgttaa aatggaacaa tgtcgatgcc gatttggcca tcgatttcat | 3060 |
| gcaagacgta ctgaaactag atctaaatcg actaggctgg atggaagacg gtcaattgac | 3120 |
| cgtcaacatc gacaatatcg cgatcagcga ttcggacagt aattctgata tcaacatcgg | 3180 |
| tatggtcgat ggcgaagaat ttttgttcag cgtaaatacg ccagtggcgc tgtataccaa | 3240 |
| tattataattt gatttgaagc aaaacgatga tgtcattcaa accggcatcg tgctaacgcc | 3300 |
| gaccgaaaac aacggcggtt cgtttgaaaa cggcattacc tccgatgccg acaaccacat | 3360 |
| catcgccggt cgtcctgaat tgctgcacgg cgcctacatc gacggcggcg ggggctacaa | 3420 |
| cacgttggaa gtcgacatga aaggcttctt tgcg | 3454 |

<210> SEQ ID NO 7
<211> LENGTH: 3586
<212> TYPE: DNA
<213> ORGANISM: Artificial Sequence
<220> FEATURE:
<223> OTHER INFORMATION: Synthetic: SlayerNtermL1lipMxe GyrA intein
      fusion, sequence

<400> SEQUENCE: 7

| | | |
|---|---|---|
| tttaacattc taaatgggcg caagtccgta taaatttacc acgaatcggg tttaatcgca | 60 |
| gagcggcgag gcatcgtttt acaacccgcc cggcaaagaa agtgttgtgg gggcgacgcc | 120 |
| tacgtcgcga taaatcgaag tcgtgtcgct aatcgacaaa acaaacgtac tcgaagcccc | 180 |
| tacggcacga agcccggcag cgtagcgaa ttcgggaatg gcctggctcc gaactccccg | 240 |
| gattgcgcca tgctccatcc gggctgcgct gtttagactc gccgaaagcg gtcggtagcg | 300 |
| atttatcagc gagaaacctt gttaacttta tgcgtatggg cgacaacccc cgtccggcat | 360 |
| aagggcggca agaaagtgt tgtgggagcg acgcctacgt cgcgataaat cgaagtcgtg | 420 |
| tcgctaatcg acaaaacaaa cggactcgaa gcccctacgg cacgaagccc ggcagcgtag | 480 |

-continued

```
cggaattcgg gaatggcctg gctccgaact ccccggattg cgccatgctc catccgggct    540
acgttgttta gactcgccga aagcggtcgc tagcgattta tcagcgagaa tctttgttag    600
ctttatgcgt atgggcgaca accccgtcc ggcataaggg caacaaaaag ttcagctatg    660
gaatcgatat atcgataaat aaacaatgaa aaacatttt aattaaatca aatatataaa    720
acttaaatta cactaaaata cttcaatcat agtaatagaa agccaaattt taagcattat    780
ttcacccaaa ataagggcgg tccctagaaa aattattaaa aactctctat actcaagcac    840
cgtaagctat caactcagtc cagctcttta cttagaaagg ctgatcaagg tatagtgcat    900
acaaaattca gtgcgtatca aaacgtgtct agagttcttt ctaacaaaaa gcgaaaacct    960
caattggaga tttaacatgg cctcgccgcg tgcgaacgat gcgccgattg tgctgttaca   1020
tggttttacg ggctgggcc gggaagaaat gctgggtttc aaatactggg gcggcgtccg   1080
cggcgatatc gaacaatggt tgaatgataa tggctatcgc acctatacct ggccgtcgg    1140 cccgttgtcg agcaattggg atcgcgcgtg cgaagcgtat gcccaattgg tcggcggcac   1200
cgtcgattat ggtgccgcgc atgccgcgaa tgatggccat gcccgctttg ccgcaccta    1260 tccgggcttg ttgccggaat tgaaacgcgc cggccgtgtc catatcattg cccatagcca    1320
aggcggccaa acgcccgta tgttggtctc gttgttggaa aatggcagcc aagaagaacg    1380
cgaatatgcc aaagaacata atgtctcgtt gagcccgttg tttgaaggcg ccatcgctt    1440 cgtcttgtcg gtcaccacca cgccaccc gcatgatggc accacttgg tcaatatggt    1500 cgattttacc gatcgctttt tcgatttgca aaagccgtc ttggaagccg ccgcagtcgc    1560
gtcgaatgcc ccgtacacca gcgaaattta tgatttcaaa ttggatcaat ggggcttgcg   1620
tcgcgaaccg ggcgaatcgt ttgatcatta tttcgaacgc ttgaaacgct cgccggtctg   1680
gaccagcacg gatacggccc gctatgattt gagcgtcccg ggcgccgaaa ccttgaatcg   1740
ctgggtcaaa gcgtcgccga atacctatta tttgtcgttc agcaccgaac gcacctatcg   1800
tggcgccttg accggcaatt attatccgga attgggcatg aatgcgtttt cggccatcgt   1860
ctgcgcgccg ttcttgggca gctatcgcaa tgcggccttg gcattgatt cgcattggtt    1920 gggcaatgat ggcatcgtca ataccatttc gatgaatggc ccgaaacgcg gcagcaatga   1980
tcgcatcgtc ccgtatgatg gcaccttgaa gaaaggcgtc tggaatgata tgggcaccta   2040
taaagtcgat catttggaag tcattggcgt cgatccgaat ccgtcgttca acattcgtgc   2100
gttttatctg cgtttagcgg aacaactggc gtccctgcgt ccggcaatgc gcatgtgcat   2160
caccggcgat gcgttggtcg ccttgccgga aggcgaatcg gtccgtattg ccgatattgt   2220
cccgggcgcc cgtccgaata gcgataatgc gattgatttg aaagtcttgg atcgtcatgg   2280
caatccggtc ttggccgatc gcttgttcca ttcgggcgaa catccggtct ataccgtccg   2340
tacggtcgaa ggtttgcgtg tcacgggcac cgcgaatcat ccgttgttgt gcttggtcga   2400
tgtcgccggc gtcccgacct tgttgtggaa attgatcgat gaaatcaaac cgggcgatta   2460
tgcggtcatc caacgctcgg ccttttcggt cgattgcgcc ggttttgccc gtggcaaacc   2520
ggaatttgcc ccgaccacct atacggtcgg cgtcccgggt ttggtccgct tcttggaagc   2580
ccatcatcgc gatccggatg cccaagcgat cgccgatgaa ttgaccgatg ccgcttttta   2640
ttatgcgaaa gtcgcctcgg tcacggatgc gggcgtccaa ccggtctata gcttgcgcgt   2700
cgataccgcg gatcatgcct ttattaccaa tggcttcgtc agccatgccg caacactctc   2760
agtggatatc gctcaatcct atatggagac cttacggtcc tatgggcttg agtttaacat   2820
aagacaaacc aacaacctga ccaatcggat aattaaccgc ttggaaaatc gcggccacac   2880
```

```
acctgagcaa gtagcagact ggcttatgag cagggttgcg gttaaacagc aattgagaaa    2940
actggttaaa caaggcgaat tggccgagtt tgatctggat ggcaatggcc gcctcaatcg    3000
atctgaattg ctaaatgcaa tgtctgctct gtccgagaca gcggtcgaag aagcgccggt    3060
cgaagatccc acgactccca agcctccggc cgatcctagc atcacgacct taacgcttac    3120
tgagattccg actcagcgta cggctacgtt aaaatggaac aatgtcgatg ccgatttggc    3180
catcgatttc atgcaagacg tactgaaact agatctaaat cgactaggct ggatggaaga    3240
cggtcaattg accgtcaaca tcgacaatat cgcgatcagc gattcggaca gtaattctga    3300
tatcaacatc ggtatggtcg atggcgaaga atttttgttc agcgtaaata cgccagtggc    3360
gctgtatacc aatattatat ttgatttgaa gcaaaacgat gatgtcattc aaaccggcat    3420
cgtgctaacg ccgaccgaaa acaacggcgg ttcgtttgaa aacggcatta cctccgatgc    3480
cgacaaccac atcatcgccg gtcgtcctga attgctgcac ggcgcctaca tcgacggcgg    3540
cgggggctac aacacgttgg aagtcgacat gaaaggcttc tttgcg                   3586
```

<210> SEQ ID NO 8
<211> LENGTH: 300
<212> TYPE: PRT
<213> ORGANISM: Artificial Sequence
<220> FEATURE:
<223> OTHER INFORMATION: Synthetic

<400> SEQUENCE: 8

```
Gly Ala Asn Asn Gln Val Ala Ala Leu Gln Thr Ala Ala Gly Gly Ala
1               5                   10                  15

Phe Asp Gly Thr Phe Phe Asp Val Leu Ser Asn Phe Thr Val Glu Ala
                20                  25                  30

Ser Phe Glu Val Leu Ser Gln Phe Asp Pro Glu Thr Thr Leu Phe Val
            35                  40                  45

Ala Asn Pro Ile Val Glu Asp Val Asn Phe Asp Ile Val Arg Asp Val
        50                  55                  60

Asn Gly Asp Val Thr Ser Val Ser Val Ser Gly Ser Ser Leu Gly
65                  70                  75                  80

Phe Ala Gln Ser Asp Ala Gly Phe Gln Glu Leu Leu Glu Ala Gly Gln
                85                  90                  95

Val Thr Glu Val Val Phe Glu Asn Val Gly Ser Leu Asn Ser Ile Leu
            100                 105                 110

Val Ser Gly Asn Phe Val Gly Ser Tyr Asp Ala Gly Gly Ile Phe Tyr
        115                 120                 125

Glu Ser Thr Phe Glu Phe Gly Ala Asn Ala Gly Ser Val Ala Glu Gly
    130                 135                 140

Val Gly Thr Asp Gly Asn Ile Phe Thr Ile Ala Glu Phe Thr Ala Gly
145                 150                 155                 160

Ala Ala Ala Ser Asp Ile Leu Asp Phe Thr Ala Met Pro Val Asp Asn
                165                 170                 175

Thr Asn Thr Ala Pro Ala Thr Gly His Glu Phe Ile Ala Val Gly Thr
            180                 185                 190

Glu Ala Ser Ile Gly Asp Asp Ala Thr Ile Ile Val Phe Thr Ala Gly
        195                 200                 205

Val Ala Ala Asp Ala Ala Thr Ile Val Thr Gln Phe Ala Asp Gly Ala
    210                 215                 220

Gly Asp Phe Arg Ser Ala Asp Ala Thr Ala Arg Asn Ala Asp Phe Ala
225                 230                 235                 240
```

```
Ile Asp Ser Gln Leu Ile Phe Leu Ile Asp Asp Gly Ala Gly Asn Thr
                245                 250                 255

Gly Val Trp Tyr Trp Asp Asp Thr Val Gly Ala Val Gly Asp Gly Ile
            260                 265                 270

Val Asp Ala Asp Glu Leu Ser Gln Ile Ala Gln Leu Thr Gly Val Val
        275                 280                 285

Thr Ala Glu Leu Thr Val Asp Asn Phe Val Leu Ala
    290                 295                 300

<210> SEQ ID NO 9
<211> LENGTH: 100
<212> TYPE: PRT
<213> ORGANISM: Artificial Sequence
<220> FEATURE:
<223> OTHER INFORMATION: Synthetic

<400> SEQUENCE: 9

Thr Ile Ile Val Phe Thr Ala Gly Val Ala Ala Asp Ala Ala Thr Ile
1               5                   10                  15

Val Thr Gln Phe Ala Asp Gly Ala Gly Asp Phe Arg Ser Ala Asp Ala
            20                  25                  30

Thr Ala Arg Asn Ala Asp Phe Ala Ile Asp Ser Gln Leu Ile Phe Leu
        35                  40                  45

Ile Asp Asp Gly Ala Gly Asn Thr Gly Val Trp Tyr Trp Asp Asp Thr
    50                  55                  60

Val Gly Ala Val Gly Asp Gly Ile Val Asp Ala Asp Glu Leu Ser Gln
65                  70                  75                  80

Ile Ala Gln Leu Thr Gly Val Val Thr Ala Glu Leu Thr Val Asp Asn
                85                  90                  95

Phe Val Leu Ala
        100

<210> SEQ ID NO 10
<211> LENGTH: 48
<212> TYPE: PRT
<213> ORGANISM: Artificial Sequence
<220> FEATURE:
<223> OTHER INFORMATION: Synthetic

<400> SEQUENCE: 10

Ala Gly Asn Thr Gly Val Trp Tyr Trp Asp Asp Thr Val Gly Ala Val
1               5                   10                  15

Gly Asp Gly Ile Val Asp Ala Asp Glu Leu Ser Gln Ile Ala Gln Leu
            20                  25                  30

Thr Gly Val Val Thr Ala Glu Leu Thr Val Asp Asn Phe Val Leu Ala
        35                  40                  45

<210> SEQ ID NO 11
<211> LENGTH: 36
<212> TYPE: PRT
<213> ORGANISM: Artificial Sequence
<220> FEATURE:
<223> OTHER INFORMATION: Synthetic

<400> SEQUENCE: 11

Val Gly Ala Val Gly Asp Gly Ile Val Asp Ala Asp Glu Leu Ser Gln
1               5                   10                  15

Ile Ala Gln Leu Thr Gly Val Val Thr Ala Glu Leu Thr Val Asp Asn
            20                  25                  30
```

```
Phe Val Leu Ala
        35

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Thr Ala Glu Leu Thr Val Asp Asn Phe Val Leu Ala
1               5                   10
```